United States Patent
Panousis et al.

(10) Patent No.: US 9,856,326 B2
(45) Date of Patent: Jan. 2, 2018

(54) METHODS OF ADMINISTERING INHIBITORY ANTI-FACTOR XII/XIIA MONOCLONAL ANTIBODIES

(71) Applicants: CSL Behring GmbH, Marburg (DE); CSL Ltd., Parkville, Victoria (AU)

(72) Inventors: Con Panousis, Melbourne (AU); Veronika Rayzman, McKinnon (AU); Andrew Nash, Kew (AU); Michael Wilson, Elwood (AU); Stefan Schmidbauer, Lahntal (DE); Marc Nolte, Michelbach (DE)

(73) Assignees: CSL Behring GmbH, Marburg (DE); CSL Ltd., Parkville (AU)

(*) Notice: Subject to any disclaimer, the term of this patent is extended or adjusted under 35 U.S.C. 154(b) by 0 days.

(21) Appl. No.: 15/343,447

(22) Filed: Nov. 4, 2016

(65) Prior Publication Data

US 2017/0137536 A1    May 18, 2017

Related U.S. Application Data

(62) Division of application No. 14/234,021, filed as application No. PCT/EP2012/064322 on Jul. 20, 2012, now Pat. No. 9,518,127.

(60) Provisional application No. 61/510,801, filed on Jul. 22, 2011.

(30) Foreign Application Priority Data

Jul. 22, 2011  (EP) ..................... 11175105
Jan. 31, 2012  (EP) ..................... 12153310

(51) Int. Cl.
*A61K 39/395* (2006.01)
*C07K 16/40* (2006.01)
*A61K 39/00* (2006.01)

(52) U.S. Cl.
CPC ...... *C07K 16/40* (2013.01); *C12Y 304/21038* (2013.01); *A61K 2039/505* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,963,657 A * | 10/1990 | Pixley ............ | C12Y 304/21038 424/145.1 |
| 5,252,714 A | 10/1993 | Harris et al. | |
| 6,403,077 B1 | 6/2002 | Strom et al. | |
| 6,613,890 B2 | 9/2003 | White et al. | |
| 7,074,983 B2 | 7/2006 | Robl et al. | |
| 7,083,784 B2 | 8/2006 | Dall'Acqua et al. | |
| 7,112,661 B1 | 9/2006 | Miller | |
| 7,138,501 B2 | 11/2006 | Ruben et al. | |
| 7,220,840 B2 | 5/2007 | Ruben et al. | |
| 7,273,610 B2 | 9/2007 | Nixon et al. | |
| 7,329,737 B2 | 2/2008 | Sexton et al. | |
| 7,414,170 B2 | 8/2008 | Robl et al. | |
| 7,429,690 B2 | 9/2008 | Robl et al. | |
| 7,491,867 B2 | 2/2009 | Robl et al. | |
| 7,605,236 B2 | 10/2009 | Ruben et al. | |
| 7,803,981 B2 | 9/2010 | Robl et al. | |
| 7,807,863 B2 | 10/2010 | Robl et al. | |
| 7,879,328 B2 | 2/2011 | Ruben et al. | |
| 7,993,646 B2 | 8/2011 | Sexton et al. | |
| 8,101,181 B2 | 1/2012 | Ruben et al. | |
| 8,114,968 B2 | 2/2012 | Devy et al. | |
| 8,119,137 B2 * | 2/2012 | Nieswandt ............ | A61K 38/55 424/133.1 |
| 8,501,178 B2 | 8/2013 | Mi et al. | |
| 8,637,454 B2 | 1/2014 | Sternlicht | |
| 8,715,672 B2 * | 5/2014 | Nieswandt ............ | C07K 16/36 424/145.1 |
| 8,816,055 B2 | 8/2014 | Sexton et al. | |
| 8,822,653 B2 | 9/2014 | Sexton et al. | |
| 8,894,999 B2 | 11/2014 | Mi et al. | |
| 2003/0037347 A1 | 2/2003 | Robl et al. | |
| 2003/0223996 A1 | 12/2003 | Ruben et al. | |
| 2004/0087778 A1 | 5/2004 | Feige et al. | |
| 2006/0024745 A1 | 2/2006 | Pritchard | |
| 2007/0004910 A1 | 1/2007 | Sexton et al. | |
| 2007/0135620 A1 | 6/2007 | Chamberlain et al. | |
| 2008/0254039 A1 | 10/2008 | Nieswandt et al. | |
| 2009/0304685 A1 * | 12/2009 | Pritchard ............... | C07K 16/36 424/133.1 |
| 2010/0143344 A1 | 6/2010 | Baas et al. | |

FOREIGN PATENT DOCUMENTS

| | | | |
|---|---|---|---|
| EP | 0 154 316 | 9/1989 | |
| EP | 0 401 384 | 12/1990 | |
| NL | WO 9117258 A1 * | 11/1991 | ............... C07K 7/08 |

(Continued)

OTHER PUBLICATIONS

Gubernatorova et al. Biochemistry (Mosc). Nov. 2016;81(11):1309-1325.*
Scholtissek et al. J Invest Dermatol. Mar. 25, 2017. pii: S0022-202X(17)31356-8. doi: 10.1016/j.jid.2017.03.018. [Epub ahead of print].*
A. Girolami et al., "The Occasional Venous Thromboses Seen in Patients with Severe (Homozygous) FXII Deficiency are Probably Due to Associated Risk Factors: A Study of Prevalence in 21 Patients and Review of the Literature," *J. Thrombosis Thrombolysis*, 17(2): 139-143 (2004).

(Continued)

*Primary Examiner* — Michael Szperka

(74) *Attorney, Agent, or Firm* — Finnegan, Henderson, Farabow, Garrett & Dunner, LLP

(57) ABSTRACT

The invention relates to inhibitory anti-factor XII/FXIIa antibodies and methods of their use.

23 Claims, 13 Drawing Sheets

(56) References Cited

FOREIGN PATENT DOCUMENTS

| | | |
|---|---|---|
| WO | WO 89/11865 A1 | 12/1989 |
| WO | WO 90/08835 A1 | 8/1990 |
| WO | WO 91/17258 A1 | 11/1991 |
| WO | WO 92/16221 | 10/1992 |
| WO | WO 95/34326 | 12/1995 |
| WO | WO 01/79271 | 10/2001 |
| WO | WO 03/076567 A2 | 9/2003 |
| WO | WO 2004/101740 A3 | 11/2004 |
| WO | WO 2005/000892 A3 | 1/2005 |
| WO | WO 2005/001025 A3 | 1/2005 |
| WO | WO 2005/024044 A3 | 3/2005 |
| WO | WO 2005/063808 A1 | 7/2005 |
| WO | WO 2006/033386 A1 | 3/2006 |
| WO | WO 2006/066878 A1 | 6/2006 |
| WO | WO 2006/075142 A2 | 7/2006 |
| WO | WO 2007/122371 A1 | 11/2007 |
| WO | WO 2008/098720 A1 | 8/2008 |
| WO | WO 2010/080538 A1 | 7/2010 |
| WO | WO 2010/085682 A3 | 7/2010 |

OTHER PUBLICATIONS

A. Williams et al., "DX-88 and HAE: a developmental perspective," *Transfusion Apheresis Sci.*, 29: 255-258 (2003).

A.H. Schmaier et al., "Factor XII: New life for an old protein," *Throm. Haemost.*, 104: 915-918 (2010).

Alonso et al., Temporal Trends in the Incidence of Multiple Sclerosis, Neurology 2008;71:129-135.

B.L. Warren et al., "High-Dose Antithrombin III in Severe Sepsis: A Randomized Controlled Trial," *JAMA*, 286: 1869-1878 (2001).

Beattie et al., Structure and Evolution of Human α-Fetoprotein Deduced from Partial Sequence of Cloned cDNA, Gene 1982; 20:415-422.

Bergamaschi et al., Disability and Mortality in a Cohort of Multiple Sclerosis Patients: A Reappraisal, Neuroepidemiology 2005; 25:15-18.

C. Kleinschnitz et al., "Targeting coagulation factor XII provides protection from pathological thrombosis in cerebral ischemia without interfering with hemostasis," *J. Exp. Med.*, 203(3): 513-518 (2006).

C. Kuhli et al., "Factor XII Deficiency: a Thrombophilic Risk Factor for Retinal Vein Occlusion," *Am. J. Ophthalmol.*, 137: 459-464 (2004).

Chou et al., Distribution of Antihistamines Into the CSF Following Intranasal Delivery, Biopharm Drug Dispos. 1997; 18(4):335-46.

Claudio et al., Evidence of Persistent Blood-Brain Barrier Abnormalities in Chronic-Progressive Multiple Sclerosis, Acta Neuropathol 1995; 90:228-38.

Cooke et al., Serum Vitamin D-binding Protein is a Third Member of the Albumin and Alpha Fetoprotein Gene Family, J. Clin. Invest. 1985; 76:2420-2424.

D.M. Dors et al., "A Novel Sensitive Assay for Functional Factor XII Based on the Generation of Kallikrein-C1-Inhibitor Complexes in Factor XII-Deficient Plasma by Glass-Bound Factor XII," *Thromb. Haemost.*, 67(6): 644-648 (1992).

Draghia et al., Gene Delivery into the Central Nervous System by Nasal Instillation in Rats, Gene Ther. 1995; 2(6):418-423.

E. Stavrou et al. "Factor XII: What does it contribute to our understanding of the physiology and pathophysiology of hemostasis & thrombosis," *Thrombosis Research*, 125: 210-215 (2010).

E.D. Han et al., "Increased vascular permeability in C1 inhibitor-deficient mice mediated by the bradykinin type 2 receptor," *J. Clin. Invest.*, 109: 1057-1063 (2002).

E.J. Small et al., "A monoclonal antibody that inhibits activation of human Hageman factor (factor XII)," *Blood*, 65: 202-210 (1985).

European Search Report dated Aug. 7, 2012, for EP Application No. 12153341, 8 pages.

Extended European Search Report dated Jan. 12, 2012; for European Patent Application No. 11175105.3 (8 pages).

F. Citarella et al., "Structure/function analysis of human factor XII using recombinant deletion mutants: Evidence for an additional region involved in the binding to negatively charged surfaces," *Eur. J. Biochem.*, 238: 240-249 (1996).

First Examiner Report dated Nov. 24, 2014, for New Zealand Patent App. No. 619385 (2 pages).

Francis, Protein Modifications and Fusion Proteins, Focus on Growth Factors, 1992; 3(2): 1-10.

Frohman et al., Multiple Sclerosis—The Plaque and Its Pathogenesis, N Engl J Med 2006; 354:942-55.

G.M. Edelman et al., "The Covalent Structure of an Entire γG Immunoglobulin Molecule," *PNAS*, 63: 78-85 (1969).

Göbel et al., Blockade of the Kinin Receptor B1 Protects from Autoimmune CNS Disease by Reducing Leukocyte Trafficking, J. Autoimmunity 2011; 36:106-14.

Graham et al., Chemokine-Like Receptor-1 Expression by Central Nervous System-Infiltrating Leukocytes and Involvement in a Model of Autoimmune Demyelinating Disease, J Immunol. 2009; 183(10): 6717-6723 (21 pages).

H. Isawa et al., "A Mosquito Salivary Protein Inhibits Activation of the Plasma Contact System by Binding to Factor XII and High Molecular Weight Kininogen," *J. Biol. Chem.*, 277(31): 27651-27658 (2002).

Hart & Greaves, Chemerin Contributes to Inflammation by Promoting Macrophage Adhesion to VCAM-1 and Fibronectin through Clustering of VLA-4 and VLA-5, J Immunol. 2010; 185:3728-3739.

Herrmann et al., Glatiramer Acetate Attenuates Pro-Inflammatory T Cell Responses but Does Not Directly Protect Neurons from Inflammatory Cell Death, Am. J. Pathol. 2010; 177:3051-60.

I. Hagedorn et al., "Factor XIIa Inhibitor Recombinant Human Albumin Infestin-4 Abolishes Occlusive Arterial Thrombus Formation Without Affecting Bleeding," *Circulation*, 121: 1510-1517 (2010).

I.T.N. Campos et al., Identification and characterization of a novel factor XIIa inhibitor in the hematophagous insect, *Triatoma infestans* (Hemiptera: Reduviidae), *FEBS Letters*, 577: 512-516 (2004).

I.T.N. Campos et al., "Infestin, a thrombin inhibitor presents in *Triatoma infestans* midgut, a Chagas' disease vector: gene cloning, expression and characterization of the inhibitor," *Insect Biochem. Mol. Bio.*, 32: 991-997 (2002).

International Search Report and Written Opinion dated Aug. 28, 2012, for International Patent Application No. PCT/EP2012/064322, filed Jul. 20, 2012 (15 pages).

International Search Report dated Apr. 3, 1013, for PCT International Application No. EP 2013/051832, 14 pages.

Janeway et al., Immunobiology, 3$^{rd}$ edition, 1997, Garland Publishing Inc., pp. 3:1-3:11.

J. Devereux et al., "A comprehensive set of sequence analysis programs for the VAX," *Nucl. Acids Res.*, 12(1): 387-395 (1984).

J. Zalevsky et al., "Enhanced antibody half-life improves in vivo activity," *Nature Biotech.*, 28(2): 157-159 (2010).

J.H. Nuijens et al., "Activation of the Contact System of Coagulation by a Monoclonal Antibody Directed Against a Neodeterminant in the Heavy Chain Region of Human Coagulation Factor XII (Hageman Factor)*," *J. Biol. Chem.*, 264(22): 12941-12949 (1989).

K.L. Armour et al., "Recombinant human IgG molecules lacking Fcγ receptor I binding and monocyte triggering activities," *Eur. J. Immunol.*, 29: 2613-2624 (1999).

Krishnamoorthy et al., Autoimmune Disease: Multiple Sclerosis, Eur. J. Immunol 2009; 39:2031-35.

Kurtzke, Historical and Clinical Perspectives of the Expanded Disability Status Scale, Neuroepidemiology 2008; 31:1-9.

Langrish et al., IL-23 Drives a Pathogenic T Cell Population That Induces Autoimmune Inflammation, J Exp Med. 2005; 201:233-40.

Laskowski et al., Protein Inhibitors of Proteinases, Ann. Rev. Biochem. 1980; 49:593-626.

Lee et al., Compounds Acting on the Renin-Angiotensin-Aldosterone System as Potential Regulators of Autoimmune Neuroinflammation, Drugs of the Future 2010, 35(5); 393-398.

Lichenstein et al., Afamin Is a New Member of the Albumin, α-Fetoprotein, and Vitamin D-binding Protein Gene Family, J. Biol. Chem. 1994; 269 (27):18149-18154.

(56) References Cited

OTHER PUBLICATIONS

M. Hezareh et al., "Effector Function Activities of a Panel of Mutants of a Broadly Neutralizing Antibody Against Human Immunodeficiency Virus Type 1," *J. Virol.*, 75(24): 12161-12168 (2001).
M.P. Esnouf et al., "A Monoclonal Antibody Raised against Human β-factor XIIa which also Recognizes α-factor XIIa but not Factor XII or Complexes of Factor XIIa with C1 Esterase Inhibitor," *Thromb. Haemost.*, 83: 874-881 (2000).
Malik et al., Polyethylene Glycol (PEG)-modified Granulocyte-Macrophage Colony-stimulating Factor (GM-CSF) with Conserved Biological Activity, Exp. Hematol., 1992; 20:1028-1035.
Marik et al., Lesion Genesis in a Subset of Patients With Multiple Sclerosis: A Role for Innate Immunity?, Brain 2007; 130:2800-15 (26 pages).
Mathison et al., Nasal Route for Direct Delivery of Solutes to the Central Nervous System: Fact or Fiction?, J. Drug Target 1998; 5:415-41.
Morales et al., The Pathology of Multiple Sclerosis: Evidence for Heterogeneity, Adv Neurol 2006; 98:27-45.
Muller et al., Platelet Polyphosphates are Proinflammatory and Procoagulant Mediators In Vivo, Cell. 2009; 139(6): 1143-1156 (22 pages).
N. Mackman, "Role of Tissue Factor in Hemostasis, Thrombosis, and Vascular Development," *Arterioscler. Thromb. Vasc. Biol.*, 24: 1015-1022 (2004).
O.D. Ratnoff et al., "A Familial Hemorrhagic Trait Associated with a Deficiency of a Clot-promoting Fraction of Plasma," *J. Clin. Invest.*, 34(4): 602-613 (1955).
Osanai et al., Suppression of Experimental Allergic Encephalomyelitis with Liposome-Encapsulated Protease Inhibitor Therapy Through the Blood-Brain Barrier, Neurochemical Research, 1984, 9(10); 1407-1416 (abstract only).
Patent Examination Report No. 1 dated Aug. 15, 2014, for Australian Patent App. No. 2012289001 (7 pages).
Polman et al., Diagnostic Criteria for Multiple Sclerosis: 2010 Revisions to the McDonald Criteria, Ann Neurol 2011; 69:292-302.
Qu et al., Interface Between Hemostasis and Adaptive Immunity, Curr Opin Immunol, 2010; 22(5), 634-42 (13 pages).
R.A. Pixley et al., "A Monoclonal Antibody Recognizing an Icosapeptide Sequence in the Heavy Chain of Human Factor XII Inhibits Surface-catalyzed Activation," *J. Biol. Chem.*, 262(21): 10140-10145 (1987).
R.L. Shields et al., "High Resolution Mapping of the Binding Site on Human IgG1 for FcγRI, FcγRII, FcγRIII, and FcRn and Design of IgG1 Variants with Improved Binding to the FcγR," *J. Biol. Chem.*, 276(9): 6591-6604 (2001).
Rudikoff et al., Proc Natl Acad Sci U SA., Mar. 1982; 79(6):1979-83.
R.W. Colman, "Chapter 6: Contact Activation Pathway: Inflammatory, Fibrinolytic, Anticoagulant, Antiadhesive, and Antiangiogenic Activities," from Hemostasis and Thrombosis: Basic Principles and Clinical Practice Fourth Edition, (R.W. Colman et al. Eds.), Lippincott Williams & Wilkins, Philadelphia, pp. 103-121 (2001).
Ragonese et al., Mortality in Multiple Sclerosis: A Review, Eur J Neurol 2008;15:123-7.
Ravon et al., Monoclonal Antibody F1 Binds to the Kringle Domain of Factor XII and Induces Enhanced Susceptibility for Cleavage by Kallikrein, Blood 1995; 86(11):4134-43.
Restriction/Election Requirement dated Feb. 11, 2015 in U.S. Appl. No. 14/374,300.
S. Zeerleder et al., "Reevaluation of the Incidence of Thromboembolic Complications in Congenital Factor XII Deficiency," *Thromb. Haemost.*, 82: 1240-1246 (1999).
S.B. Needleman et al., "A General Method Applicable to the Search for Similarities in the Amino Acid Sequence of Two Proteins," *J. Mol. Biol.*, 48: 443-453 (1970).
S.F. Altschul et al., "Basic Local Alignment Search Tool," *J. Mol. Biol.*, 215: 403-410 (1990).
S.S. Sidhu et al., "[21] Phage Display for Selection of Novel Binding Peptides," *Methods Enzymol.*, 328: 333-363 (2000).
Schmaier, Assembly, Activation, and Physiologic Influence of the Plasma Kallikrein/Kinin System, Int. Immunopharmacol. 2008; 8:161-65.
Schmaier, The Elusive Physiologic Role of Factor XII, J. Clin. Invest. 2008; 118:3006-9.
Schuhmann et al., Stromal Interaction Molecules 1 and 2 Are Key Regulators of Autoreactive T Cell Activation in Murine Autoimmune Central Nervous System Inflammation, J. Immunol. 2010; 184:1536-42.
Sobel& Mitchell, Fibronectin in Multiple Sclerosis Lesions, Am. J. Pathol. 1989; 135:161-68.
Stüve et al., Translational Research in Neurology and Neuroscience 2010, Arch Neurol. 2010; 67:1307-15.
T. Jostock et al., "Rapid generation of functional human IgG antibodies derived from Fab-on-phage display libraries," *J. Immunol. Methods*, 289: 65-80 (2004).
T. Koster et al., "John Hageman's factor and deep-vein thrombosis: Leiden Thrombophilia Study," *Br. J. Haematol.*, 87: 422-424 (1994).
T. Renné et al., "Defective thrombus formation in mice lacking coagulation factor XII," *J. Exper. Med.*, 202(2): 271-281 (2005).
T.A. Kunkel et al., "Rapid and Efficient Site-Specific Mutagenesis without Phenotypic Selection," *Methods Enzymol.*, 154: 367-382 (1987).
T.F. Smith, "Comparison of Biosequences," *Advances Applied Mathematics*, 2: 482-489 (1981).
Tans et al., Studies on the Effect of Serine Protease Inhibitors on Activated Contact Factors Application in Amidolytic Assays for Factor XIIa, Plasma Kallikrein and Factor XIa, Eur. J. Biochem. 1987; 164:637-42.
The International Multiple Sclerosis Genetics Consortium & the Wellcome Trust Case Control Consortium 2, Genetic Risk and a Primary Role for Cell-Mediated Immune Mechanisms in Multiple Sclerosis, Nature 2011; 476:214-9.
U.S. Appl. No. 61/510,801, filed Jul. 2, 2011.
W.F. Dall'Acqua et al., "Modulation of the Effector Functions of a Human IgG1 through Engineering of Its Hinge Region," *J. Immunol.*, 177: 1129-1138 (2006).
W.-M. Halbmayer et al., "Factor XII (Hageman Factor) Deficiency: A Risk Factor in the Development of Thromboembolism," *Wiener Medizinische Wochenschrift*, 143: 43-50 (1993).
W.R. Pearson et al., "Improved tools for biological sequence comparison," *Proc. Natl. Acad. Sci. USA*, 85: 2444-2448 (1988).
Wachtfogel et al., Purified Plasma Factor XIIa Aggregates Human Neutrophils and Causes Degranulation, Blood, 1986; 67: 1731-1737.
Werle et al., Strategies to Improve Plasma Half Life Time of Peptide and Protein Drugs, Amino Acids 2006; 30:351-367.
Yednock et al., Prevention of Experimental Autoimmune Encephalomyelitis by Antibodies Against α4β1 Integrin, Nature 1992; 356: 63-66.
Cao et al., "Development and Characterization of an anti-FXIIa Monoclonal Antibody for the Treatment of Hereditary Angioedema," Poster at the 2015 AAAAI annual meeting.

* cited by examiner

EVQLLESGGGLVQPGGSLRLSCAASGFTFxxxxxxWVRQAPGKGLEWVSGIRPSGGTTVYAD

SVKGRFTISRDNSKNTLYLQMNSLRAEDTAVYYCARALPRSGYLISPHYYYYALDVWGQGTT

VTVSSASTK

3F7 H2

EVQLLESGGGLVQPGGSLRLSCAASGFTFSKYIMQWVRQAPGKGLEWVSGIxxxxxxxTVYAD

SVKGRFTISRDNSKNTLYLQMNSLRAEDTAVYYCARALPRSGYLISPHYYYYALDVWGQGTT

VTVSSASTK

3F7 H3.1

EVQLLESGGGLVQPGGSLRLSCAASGFTFSKYIMQWVRQAPGKGLEWVSGIRPSGGTTVYAD

SVKGRFTISRDNSKNTLYLQMNSLRAEDTAVYYCARAxxxxxxxLISPHYYYYALDVWGQGTT

VTVSSASTK

3F7 H3.2

EVQLLESGGGLVQPGGSLRLSCAASGFTFSKYIMQWVRQAPGKGLEWVSGIRPSGGTTVYAD

SVKGRFTISRDNSKNTLYLQMNSLRAEDTAVYYCARALPRSGxxxxxxxYYYYALDVWGQGTT

VTVSSASTK

QSVLTQPPSASGTPGQRVTISCSGSSxxxxxxxYVYWYQQLPGTAPKLLIYSNNQRPSGVPDR

FSGSKSGTSASLAISGLRSEDEADYYCAAWDASLRGVFGGGTKLTVLGQPKAAPSVTL

3F7 L3.1

QSVLTQPPSASGTPGQRVTISCSGSSSNIGRNYVYWYQQLPGTAPKLLIYSNNQRPSGVPDR

FSGSKSGTSASLAISGLRSEDEADYYCxxxxxxLRGVFGGGTKLTVLGQPKAAPSVTL

3F7 L3.2

QSVLTQPPSASGTPGQRVTISCSGSSSNIGRNYVYWYQQLPGTAPKLLIYSNNQRPSGVPDR

FSGSKSGTSASLAISGLRSEDEADYYCAAWDxxxxxxFGGGTKLTVLGQPKAAPSVTL

Human/mouse/rat FXIIa catalytic domain alignment

```
                                          *
Mouse    VVGGLVALPGSHPYIAALYWGNNFCAGSLIAPCWVLTAAHCLQNRPAPEELTVVLGQDRH    414
Rat      VVGGLVALPGSHPYIAALYWGDSFCAGSLIDPCWVLTAAHCLQKRPAPEELTVVLGQDRH    414
Human    VVGGLVALRGAHPYIAALYWGHSFCAGSLIAPCWVLTAAHCLQDRPAPEDLTVVLGQERR    432
                           !             !          !

*
Mouse    NQSCEWCQTLAVRSYRLHEGFSSITYQHDLALLRLQESKTNSCAILSPHVQPVCLPSGAA    474
Rat      NQSCERCQTLAVHSYRLHEGFSSKTYQHDLALLRLR-GRKNSCAILSPHVQPVCLPSSAA    473
Human    NHSCEPCQTLAVRSYRLHEAFSPVSYQHDLALLRLQEDADGSCALLSPYVQPVCLPSGAA    492
            !       !        !          !!!!!                        !

Mouse    PPSETVLCEVAGWGHQFEGAEEYSTFLQEAQVPFIALDRCSNSNVHGDAILPGMLCAGFL    534
Rat      PPSETVLCEVAGWGHQFEGAEEYATFLQEAQVPFISLDRCSSSNVHGDAILPGMLCAGFL    533
Human    RPSETTLCQVAGWGHQFEGAEEYASFLQEAQVPFLSLERCSAPDVHGSSILPGMLCAGFL    552
                                                 !

*
Mouse    EGGTDACQGDSGGPLVCEEGTAEHQLTLRGVISWGSGCGDRNKPGVYTDVANYLAWIQKH    594
Rat      EGGADACQGDSGGPLVCDEGVTERQLTLRGVISWGSGCGDRNKPGVYTDVANYLDWIQEH    593
Human    EGGTDACQGDSGGPLVCEDQAAERRLTLQGIISWGSGCGDRNKPGVYTDVAYYLAWIREH    612
            !              !  !!                                   !

Mouse    IAS   597
Rat      TAF   596
Human    TVS   615
```

B

METHODS OF ADMINISTERING INHIBITORY ANTI-FACTOR XII/XIIA MONOCLONAL ANTIBODIES

The invention relates to inhibitory anti-factor XII/FXIIa antibodies and methods of their use.

Factor XII (Hageman Factor) is a serum glycoprotein with a molecular weight of about 80 kDa. Besides an autoactivation by exposure to negatively charged surfaces, factor XII is additionally activated by kallikrein by proteolytic cleavage to form alpha-factor XIIa, which is then further converted, for example by trypsin, into beta-factor XIIa (FXIIa-β). Alpha-factor XIIa is composed of the N-terminal heavy chain of about 50 kDa, which contains the contact binding domain, and the C-terminal light chain of about 28 kDa, which contains the catalytic center. The heavy and light chains are connected by a disulfide bond. FXIIa-β is an active form of FXII of about 30 kDa, consisting of the complete light chain and a 2000 Da fragment of the heavy chain linked by a disulfide bond.

Vessel wall injury triggers sudden adhesion and aggregation of blood platelets, followed by the activation of the plasma coagulation system and the formation of fibrin-containing thrombi, which occlude the site of injury. These events are crucial to limit post-traumatic blood loss but may also occlude diseased vessels leading to ischemia and infarction of vital organs. In the waterfall model, blood coagulation proceeds by a series of reactions involving the activation of zymogens by limited proteolysis culminating in generation of thrombin, which converts plasma fibrinogen to fibrin and activates platelets. In turn, collagen- or fibrin-adherent platelets facilitate thrombin generation by several orders of magnitude via exposing procoagulant phospholipids (mainly phosphatidyl serine) on their outer surface, which propagates assembly and activation of coagulation protease complexes and by direct interaction between platelet receptors and coagulation factors.

Two converging pathways for coagulation exist that are triggered by either extrinsic (vessel wall) or intrinsic (blood-borne) components of the vascular system. The "extrinsic" pathway is initiated by the complex of the plasma factor VII (FVII) with the integral membrane protein tissue factor (TF), an essential coagulation cofactor that is absent on the luminal surface but strongly expressed in subendothelial layers of the vessel and which is accessible or liberated via tissue injury. TF expressed in circulating microvesicles might also contribute to thrombus propagation by sustaining thrombin generation on the surface of activated platelets. The "intrinsic" or contact activation pathway is initiated when factor XII (FXII, Hageman factor) comes into contact with negatively charged surfaces in a reaction involving high molecular weight kininogen and plasma kallikrein. FXII can be activated by macromolecular constituents of the subendothelial matrix such as glycosaminoglycans and collagens, sulfatides, nucleotides, polyphosphates and other soluble polyanions or non-physiological material such as glass or polymers. One of the most potent contact activators is kaolin and this reaction serves as the mechanistic basis for the major clinical clotting test, the activated partial thromboplastin time (aPTT), which measures the coagulation capacity via the "intrinsic" pathway. In reactions propagated by platelets, activated FXII then activates FXI to FXIa and subsequently FXIa activates factor IX. The complex of FVIIIa, which FVIIIa has been previously activated by traces of FXa and/or thrombin, and FIXa (the tenase complex) subsequently activates FX.

Despite its high potency to induce blood clotting in vitro, the (patho-) physiological significance of the FXII-triggered intrinsic coagulation pathway is questioned by the fact that hereditary deficiencies of FXII as well as of high molecular weight kininogen and plasma kallikrein are not associated with bleeding complications. Together with the observation that humans and mice lacking extrinsic pathway constituents such as TF and FVII suffer from severe bleeding this has led to the current hypothesis that the cessation of bleeding in vivo requires exclusively the extrinsic cascade (Mackman, N. 2004. *Role of tissue factor in hemostasis, thrombosis, and vascular development. Arterioscler. Thromb. Vasc. Biol.* 24, 101 5-1 022).

In pathological conditions, the coagulation cascade may be activated inappropriately which then results in the formation of haemostatic plugs inside the blood vessels. Thereby, vessels can be occluded and the blood supply to distal organs limited. This process is known as thrombosis, and, if the thrombus embolizes, as thromboembolism which is associated with high mortality. In addition, the use of prosthetic devices, which come into contact with blood, is severely limited because of activation of the intrinsic coagulation cascade. Suitable coating of the prosthetic surface may avoid said problem in some cases but may compromise its function in others. Examples of such prosthetic devices are hemodialysers, cardiopulmonary bypass circuits, heart valves, vascular stents and in-dwelling catheters. In cases where such devices are used, anticoagulants, such as heparin, are administered to prevent fibrin formation on the surface. However, some patients are intolerant of heparin, which can cause heparin-induced thrombocytopenia (HIT) resulting in platelet aggregation and life-threatening thrombosis. Furthermore, an inherent disadvantage of all anticoagulants used in clinics is an increased risk of serious bleeding events. Therefore, a strong need for new types of anticoagulants exist, which are not associated with such complications and that can be used in affected patients or as superior prophylaxis/therapy concept preventing thrombosis without increased bleeding risks.

For more than five decades it has been known that deficiency of coagulation factor XII is not associated with increased spontaneous or injury-related bleeding complications (Ratnoff O D & Colopy J E 1955. *A familial hemorrhagic trait associated with a deficiency of a clot-promoting fraction of plasma. J Clin Invest* 34:602-613). Indeed, although readily detected by a pathological value measured in the aPTT (a clinical clotting test that addresses the intrinsic pathway of coagulation) humans that are deficient in FXII do not suffer from abnormal bleeding even during major surgical procedures (Colman R W. *Hemostasis and Thrombosis. Basic principles & clinical practice* (eds. Colman R W, Hirsch J, Mader V J, Clowes A W, & George J) 103-122 (Lippincott Williams & Wilkins, Philadelphia, 2001)). In contrast, deficiency of FXII had been associated with increased risk of venous thrombosis (Kuhli C et al. 2004. *Factor XII deficiency: a thrombophilic risk factor for retinal vein occlusion. Am. J. Ophthalmol.* 137:459-464; Halbmayer W M et al. 1993. *Factor XII (Hageman factor) deficiency: a risk factor for development of thromboembolism. Incidence of FXII deficiency in patients after recurrent venous or arterial thromboembolism and myocardial infarction. Wien. Med. Wochenschr.* 143:43-50). Studies and case reports supporting this idea refer to the index case for FXII deficiency, Mr. John Hageman, who died of pulmonary embolism. The hypothesis that FXII deficiency is associated with an increased prothrombotic risk is challenged by a recent reevaluation of several case reports the original reports of which linked FXII deficiency with thrombosis (Girolami A et al. 2004. *The occasional venous thromboses seen in patients with severe (homozygous) FXII deficiency are probably due to associated risk factors: A study of prevalence in 21 patients and review of the literature. J. Thromb. Thrombolysis* 17:139-143). In most cases the authors identified concomitant congenital or acquired prothrombotic risk factors in combination with factor FXII deficiency that could be responsible for the thrombotic event independently of FXII. The largest epidemiological studies using well characterized patients (Koster T et al. 1994. *John Hageman's factor and deep-vein thrombosis: Leiden thrombophilia Study. Br. J. Haematol.* 87:422-424) and FXII-deficient families (Zeerleder S et al. 1999. *Reevaluation of the incidence of thromboembolic complications in congenital factor XII deficiency—a study on 73 subjects from 14 Swiss families. Thromb. Haemost.* 82:1240-1246) indicated that there is no correlation of FXII deficiency and any pro- or antithrombotic risk.

Surprisingly and in contrast to common believe of those skilled in the art it has been discovered that the factor XII-driven intrinsic coagulation pathway is involved in arterial thrombus formation in vivo but is not necessary for normal tissue-specific hemostasis (Renne T et al. 2005. *Defective thrombus formation in mice lacking factor XII. J. Exp. Med.* 202:271-281; Kleinschnitz C et al. 2006. *Targeting coagulation factor XII provides protection from pathological thrombosis in cerebral ischemic without interfering with hemostasis. J. Exp. Med.* 203, 513-518; WO2006066878). Unexpectedly, these results place factor XII in a central position in the process of pathological thrombus formation. Hence substances capable of interfering and blocking FXII activation or FXII activity may be suited to block pathogenic arterial thrombus formation and the clinical consequences thereof.

In WO2006066878 the use of antibodies against FXII/FXIIa or the use of inhibitors of FXII/FXIIa is proposed. As potential inhibitors antithrombin III (AT III), angiotensin converting enzyme inhibitor, C1 inhibitor, aprotinin, alpha-I protease inhibitor, antipain ([(S)-1-Carboxy-2-Phenylethyl]-Carbamoyl-L-Arg-L-Val-Arginal), Z-Pro-Proaldehyde-dimethyl acetate, DX88 (Dyax Inc., 300 Technology Square, Cambridge, Mass. 02139, USA; cited in: Williams A and Baird L G. 2003. DX-88 and HAE: a developmental perspective. *Transfus Apheresis Sci.* 29:255-258), leupeptin, inhibitors of prolyl oligopeptidase such as Fmoc-Ala-Pyr-CN, corn-trypsin inhibitor, mutants of the bovine pancreatic trypsin inhibitor, ecotin, yellowfin sole anticoagulant protein, *Cucurbita maxima* trypsin inhibitor-V including *Curcurbita maxima* isoinhibitors and Hamadarin (as disclosed by Isawa H et al. 2002. *A mosquito salivary protein inhibits activation of the plasma contact system by binding to factor XII and high molecular weight kininogen. J. Biol. Chem.* 277:27651-27658) have been proposed.

An ideal inhibitor of FXII/FXIIa as a therapeutic agent—while exhibiting a high inhibitory activity towards FXII/FXIIa—will not increase the risk of bleeding, be non-immunogenic and have to be administered as sparingly as possible—ideally only once. Small molecule inhibitors like Z-Pro-Pro-aldehyde-dimethyl acetate will have only a very short half-life after administration, thus requiring multiple injections, or would have to be developed into orally available slow release forms and then also be given constantly over a long period. Human plasma proteins like C1 inhibitor would at first sight fulfill all requirements, having a relatively high inhibitory activity towards FXII/FXIIa while not increasing the risk of bleeding, being non-immunogenic as a human protein and also having a considerably long plasma half-life. It was now surprisingly found that in an in vivo model of thrombosis C1 inhibitor as a prime candidate of a human FXII/FXIIa inhibitor could not be used successfully to prevent occlusion. Another proposed FXII/FXIIa inhibitor from human plasma namely AT III inhibitor would at least not fulfill the second requirement as the bleeding risk would increase (Warren B L et al. 2001. *Caring for the critically ill patient. High-dose antithrombin III in severe sepsis: a randomized controlled trial. JAMA* 286:1869-1878).

In WO2008098720A1 the use of Kazal-type serine protease inhibitor Infestin or domains thereof or modified Kazal-type serine protease inhibitors based on Infestin homologs as inhibitors of FXII/FXIIa is proposed. Selected from this subset, recombinant Infestin-4 fused to human albumin for prolongation of half-life (rHA-Infestin-4) was developed demonstrating high inhibitory activity towards FXII/FXIIa. Moreover this substance demonstrated antithrombotic efficacy without impairing (physiologic) hemostasis while demonstrating a useful half-life after fusion to human albumin (Hagedorn et al. 2010. *Factor XIIa Inhibitor Recombinant Human Albumin Infestin-4 Abolishes Occlusive Arterial Thrombus Formation Without Affecting Bleeding. Circulation.* 121:1510-1517). However, although immunogenicity was reduced during development, there is still the risk of immunogenic responses in man. Furthermore, an even longer half-life would have additional beneficial effects. Hence, it is apparent that there still exists a need for an improved medication for the treatment and/or prophylaxis of thrombosis and similar disorders. Therefore, it is an object of the present invention to satisfy such a need. A candidate for such an improved medication is an improved anti-FXII/FXIIa antibody with inhibitory activity.

Antibodies to Factor XII have been disclosed. Pixley et al (*J Biol Chem* (1987) 262, 10140-10145) disclosed monoclonal antibody B7C9 to human Factor XII. This antibody blocked surface-mediated coagulant activity, but not amidolytic activity of Factor XIIa. Small et al (*Blood* (1985), 65, 202-210) disclosed a monoclonal antibody to human Factor XII, which prevented activation of Factor XII, but not the coagulant or the amidolytic activity of activated FXII (FXIIa). Nuijens et al (*J. Biol. Chem*. (1989) 264, 12941-12949) disclosed monoclonal antibodies F1 and F3, which inhibited coagulation activity but not amidolytic activity of FXII. WO8911865 provides monoclonal antibodies produced against the light chain of FXII (B6F5, C6B7, D2E10). These antibodies inhibit the coagulation activity, but only show partial inhibition of the amidolytic activity of FXIIa. WO9008835 describes the production of monoclonal antibody that selectively binds FXIIa-β over FXII, and the development of an immunoassay that specifically detects FXIIa-β in blood. From example 7 in WO9008835, it is clear that the antibody does not inhibit amidolytic activity of FXIIa. WO9117258 describes the treatment of sepsis with an anti-FXII antibody OT-2, which binds to native FXII in plasma, and inhibits activation of the contact system in plasma, as well as amidolytic activity of FXIIa.

An objective of the present invention was the development of an improved antibody which—while exhibiting a high inhibitory activity towards FXIIa—will not increase the risk of bleeding, be non-immunogenic and have a long half-life. Since FXII has a multidomain structure including fibronectin type and EGF-like domains (reviewed by Stavrou and Schmaier (2010) *Thromb. Res.*, 125:210-215), it was believed that FXII should have additional important physiologic functions in addition to its role as FXIIa, i.e. as the enzyme following activation. New studies have demonstrated now that FXII contributes to cell proliferation and growth leading to angiogenesis (reviewed by Schmaier and LaRusch (2010) *Thromb. Haemost.*, 104:915-918). Therefore, in order not to interfere with these (and may be other so far unknown) functions of FXII, it is preferable for a therapeutic antibody against FXII/FXIIa to have a clear higher affinity towards FXIIa, for example towards FXIIa-β, compared to FXII.

SUMMARY OF THE INVENTION

One aspect of the invention is therefore an anti-Factor XII/FXIIa monoclonal antibody or antigen-binding fragment thereof that has a more than 2 fold higher binding affinity to human Factor XIIa-beta than to human Factor XII and that is capable of inhibiting the amidolytic activity of human Factor XIIa. Another aspect of the invention is an anti-Factor XII/XIIa monoclonal antibody or antigen-binding fragment thereof, that inhibits human Factor XIIa-alpha by more than 50% when used at a molar ratio of FXIIa-alpha to antibody of 1:0.2.

Preferably, the antibody or antigen-binding fragment thereof has one or more of the following features:
  it binds murine FXII/FXIIa;
  the level of binding of the antibody to a polypeptide comprising SEQ ID NO: 2 or relevant fragment thereof in which (a) the asparagine residue at position 398 of SEQ ID NO: 2 is substituted for lysine; or (b) the isoleucine residue at position 438 of SEQ ID NO: 2 is substituted for alanine, is lower than the level of binding of the protein to the corresponding polypeptide comprising SEQ ID NO: 2 or relevant fragment thereof without said substitution;
  It comprises a heavy chain variable (vH) region which is more than 85% identical to the sequence of SEQ ID NO: 4;
  it comprises a light chain variable (vL) region which is more than 85% identical to the sequence of SEQ ID NO: 5;
  it comprises heavy chain CDR1 at least 80% identical to the sequence of SEQ ID NO: 6, and/or heavy chain CDR2 at least 60% identical with SEQ ID NO: 7, and/or heavy chain CDR3 at least 80% identical to the sequence of SEQ ID NO: 9;
  it comprises light chain CDR1 at least 50% identical with SEQ ID NO: 11, and/or light chain CDR2 of SEQ ID NO: 12, and/or light chain CDR3 with the sequence A-$X_1$-W-$X_2$-$X_3$-$X_4$-$X_5$-R-$X_6$-$X_7$ wherein $X_1$ can be A or S, $X_5$ can be L or V, the other $X_n$s can be any amino acid (SEQ ID NO: 14).
  it binds human Factor XIIa-beta with a $K_D$ of better than $10^{-8}$M.
  it competes with Infestin, in particular with infestin-4, for binding to human Factor XIIa-beta.
  it is a human IgG or variant thereof, preferably human IgG4 or variant thereof.

Another aspect of the invention is a nucleic acid encoding the antibody, or antigen-binding fragment thereof, of the invention.

Yet another aspect of the invention is a vector comprising the nucleic acid encoding the antibody, or antigen-binding fragment thereof, of the invention, operably linked to a suitable promoter sequence.

A further aspect of the invention is a cell line or yeast cell comprising the vector of the invention.

Another aspect of the invention is a method of producing the antibody or antigen binding fragment thereof of the invention, comprising culturing the cell line or yeast cell of the invention under appropriate conditions to express the antibody or antigen binding fragment thereof, and purifying the antibody or antigen binding fragment thereof from the culture supernatant.

Yet another aspect of the invention is the antibody or antigen binding fragment thereof for medical use.

A further aspect of the invention is the antibody or antigen binding fragment thereof for use in preventing and/or treating a disorder selected from the group consisting of venous, arterial or capillary thrombus formation, thrombus formation in the heart, thrombus formation during and/or after contacting blood of a human or animal subject with artificial surfaces, thromboembolism, by preventing the formation and/or the stabilization of thrombi and thereby three-dimensional intraluminal thrombus growth, or by preventing and/or treating intraluminal thrombi; interstitial lung disease, inflammation, a neurological inflammatory disease, complement activation, fibrinolysis, angiogenesis and diseases related to FXII/FXIIa-induced kinin formation or FXII/FXIIa-mediated complement activation. Yet another aspect of the invention is the antibody or antigen-binding fragment thereof for use in the treatment of intraluminal thrombi in a human or animal subject related to a disorder selected from the group consisting of venous, arterial or capillary thrombus formation, thrombus formation in the heart, thrombus formation during and/or after contacting blood of a human or animal subject with artificial surfaces, thromboembolism; interstitial lung disease, inflammation, a neurological inflammatory disease, complement activation, fibrinolysis, angiogenesis and diseases related to FXII/FXIIa-induced kinin formation or FXII/FXIIa-mediated complement activation. Preferably, the venous or arterial thrombus formation is stroke, myocardial infarction, deep vein thrombosis, portal vein thrombosis, renal vein thrombosis, jugular vein thrombosis, cerebral venous sinus thrombosis, Budd-Chiari syndrome or Paget-Schroetter disease. Preferably, the diseases related to FXII/FXIIa-induced kinin formation are selected from the group hereditary angioedema, bacterial infections of the lung, *trypanosoma* infections, hypotensive shock, pancreatitis, chagas disease, articular gout, arthritis, disseminated intravascular coagulation (DIC) and sepsis.

Preferably the interstitial lung disease is fibroproliferative and/or idiopathic pulmonary fibrosis.

Preferably, the thrombus formation occurs during and/or after contacting blood of a human or animal subject with artificial surfaces during and/or after a medical procedure performed on said human or animal subject and said antibody or antigen-binding fragment thereof is administered before and/or during and/or after said medical procedure, and further
  (i) the artificial surface is exposed to at least 80% of the blood volume of the subject and the artificial surface is at least 0.2 m² or
  (ii) the artificial surface is a container for collection of blood outside the body of the subject or
  (iii) the artificial surface is a stent, valve, intraluminal catheter, or a system for internal assisted pumping of blood.

Yet a further aspect of the invention is a medical device coated with the antibody or antigen-binding fragment thereof of the invention, wherein the device is a cardiopulmonary bypass machine, an extracorporeal membrane oxygenation system for oxygenation of blood, a device for assisted pumping of blood, a blood dialysis device, a device for the extracorporeal filtration of blood, a repository for use in the collection of blood, an intraluminal catheter, a stent, an artificial heart valve, and/or accessories for any one of said devices including tubing, cannulae, centrifugal pump, valve, port, and/or diverter.

Another aspect of the invention is the antibody or antigen-binding fragment thereof for use for administration in a patient receiving a medical procedure, wherein the medical procedure comprises contact with at least one of:
(a) heart,
(b) at least one blood vessel chosen from: the aorta, the aortic arch, a carotid artery, a coronary artery, brachiocephalic artery, vertebrobasilar circulation, intracranial arteries, renal artery, a hepatic artery, a mesenteric artery, and/or a blood vessel of the arterial system cranial to the heart,
(c) a venous blood vessel if the patient has a known septal defect;
and wherein the medical procedure comprises release of at least one embolus in at least one of said blood vessels in the body that could result in ischemia in at least one target organ and administration of the antibody or antigen binding fragment thereof before, during and/or after the medical procedure.

Another aspect of the invention is the antibody or antigen binding fragment thereof for use in the prevention or treatment of a condition associated with increased vascular permeability, in particular increased retinal vascular permeability, including progressive retinopathy, sight-threatening complication of retinopathy, macular edema, non-proliferative retinopathy, proliferative retinopathy, retinal edema, diabetic retinopathy, hypertensive retinopathy, and retinal trauma.

Another aspect of the invention is a pharmaceutical composition comprising the antibody or antigen binding fragment thereof of the invention.

BRIEF DESCRIPTION OF THE FIGURES

FIG. 3: 3F7 heavy chain stop templates used for affinity maturation. CDR regions are shaded grey and amino acid positions in each library that were randomised are designated as "x". FIG. 3 shows the amino acid sequences of 3F7 heavy chain stop template H1 (3F7 H1; SEQ ID NO: 15); 3F7 heavy chain stop template H2 (3F7 H2; SEQ ID NO: 17); 3F7 heavy chain stop template H3.1 (3F7 H3.1; SEQ ID NO: 19); and 3F7 heavy chain stop template H3.2 (3F7 H3.2; SEQ ID NO: 21).

FIG. 4: 3F7 light chain stop templates used for affinity maturation. CDR regions are shaded grey and amino acid positions in each library that were randomised are designated as "x". FIG. 4 shows the amino acid sequences of 3F7 light chain stop template L1 (3F7 L1; SEQ ID NO: 23); 3F7 light chain stop template L3.1 (3F7 L3.1; SEQ ID NO: 25); and 3F7 light chain stop template L3.2 (3F7 L3.2; SEQ ID NO: 27).

LIST OF SEQUENCES

Figure 1:
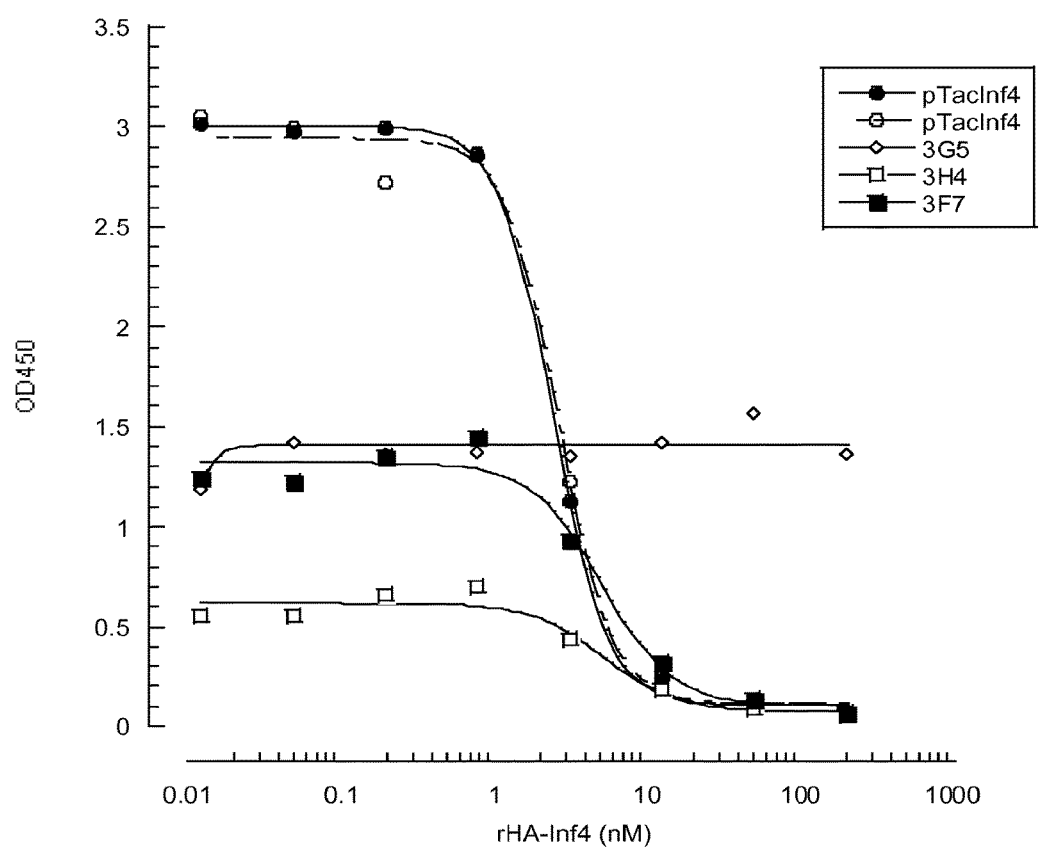
FIG. 1: Anti-FXIIa phage competition ELISA using the FXIIa amidolytic inhibitor infestin4. The concentrations of the competitor (rHA-Inf4) are shown on the X-axis. Fixed concentrations of phage-expressed Fab antibody or infestin4 (pTacInf4) used in the assay were determined using a phage titration ELISA.

SEQ ID NO: 1: Human FXII sequence
SEQ ID NO: 2: Mouse FXII sequence
SEQ ID NO: 3: Rat FXII sequence
SEQ ID NO: 4: 3F7 vH sequence
SEQ ID NO: 5: 3F7 vL sequence
SEQ ID NO: 6: 3F7 heavy chain CDR1 (HCDR1)
SEQ ID NO: 7: 3F7 heavy chain CDR2 (HCDR2)
SEQ ID NO: 8: 3F7 heavy chain CDR2 with variation
SEQ ID NO: 9: 3F7 heavy chain CDR3 (HCDR3)
SEQ ID NO: 10: 3F7 heavy chain CDR3 with variation
SEQ ID NO: 11: 3F7 light chain CDR1 (LCDR1)
SEQ ID NO: 12: 3F7 light chain CDR2 (LCDR2)
SEQ ID NO: 13: 3F7 light chain CDR3 (LCDR3)
SEQ ID NO: 14: 3F7 light chain CDR3 with variation
SEQ ID NO: 15: 3F7 heavy chain stop template H1
SEQ ID NO: 16: Oligonucleotide mutagenic trimer mix 3F7 H1
SEQ ID NO: 17: 3F7 heavy chain stop template H2
SEQ ID NO: 18: Oligonucleotide mutagenic trimer mix 3F7 H2
SEQ ID NO: 19: 3F7 heavy chain stop template H3.1
SEQ ID NO: 20: Oligonucleotide mutagenic trimer mix 3F7 H3.1
SEQ ID NO: 21: 3F7 heavy chain stop template H3.2
SEQ ID NO: 22: Oligonucleotide mutagenic trimer mix 3F7 H3.2
SEQ ID NO: 23: 3F7 light chain stop template L1
SEQ ID NO: 24: Oligonucleotide mutagenic trimer mix 3F7 L1

SEQ ID NO: 25: 3F7 light chain stop template L3.1
SEQ ID NO: 26: Oligonucleotide mutagenic trimer mix 3F7 L3.1
SEQ ID NO: 27: 3F7 light chain stop template L3.2
SEQ ID NO: 28: Oligonucleotide mutagenic trimer mix 3F7 L3.2
SEQ ID NO: 29: VR119 heavy chain CDR2
SEQ ID NO: 30: VR112 heavy chain CDR2
SEQ ID NO: 31: VR115 heavy chain CDR2
SEQ ID NO: 32: VR110 heavy chain CDR2
SEQ ID NO: 33: VR107 heavy chain CDR2
SEQ ID NO: 34: VR108 heavy chain CDR2
SEQ ID NO: 35: VR103 heavy chain CDR2
SEQ ID NO: 36: VR101 heavy chain CDR2
SEQ ID NO: 37: VR109 heavy chain CDR2
SEQ ID NO: 38: VR99 heavy chain CDR2
SEQ ID NO: 39: VR149 heavy chain CDR3
SEQ ID NO: 40: VR167 heavy chain CDR3
SEQ ID NO: 41: VR148 heavy chain CDR3
SEQ ID NO: 42: VR159 heavy chain CDR3
SEQ ID NO: 43: VR160 heavy chain CDR3
SEQ ID NO: 44: VR24 light chain CDR1
SEQ ID NO: 45: VR06 light chain CDR1
SEQ ID NO: 46: VR16 light chain CDR1
SEQ ID NO: 47: VR05 light chain CDR1
SEQ ID NO: 48: VR12 light chain CDR1
SEQ ID NO: 49: VR10 light chain CDR1
SEQ ID NO: 50: VR14 light chain CDR1
SEQ ID NO: 51: VR17 light chain CDR1
SEQ ID NO: 52: VR31 light chain CDR3
SEQ ID NO: 53: VR29 light chain CDR3
SEQ ID NO: 54: VR27 light chain CDR3
SEQ ID NO: 55: VR39 light chain CDR3
SEQ ID NO: 56: VR46 light chain CDR3
SEQ ID NO: 57: VR41 light chain CDR3
SEQ ID NO: 58: VR38 light chain CDR3
SEQ ID NO: 59: VR58 light chain CDR3
SEQ ID NO: 60: VR62 light chain CDR3
SEQ ID NO: 61: VR53 light chain CDR3
SEQ ID NO: 62: VR52 light chain CDR3
SEQ ID NO: 63: VR63 light chain CDR3
SEQ ID NO: 64: Sequencing primer CH1 Rev
SEQ ID NO: 65: Sequencing primer μLacPCRfw
SEQ ID NO: 66: Sequencing primer wt GIII stump rev
SEQ ID NO: 67: Sequencing primer KpaCLfwd
SEQ ID NO: 68: Sequencing primer LdaCLfwd
SEQ ID NO: 69: Sequencing primer PUCrev
SEQ ID NO: 70: Sequencing primer 3254
SEQ ID NO: 71: Sequencing primer Seq CL lambda
SEQ ID NO: 72: Sequencing primer Seq CH1
SEQ ID NO: 73: vH sequence of VR115
SEQ ID NO: 74: vH sequence of VR112
SEQ ID NO: 75: vL sequence of VR24
SEQ ID NO: 76: vH sequence of VR110
SEQ ID NO: 77: vH sequence of VR119

DETAILED DESCRIPTION OF THE INVENTION

An objective of the present invention was the development of an improved antibody which—while exhibiting a high inhibitory activity towards FXIIa—will not increase the risk of bleeding, be non-immunogenic and have a long half-life.

One aspect of the invention is therefore an anti-Factor XII/FXIIa monoclonal antibody or antigen-binding fragment thereof that has a more than 2 fold higher binding affinity to human Factor XIIa, preferably to human Factor XIIa-beta, than to human Factor XII and that is capable of completely inhibiting the amidolytic activity of human Factor XIIa.

Another aspect of the invention is an antibody or antigen binding fragment thereof that has a more than 2 fold higher binding affinity to human Factor XIIa, preferably to human Factor XIIa-beta, than to human Factor XII and that is capable of completely inhibiting the amidolytic activity of human Factor XIIa and that competes with an antibody comprising the sequences of SEQ ID NOs: 4 and 75 expressed as IgG4 for the binding to FXII/FXIIa.

Preferably the antibody or antigen binding fragment thereof has more than 3 fold, more preferably more than 4 fold, even more preferably more than 5 fold, more than 6 fold, more than 8 fold, more than 10 fold, more than 12 fold, more than 14 fold, more than 16 fold, most preferably more than 18 fold higher binding affinity to human Factor XIIa, preferably to human FactorXIIa-beta, than to human Factor XII.

Preferably, the antibody or antigen-binding fragment thereof completely inhibits the amidolytic activity of FXIIa at a concentration of less than 100 nM, more preferably less than 50 nM, even more preferably less than 40 nM, or even less than 30 nM. Preferably the antibody or antigen-binding fragment thereof completely inhibits at a concentration of between 1 pM and 100 nM, more preferably at a concentration between 5 pM and 50 nM. Preferably the assay for the amidolytic activity of FXIIa is carried out as described in Example 1(5).

Another aspect of the invention is an anti-Factor XII/FXIIa monoclonal antibody or antigen-binding fragment thereof that inhibits Factor XIIa-alpha, preferably human Factor XIIa-alpha, by more than 40%, preferably more than 50%, even more preferably more than 60%, when used at a molar ratio of FXIIa-alpha to antibody of 1:0.2. Alternatively, the antibody or antigen binding fragment thereof inhibits Factor XIIa-alpha, preferably human Factor XIIa-alpha, by more than 80%, preferably more than 85%, more preferably more than 90%, at a molar ratio of FXIIa-alpha to antibody of 1:0.5; most preferably, the antibody or antigen-binding fragment thereof achieves complete inhibition of FXIIa-alpha at a molar ratio of 1:0.5. Preferably the antibody or antigen-binding fragment thereof has an affinity to human FXIIa that is at least comparable to antibody 3F7 disclosed herein.

Preferably, the antibody or antigen-binding fragment thereof binds murine FXII/FXIIa; more preferably, the level of binding of the antibody to a polypeptide comprising SEQ ID NO: 2 or relevant fragment thereof in which (a) the asparagine residue at position 398 of SEQ ID NO: 2 is substituted for lysine; or (b) the isoleucine residue at position 438 of SEQ ID NO: 2 is substituted for alanine, is lower than the level of binding of the protein to the corresponding polypeptide comprising SEQ ID NO: 2 or relevant fragment thereof without said substitution. A relevant fragment of the polypeptide of SEQ ID NO: 2 comprises the catalytic center; examples are the light chain, FXIIa-beta, FXIIa-alpha, or the complete FXII.

Preferably, the antibody or antigen-binding fragment thereof comprises a heavy chain variable (vH) region which is more than 85% identical to the sequence of SEQ ID NO: 4, more preferably more than 88%, 90%, 92%, 93%, 94%, 95%, 96%, 97%, even more preferably 98%, or even 99% identical to the sequence of SEQ ID NO: 4. Preferred embodiments of the invention are antibodies or antigen-binding fragments thereof comprising a heavy chain variable region with the sequence of SEQ ID NOs: 4, 73, 74, 76 or 77.

Preferably, the antibody or antigen binding fragment thereof comprises a light chain variable (vL) region which is more than 85% identical to the sequence of SEQ ID NO: 5, more preferably more than 88%, 90%, 92%, 93%, 94%, 95%, 96%, 97%, even more preferably 98%, or even 99% identical to the sequence of SEQ ID NO: 5. Preferred embodiments of the invention are antibodies or antigen binding fragments thereof comprising a light chain variable region with the sequence of SEQ ID NOs: 5 or 75.

Preferred embodiments of the invention are antibodies or antigen binding fragments thereof with a vH region described above combined with a vL region as described above. Most preferred are antibodies with the following vH/vL combinations:

(a) A vH region of SEQ ID NO: 4 combined with a vL region of SEQ ID NO: 5 or SEQ ID NO: 75;
(b) A vH region of any of SEQ ID NOs: 4, 73, 74, 76 or 77 combined with a vL region of SEQ ID NO: 5.

Preferably, the antibodies or antigen binding fragments thereof comprise heavy chain CDR1 at least 80% identical to the sequence of SEQ ID NO: 6, preferably heavy chain CDR1 of SEQ ID NO: 6, and/or heavy chain CDR2 at least 60% identical to the sequence of SEQ ID NO: 7, and/or heavy chain CDR3 at least 80% identical to the sequence of SEQ ID NO: 9. More preferably, heavy chain CDR2 has the sequence GIX$_1$X$_2$X$_3$X$_4$X$_5$X$_6$TVYADSVKG (see SEQ ID NO: 8) wherein X$_1$ is R, N or D, X$_2$ is P, V, I or M, X$_3$ is S, P or A, X$_4$ is G, L, V, or T, X$_5$ can be any amino acid, preferably X$_5$ is G, Y, Q, K, R, N or M, and X$_6$ is T, G, or S, and/or heavy chain CDR3 has the sequence ALPRSGYLX$_1$X$_2$X$_3$X$_4$YYYYALDV (see SEQ ID NO: 10), wherein X$_1$ is I, M or V, X$_2$ is S or K, X$_3$ is P, K, T or H, and X$_4$ is H, N, G, or Q. Preferably, the antibodies or antigen binding fragments thereof comprise light chain CDR1 at least 50% identical with SEQ ID NO: 11, and/or light chain CDR2 of SEQ ID NO: 12, and/or light chain CDR3 with the sequence AX$_1$WX$_2$X$_3$X$_4$X$_5$RX$_6$X$_7$ (shown in SEQ ID NO: 14), wherein X$_1$ is A or S, X$_5$ is L or V, X$_6$ is G, L, or K, and X$_2$, X$_3$, X$_4$ and X$_7$ can be any amino acid, preferably X$_2$ is D, Y, E, T, W, E or S, X$_3$ is A, N, I, L, V, P, Q, or E, X$_4$ is S, D, P, E, Q, or R, and X$_7$ is V, A, D, T, M, or G.

Preferred embodiments of the invention are antibodies or antigen binding fragments thereof with the heavy chain CDRs described above combined with the light chain CDRs as described above.

More preferably, the antibodies or antigen binding fragments thereof comprise the combinations of heavy chain CDRs (HCDRs) and light chain CDRs (LCDRs) shown in Table 1, wherein the numbers in the columns underneath HCDR1, HCDR2, HCDR3, LCDR1, LCDR2 and LCDR3 are the respective SEQ ID NOs:

| mAb | HCDR1 | HCDR2 | HCDR3 | LCDR1 | LCDR2 | LCDR3 |
|---|---|---|---|---|---|---|
|  | 6 | 8 | 10 | 11 | 12 | 14 |
| 3F7 | 6 | 7 | 9 | 11 | 12 | 13 |
| VR119 | 6 | 29 | 9 | 11 | 12 | 13 |
| VR112 | 6 | 30 | 9 | 11 | 12 | 13 |
| VR115 | 6 | 31 | 9 | 11 | 12 | 13 |
| VR24 | 6 | 7 | 9 | 44 | 12 | 13 |
| VR110 | 6 | 32 | 9 | 11 | 12 | 13 |
| VR107 | 6 | 33 | 9 | 11 | 12 | 13 |
| VR06 | 6 | 7 | 9 | 45 | 12 | 13 |
| VR31 | 6 | 7 | 9 | 11 | 12 | 52 |
| VR108 | 6 | 34 | 9 | 11 | 12 | 13 |
| VR103 | 6 | 35 | 9 | 11 | 12 | 13 |
| VR101 | 6 | 36 | 9 | 11 | 12 | 13 |
| VR16 | 6 | 7 | 9 | 46 | 12 | 13 |
| VR29 | 6 | 7 | 9 | 11 | 12 | 53 |
| VR05 | 6 | 7 | 9 | 47 | 12 | 13 |
| VR12 | 6 | 7 | 9 | 48 | 12 | 13 |
| VR27 | 6 | 7 | 9 | 11 | 12 | 54 |
| VR10 | 6 | 7 | 9 | 49 | 12 | 13 |
| VR149 | 6 | 7 | 39 | 11 | 12 | 13 |
| VR58 | 6 | 7 | 9 | 11 | 12 | 59 |
| VR39 | 6 | 7 | 9 | 11 | 12 | 55 |
| VR167 | 6 | 7 | 40 | 11 | 12 | 13 |
| VR62 | 6 | 7 | 9 | 11 | 12 | 60 |
| VR109 | 6 | 37 | 9 | 11 | 12 | 13 |
| VR14 | 6 | 7 | 9 | 50 | 12 | 13 |
| VR46 | 6 | 7 | 9 | 11 | 12 | 56 |
| VR148 | 6 | 7 | 41 | 11 | 12 | 13 |
| VR159 | 6 | 7 | 42 | 11 | 12 | 13 |
| VR53 | 6 | 7 | 9 | 11 | 12 | 61 |
| VR52 | 6 | 7 | 9 | 11 | 12 | 62 |
| VR160 | 6 | 7 | 43 | 11 | 12 | 13 |
| VR17 | 6 | 7 | 9 | 51 | 12 | 13 |
| VR63 | 6 | 7 | 9 | 11 | 12 | 63 |
| VR41 | 6 | 7 | 9 | 11 | 12 | 57 |
| VR99 | 6 | 38 | 9 | 11 | 12 | 13 |
| VR38 | 6 | 7 | 9 | 11 | 12 | 58 |

Preferably, the antibody or antigen binding fragments thereof of the invention binds human Factor XIIa-beta with a $K_D$ of better than $10^{-7}$M, more preferably better than $3\times10^{-8}$M, more preferably better than $10^{-8}$M, even more preferably better than $3\times10^{-9}$ M, most preferably $10^{-9}$M or even $5\times10^{-10}$M.

Preferably, the antibody or antigen binding fragment thereof of the invention competes with Infestin, preferably with Infestin-4, for binding to human Factor XIIa-beta.

The antibody or antigen binding fragment thereof can be any isotype, including IgG, IgM, IgE, IgD, or IgA, and any subtype thereof. Preferably, the antibody or antigen binding fragment thereof of the invention is a human IgG or variant thereof, preferably human IgG4 or variant thereof. Methods to switch the type of antibody are well known in the art. The nucleic acid molecule encoding the $v_H$ or $v_L$ region is isolated, and operatively linked to a nucleic acid sequence encoding a different $c_H$ or $c_L$, respectively, from the constant region of a different class of immunoglobulin molecule.

The present disclosure encompasses proteins and/or antibodies described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are well known in the art.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., *Proc. Natl. Acad. Sci USA*, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; Shields et al., *J Biol Chem.* 276(9):6591-604, 2001). Additional examples of non-immunostimulatory Fc regions are described, for example, in Dall'Acqua et al., *J Immunol.* 177: 1129-1138, 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

The present disclosure also contemplates additional modifications to an antibody.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc (and therefore of Fc region-comprising molecules) into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

More preferably, the antibody of the invention is a human IgG1 or human IgG4, engineered for enhanced binding to the human neonatal Fc receptor FcRn at a lower pH, e.g. pH 6, which leads to an increased half life of the antibody in human serum. Methods to screen for optimal Fc variants for optimizing FcRn binding have been described (e.g. Zalevsky et al (2010) *Nature Biotech* 28, 157-159).

Other preferred antibodies or antigen binding fragments thereof of the invention comprise mammalian immunoglobulin constant regions, such as the constant regions of mammalian isotypes such as IgG, IgM, IgE, IgD, or IgA, and any subtype thereof. Preferably, the antibody is a mammalian IgG, including mouse IgG, pig IgG, cow IgG, horse IgG, cat IgG, dog IgG and primate IgG or variants thereof. These antibodies may be chimeric antibodies, where the human variable regions of the invention are combined with the constant region of the immunoglobulin of the selected species. Alternatively, the antibody or antigen binding fragments thereof may be produced by grafting the human CDR regions described herein into the framework residues from an immunoglobulin of the selected species.

Preferably the antibodies or antigen binding fragments thereof of the invention are in their mature form, i.e. without the signal peptide; however, the antibodies or antigen binding fragments thereof including the signal peptides are also included in the invention.

The antigen binding fragment may be any fragment of an antibody of the invention that maintains the ability to bind FXIIa. Preferred antigen binding fragments are an Fab fragment, an Fab' fragment, an F(ab')$_2$ fragment, an Fv fragment, a single chain antibody, a single chain Fv fragment, a disulfide stabilized Fv protein, or a dimer of a single chain Fv fragment. Antibodies also included in the invention are a chimeric antibody, a humanized antibody, a murinized antibody or a bispecific antibody. Methods for producing these fragments and antibodies are well known in the art (see for example, Harlow & Lane: Antibodies, A Laboratory Manual, Cold Spring Harbor Laboratory, 1988).

Also included in the invention is a fusion protein or a phage particle comprising the antigen binding fragment of the antibody of the invention. The antigen binding fragment may, for example, be fused with human serum albumin or a variant thereof. The skilled person will be well aware of other proteins that can be used as fusion partners for antigen binding fragments. The antibody or antigen binding fragment thereof may also be fused to a tag, such as a hexa-Histidine tag. The tag may be provided with a cleavable linker peptide, so that it can be removed from the antibody or antigen binding fragment thereof when desired.

Another aspect of the invention is a nucleic acid encoding the antibody, or antigen-binding fragment thereof, of the invention. Preferably, the nucleic acid also comprises a region encoding a signal peptide, preferably the nucleic acid comprises a region encoding a signal peptide for the heavy chain and a region encoding a signal peptide for the light chain.

Nucleic acid molecules encoding the polypeptides provided by the invention can be readily produced by the skilled person, using the amino acid sequences provided, the genetic code and sequences available in public databases. In addition, a variety of functionally equivalent nucleic acids can be readily produced and are therefore also included in the present invention. The nucleic acid molecules can be prepared by any suitable method, for example by direct chemical synthesis. Methods for preparing DNA are well known in the art.

Yet another aspect of the invention is a vector comprising the nucleic acid encoding the antibody, or antigen-binding fragment thereof, of the invention, operably linked to a suitable promoter sequence or incorporated into a suitable expression cassette, which may include additional regulatory elements such as enhancer elements to increase expression levels. Preferably a strong promoter is used. For expression in *E. coli*, a promoter such as T7, lac, trp or lambda promoters may be used, preferably in conjunction with a ribosome binding site and a transcription termination signal. For mammalian cells, SV40, CMV or immunoglobulin promoters can be used to provide high expression levels. Preferably, the vector is a mammalian cell expression vector, more preferably a vector selected from Lonza's GS System™ or Selexis Genetic Elements™ systems. Preferably, the vector also contains a selectable marker sequence such as gpt, neo, amp or hyg genes, and a gene amplification system such as glutamine synthetase or DHFR. Another preferred vector is a yeast expression vector, e.g. an expression vector optimized for *Pichia pastoris*. The vector may also be a viral vector, e.g. a vector based on vaccinia virus, adenovirus, or a retrovirus. The vector may also be a baculovirus for expression in insect cells.

A further aspect of the invention is a cell line or yeast cell comprising the vector of the invention. Preferably the cell line is a mammalian cell line, such as CHO, HEK293, MDCK, COS, HeLa, or myeloma cell lines such as NS0. Another embodiment is an insect cell line for use with a baculovirus, such as SF9 cells, SF21 cells, or HighFive™ cells. Yet another cell is a yeast cell, such as *Saccharomyces*, e.g. *S. cerevisiae*, or *Pichia pistoris*. Bacterial host cells such as *E. coli* are also possible. Methods for introducing DNA into the respective host cells are well known in the art. For example, when the host cell is a mammalian cell line, techniques such as lipofection or electroporation may be used.

Another aspect of the invention is a method of producing the antibody or antigen binding fragment thereof of the invention, comprising culturing the host cells, such as the cell line or yeast cell, of the invention under appropriate conditions to express the antibody or antigen binding fragment thereof. The antibody of antigen binding fragment thereof may then be purified. Preferably, the antibody or antigen binding fragment thereof is secreted by the host cell, and can then easily be purified from the culture supernatant. Techniques for purifying antibodies are well known in the art, and include techniques such as ammonium sulfate precipitation, size exclusion chromatography, affinity chromatography, ion exchange chromatography and others.

When expressed in *E. coli*, the antibodies or antigen binding fragments thereof may be produced in inclusion bodies. Methods to isolate inclusion bodies and refold the expressed protein are well known in the art.

Yet another aspect of the invention is the antibody or antigen-binding fragment thereof of the invention for medical use.

A further aspect of the invention is the antibody or antigen-binding fragment thereof for use in the prevention of the formation and/or the stabilization of thrombi in a human or animal subject. Three-dimensional intraluminal thrombus growth is reduced or even prevented. Thus, this aspect of the invention relates to the antibody or antigen-binding fragment thereof for use in the treatment or prevention of a disorder selected from the group consisting of venous, arterial or capillary thrombus formation, thrombus formation in the heart, thrombus formation during and/or after contacting blood of a human or animal subject with artificial surfaces and thromboembolism by preventing and/or treating the formation and/or stabilization of thrombi and thereby the three-dimensional intraluminal thrombus growth. Yet another aspect of the invention is the antibody or antigen binding fragment thereof for use in the treatment of intraluminal thrombi in a human or animal subject related to a disorder selected from the group consisting of venous, arterial or capillary thrombus formation, thrombus formation in the heart, thrombus formation during and/or after contacting blood of a human or animal subject with artificial surfaces or thromboembolism. Preferably, the venous or arterial thrombus formation is stroke, myocardial infarction, deep vein thrombosis, portal vein thrombosis, thromboembolism, renal vein thrombosis, jugular vein thrombosis, cerebral venous sinus thrombosis, Budd-Chiari syndrome or Paget-Schroetter disease.

A further aspect of the invention relates to the antibody or antigen binding fragment thereof for use in the prevention and/or treatment of inflammation, a neurological inflammatory disease, interstitial lung disease, complement activation, fibrinolysis, angiogenesis and diseases related to FXII/FXIIa-induced kinin formation or FXII/FXIIa-mediated complement activation. Preferably, the diseases related to FXIIFXIIa-induced kinin formation are selected from the group hereditary angioedema, bacterial infections of the lung, *trypanosoma* infections, hypotensive shock, pancreatitis, chagas disease, articular gout, arthritis, disseminated intravascular coagulation (DIC) and sepsis.

Preferably the interstitial lung disease is fibroproliferative and/or idiopathic pulmonary fibrosis.

An aspect of the invention is also a method of treatment of any of the conditions or diseases mentioned above in a subject, by administering to the subject in need thereof a therapeutically effective amount of the antibody or antigen-binding fragment thereof.

The beneficial effect of the antibody or antigen-binding fragment thereof in the various conditions can be verified, for example, by employing a suitable animal model, for example a mouse model. By comparison of animals treated with the antibody or antigen-binding fragment thereof and a control group, the beneficial effect of the treatment of the respective disease with the antibody can be demonstrated. Alternatively, patient plasma samples can be tested for relevant parameters. For example, a beneficial effect in treating or preventing disease-related symptoms in patients with hereditary angioedema can be tested by employing a mouse model, for example as described in Han et al (2002) J. Clin. Invest. 109:1057-1063. An in vitro test, using patient plasma samples can also be envisaged; treated and untreated patient plasma samples could be compared for bradykinin and/or high molecular weight kininogen levels. The antibody should reduce the bradykinin generation, and/or prevent a decrease in high molecular weight kininogen levels.

Preferably, the thrombus formation occurs during and/or after contacting blood of a human or animal subject with artificial surfaces during and/or after a medical procedure performed on said human or animal subject and said antibody or antigen binding fragment thereof is administered before and/or during and/or after said medical procedure, and further wherein
  (i) the artificial surface is exposed to at least 80% of the blood volume of the subject and the artificial surface is at least 0.2 m² or
  (ii) the artificial surface is a container for collection of blood outside the body of the subject or
  (iii) the artificial surface is a stent, valve, intraluminal catheter, or a system for internal assisted pumping of blood.

Preferably, the bleeding risk of said human or animal subject
  (i) is not increased; and/or
  (ii) is determined
    a) via the ear or finger tip bleeding time according to Duke and wherein said ear or finger tip bleeding time is not longer than 10 minutes or
    b) according to the method of Ivy and wherein the bleeding time is not longer than 10 minutes or
    c) according to the method of Marx and the bleeding time is not longer than 4 minutes.

The medical procedure may be
  i) any procedure requiring a cardiopulmonary bypass or
  ii) the oxygenation of blood via extracorporeal membrane oxygenation or
  iii) the internal assisted pumping of blood or
  iv) the dialysis of blood or
  v) the extracorporeal filtration of blood or
  vi) the collection of blood in any repository for later use in an animal or a human subject or
  vii) the use of intraluminal catheter(s) or
  viii) the use of stent(s) or
  ix) the use of artificial heart valve(s).

The antibody or antigen-binding fragment thereof of the invention may be administered before, after and/or during a medical procedure requiring cardiopulmonary bypass, or a medical procedure comprising the collection of blood in any repository for later use in an animal or human subject. It may also be administered by being coated on the artificial surface. Where the medical procedure involves blood donation, the antibody or antigen-binding fragment thereof may be:
  i) administered to the blood donor before and/or during the blood donation process or
  ii) mixed with the blood in the collection repository or
  iii) administered to the blood recipient before, during, and/or after the blood is administered to the human or animal recipient.

Preferably the amount of heparin or derivatives thereof and/or hirudin or derivatives thereof which is added in addition to the antibody or antigen-binding fragment thereof before and/or during and/or after the medical procedure is reduced or even completely omitted as compared to the amount of heparin or derivatives thereof and/or hirudin or derivatives thereof which is administered normally before and/or during said medical procedure when no said anti-FXII/FXIIa antibody or antigen binding fragment thereof is administered.

Preferably, the prothrombotic risk following the postoperative antagonism of heparin or derivatives thereof and/or the postoperative antagonism of hirudin or derivatives thereof is prevented or reduced; the prothrombotic risk may also be caused by the administration of protamine.

A further aspect of the invention is the antibody or antigen-binding fragment thereof of the invention for the prevention or the treatment of Pump Head syndrome.

Yet a further aspect of the invention is a medical device coated with an antibody or antigen-binding fragment thereof of the invention, wherein the device is a cardiopulmonary bypass machine, an extracorporeal membrane oxygenation system for oxygenation of blood, a device for assisted pumping of blood, a blood dialysis device, a device for the extracorporeal filtration of blood, a repository for use in the collection of blood, an intraluminal catheter, a stent, an artificial heart valve, and/or accessories for any one of said devices including tubing, cannulae, centrifugal pump, valve, port, and/or diverter.

Another aspect of the invention is the antibody or antigen-binding fragment thereof for use for administration in a patient receiving a medical procedure, wherein the medical procedure comprises contact with at least one of:
  (a) heart,
  (b) at least one blood vessel chosen from: the aorta, the aortic arch, a carotid artery, a coronary artery, brachiocephalic artery, vertebrobasilar circulation, intracranial arteries, renal artery, a hepatic artery, a mesenteric artery, and/or a blood vessel of the arterial system cranial to the heart,
  (c) a venous blood vessel if the patient has a known septal defect;

and wherein the medical procedure comprises release of at least one embolus in at least one of said blood vessels in the body that could result in ischemia in at least one target organ and administration of the antibody or antigen-binding fragment thereof before, during, and/or after the medical procedure.

The embolus may be comprised of bubbles, oil, fat, cholesterol, coagulated blood, and/or debris.

The target organ may be:
(a) brain, and wherein the patient has, has had, or is at risk for:
  (i) silent brain ischemia or
  (ii) a stroke caused by a nonthrombolysable substance; and/or
(b) heart, kidney, liver; and/or gastrointestinal tract organ.

Preferably, the medical procedure comprises contact with the inside of or clamping of at least one or more of said blood vessels.

Preferably, the medical procedure is a vascular procedure that comprises any one or more of a catheter, a stent, a balloon, a graft, and/or administering a contrast agent.

Preferably, the medical procedure is a vascular surgery and/or is a vascular procedure that is diagnostic. More preferably, the medical procedure is coronary angiography, carotid artery stenting, percutaneous coronary intervention, carotid endarerectomy, a cardiovascular surgery, or dilation of stenotic renal artery.

Another aspect of the invention is the antibody or antigen-binding fragment thereof for use in the prevention or treatment of a condition associated with increased vascular permeability, in particular increased retinal vascular permeability, including progressive retinopathy, sight-threatening complication of retinopathy, macular edema, non-proliferative retinopathy, proliferative retinopathy, retinal edema, diabetic retinopathy, hypertensive retinopathy, and retinal trauma.

Another aspect of the invention is a pharmaceutical composition comprising the antibody or antigen-binding fragment thereof of the invention. The antibody or antigen-binding fragment thereof can be formulated according to known methods for preparing a pharmaceutical composition. For example, it can be mixed with one or more pharmaceutically acceptable carriers, diluents or excipients. For example, sterile water or physiological saline may be used. Other substances, such as pH buffering solutions, viscosity reducing agents, or stabilizers may also be included.

A wide variety of pharmaceutically acceptable excipients and carriers are known in the art. Such pharmaceutical carriers and excipients as well as suitable pharmaceutical formulations have been amply described in a variety of publications (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000) A. Gennaro (2000) "Remington: The Science and Practice of Pharmacy", 20$^{th}$ edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc). In particular, the pharmaceutical composition comprising the antibody of the invention may be formulated in lyophilized or stable soluble form. The polypeptide may be lyophilized by a variety of procedures known in the art. Lyophilized formulations are reconstituted prior to use by the addition of one or more pharmaceutically acceptable diluents such as sterile water for injection or sterile physiological saline solution.

The pharmaceutical composition of the invention can be administered in dosages and by techniques well known in the art. The amount and timing of the administration will be determined by the treating physician or veterinarian to achieve the desired purposes. The route of administration can be via any route that delivers a safe and therapeutically effective dose to the blood of the subject to be treated. Possible routes of administration include systemic, topical, enteral and parenteral routes, such as intravenous, intraarterial, subcutaneous, intradermal, intraperitoneal, oral, transmucosal, epidural, or intrathecal. Preferred routes are intravenous or subcutaneous.

The effective dosage and route of administration are determined by factors such as age and weight of the subject, and by the nature and therapeutic range of the antibody or antigen-binding fragment thereof. The determination of the dosage is determined by known methods, no undue experimentation is required.

A therapeutically effective dose is a dose of the antibody or antigen binding fragment thereof of the invention that brings about a positive therapeutic effect in the patient or subject requiring the treatment. A therapeutically effective dose is in the range of about 0.01 to 50 mg/kg, from about 0.01 to 30 mg/kg, from about 0.1 to 30 mg/kg, from about 0.1 to 10 mg/kg, from about 0.1 to 5 mg/kg, from about 1 to 5 mg/kg, from about 0.1 to 2 mg/kg or from about 0.1 to 1 mg/kg. The treatment may comprise giving a single dose or multiple doses. If multiple doses are required, they may be administered daily, every other day, weekly, biweekly, monthly, or bimonthly or as required. A depository may also be used that slowly and continuously releases the antibody or antigen-binding fragment thereof. A therapeutically effective dose may be a dose that inhibits FXIIa in the subject by at least 50%, preferably by at least 60%, 70%, 80%, 90%, more preferably by at least 95%, 99% or even 100%.

A further aspect of the invention is an affinity-matured antibody or antigen-binding fragment thereof of the antibodies (or antigen binding fragments thereof) described above.

Definitions

Unless otherwise stated, all terms are used according to conventional usage.

"Antibody" in its broadest sense is a polypeptide comprising an immunoglobulin variable region which specifically recognizes an epitope on an antigen. Antibodies are usually comprised of two identical heavy chains and two identical light chains, each of which has a variable region at its N-terminus ($v_H$ and $v_L$ region). Usually a vH and a vL region will combine to form the antigen binding site. However, single domain antibodies, where only one variable region is present and binds to the antigen, have also been described.

Typically, an antibody contains two heavy and two light chains, connected by disulfide bonds. There are 5 major isotypes of antibodies (IgG, IgM, IgE, IgA, IgD), some of which occur as multimers of the basic antibody structure. The isotype is determined by the constant region of the heavy chains. There are two types of light chains, lambda and kappa.

The term "antibody" as used herein includes intact antibodies, as well as variants and portions thereof that retain antigen binding. This includes fragments of antibodies such as Fab fragments, F(ab')$_2$ fragments, Fab' fragments, single chain Fv fragments, or disulfide-stabilized Fv fragments. Thus, the term "antibody or antigen-binding fragment thereof" in this document is only precautionary, the term "antibody" alone is already intended to cover the antibody and antigen-binding fragments thereof.

Each heavy and light chain consists of a variable region and a constant region. The variable regions contain framework residues and hypervariable regions, which are also called complementarity determining regions or CDRs. The extent of the framework residues and CDRs is determined according to Kabat; the Kabat database is available online (Kabat E A, Wu T T, Perry H M, Gottesman K S, Foeller C (1991) *Sequences of proteins of immunological interest, 5th edn.* U.S. Department of Health and Human services, NIH, Bethesda, Md.). The CDR regions are important in binding to the epitope and therefore determine the specificity of the antibody.

A "monoclonal antibody" is an antibody produced by a single clone of B lymphocytes, or by a cell line engineered to express a single antibody.

A "chimeric antibody" is an antibody with the variable regions from one species grafted onto the constant regions from a different species. A "humanized" antibody is an antibody where CDR regions from a different species, e.g. a mouse monoclonal antibody, are grafted into the framework of a human antibody. Analogously, a "murinized" antibody is an antibody where the CDR regions from a different species, e.g. a human monoclonal antibody, are grafted into the framework of a mouse antibody. A human antibody is an antibody that is wholly derived from human, i.e. human CDRs in a human framework and any constant region suitable for administration to a human.

A "germlined" antibody is an antibody where somatic mutations that introduced changes into the framework residues are reversed to the original sequence present in the genome.

"Antigen binding fragment" refers to any fragment of an antibody that retains the ability to specifically bind the epitope of the antigen that the antibody binds to. These include but are not limited to Fab, F(ab')$_2$, or single chain Fv fragments. "Binding affinity" refers to the affinity of the antibody to its antigen. It can be measured by a variety of techniques, e.g. surface plasmon resonance based technology (BiaCore).

"Epitope" is the antigenic determinant, it is defined by the residues or particular chemical structures that the antibody makes contact with on the antigen.

"Sequence identity" relates to the similarity of amino acid sequences. The best possible alignment of two sequences is prepared, and the sequence identity is determined by the percentage of identical residues. Standard methods are available for the alignment of sequences, e.g. algorithms of Needleman and Wunsch (J Mol Biol (1970) 48, 443), Smith and Waterman (Adv Appl Math (1981) 2, 482), Pearson and Lipman (Proc Natl Acad Sci USA (1988) 85, 2444), and others. Suitable software is commercially available, e.g. the GCG suite of software (Devereux et al (1984), Nucl Acids Res 12, 387), where alignments can be produced using, for example, GAP or BESTFIT with default parameters, or successors thereof. The Blast algorithm, originally described by Altschul et al (J. Mol. Biol. (1990) 215, 403), but further refined to include gapped alignments (Blast 2), available from various sources such as the EBI, NCBI, will also produce alignments and calculate the % identity between two sequences.

"Specific binding" refers to the binding to substantially only a single antigen.

"FXII/FXIIa" refers to either or both of Factor XII and activated Factor XII (FXIIa). Thus "FXII/FXIIa inhibitor" includes inhibitors of either or both of FXII and FXIIa. Further, anti-FXII/FXIIa antibodies include antibodies that bind to and inhibit either or both of FXII and FXIIa.

"Infestins" are a class of serine protease inhibitors derived from the midgut of the hematophagous insect, *Triatoma infestans*, a major vector for the parasite *Trypanosoma cruzi*, known to cause Chagas' disease (Campos I T N et al. 32 *Insect Biochem. Mol. Bio.* 991-997, 2002; Campos I T N et al. 577 *FEBS Lett.* 512-516, 2004). This insect uses these inhibitors to prevent coagulation of ingested blood. The Infestin gene encodes 4 domains that result in proteins that can inhibit different factors in the coagulation pathway. In particular, domain 4 encodes a protein (Infestin-4) that is a strong inhibitor of FXIIa. Infestin-4 has been administered in mice without bleeding complications (WO 2008/098720). Infestin-4 has been coupled to human serum albumin (rHA-Infestin-4).

"Complete inhibition of the amidolytic activity of FXIIa" means an inhibition of 80% or more, preferably of 90% or more, more preferably of 95% or more, of the activity observed in a control experiment without any inhibitor present. "Activity of Factor XIIa" includes the activity of all forms of Factor XIIa, such as FXIIa-alpha and FXIIa-beta.

The terms "treatment" or "treating" or "therapy" are intended to be interpreted broadly; an improvement in any disease-related symptom in the subject or patient or in a level of a relevant biomarker would be included.

EXAMPLES

The following examples illustrate certain embodiments of the invention but are not intended to limit the invention to the embodiments that are exemplified. The techniques used are based on standard laboratory procedures well known to the skilled person, and described in standard laboratory manuals.

Aim

To isolate fully human antibodies from the DYAX Fab-based phage display library which are able to effectively inhibit the amidolytic activity of human FXIIa.

Materials rHA-Infestin-4 (inhibitor of FXIIa amidolytic activity) was supplied by Drs. Thomas Weimer, Holger Lind, and Stefan Schmidbauer (CSL Behring). Human FXII, FXIIa, and FXIIa beta were purchased from Enzyme Research Laboratories (supplied by Banksia Scientific, Qld, Australia). Chromogenic substrate S-2303 was from Chromogenix (supplied by Abacus ALS). Sulfo-NHS—SS-Biotin and TMB Substrate Solution were from Pierce. Enzymes and M13-KO7 helper phage were from New England Biolabs. Maxisorp immunoplates were from Nunc. Dynabeads M-280 Streptavidin were from Invitrogen Corp. Twin tec skirted 96-well PCR plates were from Eppendorf. Taq DNA polymerase was from Scientifix. ExoSAP-It was supplied by GE Healthcare. BigDye Terminator sequencing kit was from Applied Biosystems. Anti-human FXII antibody (OT-2) was from Sanquin (Amsterdam, Netherlands).

Example 1. Phage Display Selection

1) Phage Panning Method

A human Fab-based phage display library (Dyax Corp. Cambridge, Mass.) was used to screen against biotinylated FXIIa beta. Prior to initiating each round of selection, the antibody library was preincubated with 500 µL of 4% milk in PBS for 1 hr at room temperature (RT). 100 µL aliquots of M280 Streptavidin beads were coated with 3 µg of biotinylated FXIIa beta overnight at 4° C., followed by washing 3 times in PBS/0.05% Tween 20 (PBST) and once in PBS using a KingFisher magnetic particle processor (Thermo Fisher Scientific). Beads were collected using a Dynal magnetic particle separator (MPS) (Invitrogen Corp.), resuspended in 1 mL of 2% milk in PBS, and tumbled at RT for 1 hr. Blocked beads were collected using the MPS and Round 1 was performed by incubating $5.5 \times 10^{12}$ colony forming units (cfu) of phage with immobilised FXIIa beta in total volume of 1 mL at RT for 20 minutes. Following the incubation the beads were collected and washed 10 times with PBST using the Kingfisher, followed by 2 manual washes in PBS. Finally, the beads were resuspended in 500 μL PBS and designated as Round 1 output (approximately $0.5 \times 10^8$ cfu total). The Round 1 output phage were then amplified by infecting 6 mls of TG1 culture with one half (250 μL) of beads at 37° C. for 30 minutes, with shaking at 250 rpm. One mL of infected culture was removed and stored at 4° C., and $2.5 \times 10^{10}$ pfu of M13KO7 helper phage were added to the remaining 5 mLs of culture, followed by an additional incubation at 37° C. without shaking. The amplification was completed by addition of 30 mLs of 2×YT media (containing 100 μg/mL Ampicillin and 50 μg/mL Kanamycin) and an overnight incubation at 30° C. Following amplification, the bacterial pellets were harvested by centrifugation for 30 min at 4000 rpm, and the phage were precipitated from the resulting medium following the addition of 1:5 volume NaCl-PEG solution (20% PEG 8000, 2.5 M NaCl) and incubation on ice for 60 min. The precipitate was resuspended in 1 mL PBS, bacterial debris removed by centrifugation at 8000 rpm using a bench top centrifuge for 10 minutes and the phage precipitated again as described above. The final phage pellets were resuspended in a total volume of 1 mL in PBS, and titered to be used as input for the next round of selection. Rounds 2 and 3 were performed as described for Round 1. Following Round 3, a pilot scale selection of clones and preliminary analysis for binding to FXIIa beta was done by ELISA.

2) Pilot Scale Picking and ELISA Analysis of Clones from Round 3 of Phage Display Selection The preliminary screening of Round 3 output clones was carried out by Fab-phage ELISA. Colonies were picked and inoculated into 120 μL of 2×YT medium, containing 2% glucose and 100 μg/mL ampicillin. These were shaken overnight at 37° C., 250 rpm (Infors Supershaker) and designated "masterplate". These cultures were used to inoculate 100 μL of 2×YT/100 μg/mL ampicillin in deep well plates, and plates incubated at 37° C., 700 rpm to an OD600 of approximately 0.5. 100 μL of helper phage was then added to a final concentration of $0.5 \times 10^{10}$ pfu, and plates incubated without shaking for 30 min at 37° C. 2×YT media (containing 100 μg/mL Ampicillin and 100 μg/mL Kanamycin) was added to the rescued cultures to give a final concentration of 25 μg/mL of kanamycin, followed by an overnight incubation at 30° C. with shaking (650 rpm). The resultant cultures were spun at 600 g for 30 minutes, and supernatants used for phage ELISA.

For Fab-phage ELISA, Nunc immunoplates were coated overnight at 4° C. with 100 μL/well of 1 μg/mL FXIIa in PBS. Negative control wells coated with PBS alone were also included. Wells were then blocked for 2 hrs at 37° C. with 200 μL of 5% skim milk/PBS, and washed 3× in PBST. Fifty μL of 1% skim milk/PBST and 50 μL of phage culture supernatant were added to each well, and plates were incubated with shaking at room temperature for 2 hrs. Plates were than manually washed 5 times with PBST, and 100 μL of anti-M13 mAb diluted 1/5000 in 1% milk/PBST was added to each well, followed by 30 min incubation at RT with shaking. Plates were then washed as before, and 100 μL of TMB substrate was added to each well and the plates then incubated for 10 minutes at RT with shaking. The reaction was stopped by the addition of 50 μL of 2M phosphoric acid, and the absorbance was read at 450 nm in a microplate reader (Wallac Victor). Twelve clones appeared positive in the single well ELISA, and were further tested in a competition ELISA.

3) Analysis of Clones from Round 3 of Selection: Competition Phage ELISA

The twelve clones found reactive to FXIIa in a single well Fab-phage ELISA were further tested for reactivity to FXIIa in a competition ELISA. Briefly, the phage titres from culture supernatants (see previous section) were first determined using a titration ELISA. For titration ELISA, Nunc immunoplates were coated overnight at 4° C. with 100 μL/well of 1 μg/mL FXIIa in PBS. Negative control wells coated with PBS alone were also included. Wells were then blocked for 2 hrs at 37° C. with 200 μL of 5% skim milk/PBS, and washed 3× in PBS/0.05% Tween 20 (PBST). Fifty μL of phage supernatants were 4-fold serially diluted in 1% skim milk/PBST, and 100 μL of each dilution were added to the blocked plate. After 1.5 hr incubation at RT with shaking, plates were manually washed 5 times in PBST, and the rest of the ELISA protocol was followed essentially as described in previous section. The data was plotted using KaleidaGraph software with Sigmoidal curve fit, and $EC_{50}$ value was recorded.

For competition ELISA, Nunc 96-well immunoplates were coated and blocked as above. Phage concentrations were fixed at a level determined from the titration ELISA, and the competitor protein (rHA-Infestin-4) was serially diluted. Briefly, 4-fold serial dilutions of the competitor protein were made by having 100 μL of 2 times competitor in the initial well (ie. 200 nM for desired 100 nM concentration) with 75 μL dilution buffer (1% skim milk/PBST) in remaining wells, and serially diluting 25 μL of competitor down the plate. 75 μL of 2× phage stock (dilution determined from titration ELISA) were added to each well, and 100 μL from each well were transferred into a coated and blocked plate, and the rest of ELISA protocol was followed as described above. Phage expressing Infestin domain 4 (Inf4) as a gene-III fusion were used as positive control in the competition ELISA. Phage clones designated 3F7 and 3H4 showed competition with $EC_{50}$ values equivalent to the control Inf4-phage, and were selected for further analysis (FIG. 1). The results of the competition ELISA indicate that rHA-Infestin-4 is able to compete with 3F7 and 3H4 Fab-phage and most likely bind to similar regions on FXIIa. All other phage clones whilst able to bind to FXIIa were not competed by rHA-infestin-4 (as represented by clone 3G5 in FIG. 1) and hence were unlikely to bind to similar regions within the catalytic domain of FXIIa.

4) Analysis of Clone 3F7: Sequence Analysis

To determine the amino acid sequences for Fab clones 3F7 and 3H4, 5 mL overnight cultures were started using 5 μL of "masterplate" cultures, and plasmids were isolated using Qiagen miniprep kit. The Fab cassette DNA was sequenced using CH1Rev and μLacPCRfw primers (Table 2). Sequencing reactions and electrophoresis were carried out at the DNA sequencing facility of Department of Pathology, Melbourne University. The sequences were analyzed using SeqMan (Lasergene), and found to be 100% identical, hence a single antibody (3F7) with the ability to compete with infestin-4 for binding to FXIIa was obtained from panning.

TABLE 2

Sequencing primers used for the characterization of phage clones

| Primer name | Sequence | SEQ ID NO |
|---|---|---|
| CH1 Rev | 5' GTCCTTGACCAGGCAGCCCAG 3' | 64 |
| pLacPCRfw | 5' GTGAGTTAGCTCACTCATTAG 3' | 65 |
| wt GIII stump rev | 5' TTTTCATCGGCATTTTCGGTC 3' | 66 |
| KpaCLfwd | 5' CCATCTGATGAGCAGTTGAAATCT 3' | 67 |
| LdaCLfwd | 5' GTTCCCGCCCTCCTCTGAGGAGCT 3' | 68 |
| PUCrev | 5' AGCGGATAACAATTTCACACAGG 3' | 69 |
| 3254 | 5' GGTTCTGGCAAATATTCTG 3' | 70 |
| Seq CL lambda | 5' GTTGCACCGACCGAATGTA 3' | 71 |
| Seq CH1 | 5' ACCGTGAGCTGGAACAGCGGTGC GC 3' | 72 |

TABLE 3

Sequences of the variable regions and CDRs of 3F7. CDR's defined according to KABAT numbering system (Kabat E A, Wu T T, Perry H M, Gottesman K S, Foeller C (1991) Sequences of proteins of immunological interest, 5th edn. U.S. Department of Health and Human services, NIH, Bethesda, MD)

| Region | Amino acid sequence |
|---|---|
| vH | EVQLLESGGGLVQPGGSLRLSCAASGFTFSKYIMQWVRQAP GKGLEWVSGIRPSGGTTVYADSVKGRFTISRDNSKNTLYLQ MNSLRAEDTAVYYCARALPRSGYLISPHYYYYALDVWGQGT TVTVSS |
| vL | QSELTQPPSASGTPGQRVTISCSGSSSNIGRNYVYWYQQVP GTAPKLLIYSNNQRPSGVPDRFSGSKSGTSASLVISGLRSE DEADYYCAAWDASLRGVFGGGTKLTVLG |
| HCDR 1 (Kabat 31-35) | KYIMQ |
| HCDR 2 (Kabat 50-65) | GIRPSGGTTVYADSVKG |
| HCDR 3 (Kabat 95-102) | ALPRSGYLISPHYYYYALDV |
| LCDR 1 (Kabat 24-34) | SGSSSNIGRNYVY |
| LCDR 2 (Kabat 50-56) | SNNQRPS |
| LCDR 3 (Kabat 89-97) | AAWDASLRGV |

5) Analysis of Clone 3F7: FXIIa Inhibition by 3F7 mAb

Figure 2:
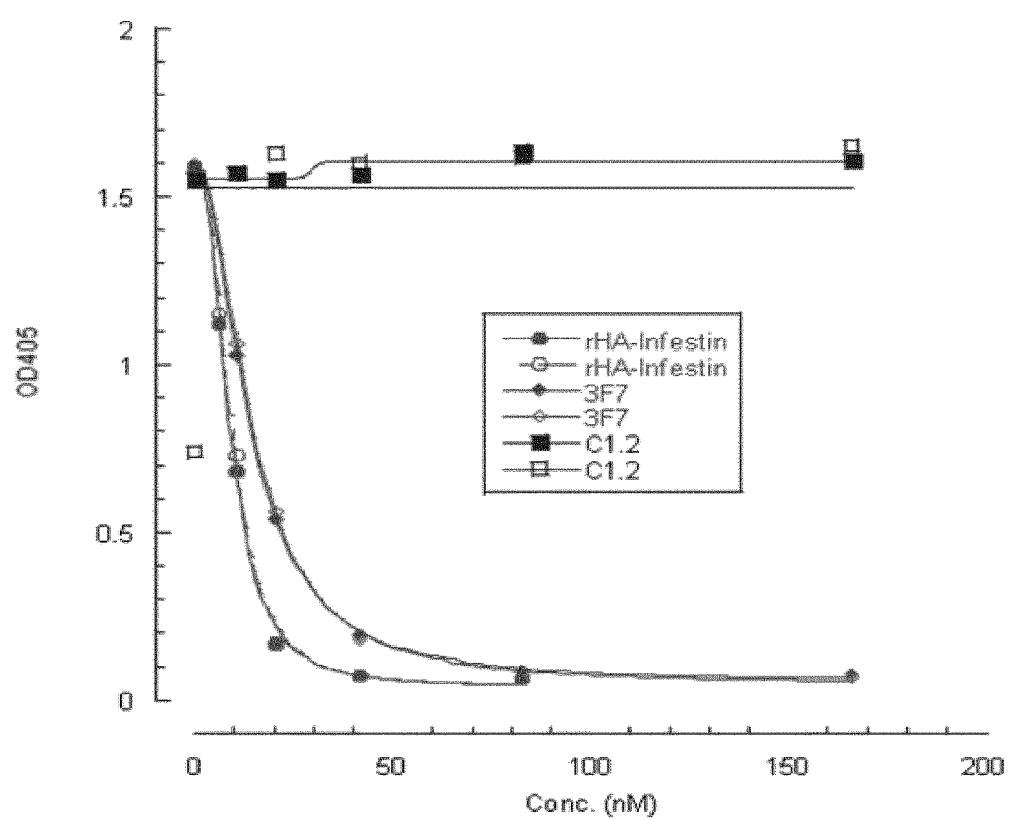
FIG. 2: Concentration-dependent inhibition of amidolytic activity of human FXIIa by monoclonal antibody 3F7 as a fully human IgG4. The anti-human GCSF receptor monoclonal antibody C1.2 (fully human IgG4) was used as a negative control and rHA-Infestin as a positive control for the assay.

To assess whether the 3F7 mAb inhibits FXIIa amidolytic activity in an in vitro assay, 3F7 Fab-phage was reformatted into full length human IgG4/lambda antibody and purified using protocols described in Example 3. Briefly, 1 µg of FXIIa was incubated in Nunc immunoplates in presence or absence of rHA-Infestin-4, 3F7 mAb or control mAb (anti-human GCSFR antibody C1.2) in a volume of 160 µL for 5 min at 37° C. Forty µL of substrate (4 mM S-2302) were added, and the plate was further incubated at 37° C. for 15 min. The reaction was stopped by the addition of 40 µL of 20% acetic acid, and colour change was detected at 405 nm in plate reader. The data was plotted using KaleidaGraph software with Sigmoidal curve fit, and $EC_{50}$ value was recorded. As shown in FIG. 2, the 3F7 antibody was found to effectively inhibit FXIIa amidolytic activity.

Example 2. Affinity Maturation of the 3F7 Antibody

The aim of the affinity maturation of 3F7 was to identify and characterise 3F7 mAb variants able to bind to human FXIIa with higher affinity than the parental antibody. Higher affinity variants have the potential to show improved inhibition of FXIIa amidolytic activity. The method for the generation of Fab-phage affinity maturation libraries (see Library construction below) is dependent on degenerate oligonucleotides annealing to a ssDNA template which is then extended to make a double stranded form for transformation. The size of the library is dependent upon transformation efficiency, and degeneracy of the primers used. The primers used (see below) covered a 19 amino acids combination (without cysteine). Libraries targeting 6 amino acid residues at a time were designed. The theoretical diversity of using trimer oligonucleotides for 6 residues is $19^6=4.7\times10^7$.

1) Design of Affinity Maturation Libraries

For each phagemid, a germline stop template was created by replacing 18 codons (6 amino acid residues) in all CDRs, except CDR-L2, with TAA stop codons. The linear design for the constructs is as follows: NcoI-VL-CL-linker-VH-SalI. Flanking NcoI and SalI sites were included for cloning into phage display pTac vector, containing remaining elements for phage display. The stop template versions named 3F7 H1, 3F7 H2, 3F7 H3.1 and 3F7 H3.2 (heavy chain variable region) and 3F7 L1, 3F7 L3.1, 3F7 L3.2 (light chain variable region) were produced by GeneArt and are shown in FIGS. 3 and 4 respectively.

2) Library Construction

Libraries were constructed using methods described by Sidhu et al. (Phage display for selection of novel binding peptides. Methods in Enzymology, 2000, vol. 238, p. 333-336) with "stop template" versions of pTac-3F7 Fab. Each stop template was used as template for the Kunkel mutagenesis method (Kunkel et al., Rapid and efficient site-specific mutagenesis without phenotypic selection. Methods in Enzymology, 1987, vol. 154, p. 367-382) with mutagenic oligonucleotides (Table 4) designed to simultaneously repair the stop codons and introduce mutations at the designed sites. The mutagenesis reactions were introduced into E. coli SS320 by electroporation, and phage production was initiated with addition of M13-KO7 helper phage. After overnight growth at 30° C., the phage were harvested by precipitation with PEG/NaCl. The mutagenesis efficiencies were assessed by sequencing of 12 clones randomly picked from each library, and ranged from 50 to 100%. Each library contained 0.75-3.75$\times10^9$ individual clones. Primer 3254 (Table 2) was used to sequence clones from libraries L1, L3.1 and L3.2 and primer Seq CL lambda (Table 2) was used to sequence clones from libraries H1, H2, H3.1 and H3.2.

TABLE 4

3F7 mutagenic trimer oligonucleotides used for affinity maturation, where each "Nnn" designates a triplet encoding one of 19 amino acids without cysteine (produced and supplied by Ella Biotech, Germany).

| | |
|---|---|
| 3F7 L1 | 5'GCTGTAGCGGTAGCAGCNnnNnnNnnNnnNnnNnnTAT GTGTATTGGTATCAGCA 3' (SEQ ID NO: 24) |
| 3F7 L3.1 | 5'GATGAAGCCGATTATTATTGTNnnNnnNnnNnnNnnNn nCTGCGTGGTGTTTTTGGT 3' (SEQ ID NO: 26) |
| 3F7 L3.2 | 5'TTATTGTGCAGCATGGGATNnnNnnNnnNnnNnnNnnT TTGGTGGTGGCACCAAA 3' (SEQ ID NO: 28) |
| 3F7 H1 | 5'AGCAAGCGGTTTTACCTTTNnnNnnNnnNnnNnnNnnT GGGTTCGCCAGGCAC 3' (SEQ ID NO: 16) |
| 3F7 H2 | 5'GGAATGGGTTAGCGGTATTNnnNnnNnnNnnNnnNnnA CCGTTTATGCAGATAGCG 3' (SEQ ID NO: 18) |
| 3F7 H3.1 | 5'TTATTATTGCGCACGTGCANnnNnnNnnNnnNnnNnnC TGATTTCTCCGCATTATTA 3' (SEQ ID NO: 20) |
| 3F7 H3.2 | 5'CACTGCCTCGTAGCGGTNnnNnnNnnNnnNnnNnnTAT TATTATTATGCCCTGGAT 3' (SEQ ID NO: 22) |

3) Library Panning

Libraries were cycled through five rounds of selection with decreasing concentration of biotinylated FXIIa beta. The target concentration was reduced 10-fold with each round, from 40 nM in Round 1 to 4 μM in Round 5. Panning was carried out in solution with the biotinylated FXIIa beta. Phage samples were incubated with antigen diluted in 4% milk in PBST (or 4% milk/PBST alone to make blank samples with no target) with rotation at RT for 1 hr. Dynal M-280 Streptavidin magnetic beads were blocked in 5% skim milk/PBS for 30 min at 37° C. with horizontal shaking. Beads were collected using MPS and phage/antigen mixture was added for 30 minutes. Beads were then washed 10 times in PBST (KingFisher Long Wash), followed by a manual wash in PBS. Beads were finally resuspended in 500 μL 50 mM DTT and incubated at 37° C. for 30 min with horizontal shaking. The eluted phage were collected, and added to 170 μL of neutralisation buffer (0.351 g L-cysteine+5 mg BSA made up to 5 mL with 1 M Tris pH 8). 330 μL of the eluted phage were used as input for the next round. Enrichment for each round of selection was calculated as ratio of eluted phage selected on target versus blank samples.

4) Analysis of Clones from 3F7 Affinity Maturation

At the completion of panning, a number of phage clones were selected from each enriched library and sequenced using the primers detailed above (library construction). Unique clones from each library were then selected based on sequence and reformatted into fully human IgG4/lambda antibodies for binding analysis. Affinity matured variants were initially screened using Biacore as unpurified cell culture supernatant to estimate binding affinities in comparison to parental 3F7 (as described in Example 4(1)). Table 5 lists the antibodies that were found to have a higher binding affinity to FXIIa beta than 3F7. The highest affinity clones tended to come from the heavy chain CDR2 and the light chain CDR 1 regions.

TABLE 5

Estimated binding affinities of 3F7 and affinity matured variants based on binding kinetics at a single FXIIa beta concentration. All antibodies were tested as unpurified IgG4 molecules in cell culture supernatants on a Biacore A100 instrument. Only variants with better affinity to FXIIa than 3F7 are shown. Refer to FIGS. 3 and 4 for library locations.

| mAb | Library | Sequence | SEQ ID NO | KD (M) |
|---|---|---|---|---|
| VR119 | H2 | NVPLYG | 29 (residues 3-8) | 1.31E−09 |
| VR112 | H2 | NVPVQG | 30 (residues 3-8) | 1.52E−09 |
| VR115 | H2 | DIPTKG | 31 (residues 3-8) | 1.56E−09 |
| VR24 | L1 | EMTVHH | 44 (residues 5-10) | 1.63E−09 |
| VR110 | H2 | DMPTKG | 32 (residues 3-8) | 2.04E−09 |
| VR107 | H2 | NPATRT | 33 (residues 3-8) | 2.45E−09 |
| VR06 | L1 | FSHPHH | 45 (residues 5-10) | 2.56E−09 |
| VR31 | L3.1 | ASWYND | 52 (residues 1-6) | 2.71E−09 |
| VR108 | H2 | NPATKT | 34 (residues 3-8) | 2.81E−09 |
| VR103 | H2 | DVPVRG | 35 (residues 3-8) | 2.87E−09 |
| VR101 | H2 | NPATRS | 36 (residues 3-8) | 3.33E−09 |
| VR16 | L1 | EFVEYN | 46 (residues 5-10) | 3.63E−09 |
| VR29 | L3.1 | ASWEIP | 53 (residues 1-6) | 3.89E−09 |
| VR05 | L1 | DTNSHH | 47 (residues 5-10) | 4.36E−09 |
| VR12 | L1 | WTEQHN | 48 (residues 5-10) | 4.45E−09 |
| VR27 | L3.1 | ASWTNE | 54 (residues 1-6) | 4.64E−09 |
| VR10 | L1 | VMVTNH | 49 (residues 5-10) | 4.97E−09 |
| VR149 | H3.2 | YLMKKN | 39 (residues 7-12) | 5.12E−09 |
| VR58 | L3.2 | PQVRLA | 59 (residues 5-10) | 5.33E−09 |
| VR39 | L3.1 | ASWWND | 55 (residues 1-6) | 5.63E−09 |
| VR167 | H3.2 | YLMKTG | 40 (residues 7-12) | 5.80E−09 |
| VR62 | L3.2 | QQVRLD | 60 (residues 5-10) | 5.81E−09 |
| VR109 | H2 | NPATNT | 37 (residues 3-8) | 5.98E−09 |
| VR14 | L1 | GMVEQN | 50 (residues 5-10) | 6.22E−09 |
| VR46 | L3.1 | ASWELP | 56 (residues 1-6) | 6.67E−09 |
| VR148 | H3.2 | YLVKKQ | 41 (residues 7-12) | 6.93E−09 |
| VR159 | H3.2 | YLVKHG | 42 (residues 7-12) | 6.93E−09 |
| VR53 | L3.2 | QQVRKT | 61 (residues 5-10) | 7.05E−09 |
| VR52 | L3.2 | ERVRLM | 62 (residues 5-10) | 7.10E−09 |
| VR160 | H3.2 | YLMKPG | 43 (residues 7-12) | 7.13E−09 |
| VR17 | L1 | FKVEET | 51 (residues 5-10) | 7.15E−09 |
| VR63 | L3.2 | NQVRLG | 63 (residues 5-10) | 8.30E−09 |
| VR41 | L3.1 | ASWSIP | 57 (residues 1-6) | 9.14E−09 |
| VR99 | H2 | NPATMT | 38 (residues 3-8) | 9.19E−09 |
| VR38 | L3.1 | ASWEVP | 58 (residues 1-6) | 9.23E−09 |
| 3F7 | | | | 3.30E−08 |

Based on the results from the estimated binding affinity screening the best 5 mabs were then purified and subjected to detailed binding affinity analysis (as described in example 4(2)). As shown in Table 6, these clones showed a 24 to 57-fold improvement in binding affinity compared to parental 3F7.

TABLE 6

Detailed Biacore analysis of the binding affinity of purified 3F7 and the top 5 affinity matured variants to FXIIa beta from Table 5. All antibodies were tested as fully human IgG4 molecules.

| 3F7 Variant | ka (1/Ms) | kd (1/s) | KD (M) | Fold affinity improvement |
|---|---|---|---|---|
| 3F7 | $1.2 \times 10^5$ | $1.1 \times 10^{-3}$ | $8.6 \times 10^{-9}$ | 1 |
| VR115 | $1.7 \times 10^5$ | $2.5 \times 10^{-5}$ | $1.5 \times 10^{-10}$ | 57 |
| VR112 | $2.5 \times 10^5$ | $4.3 \times 10^{-5}$ | $1.7 \times 10^{-10}$ | 51 |
| VR24 | $2.4 \times 10^5$ | $6.4 \times 10^{-5}$ | $2.6 \times 10^{-10}$ | 33 |
| VR110 | $1.1 \times 10^5$ | $3.9 \times 10^{-5}$ | $3.5 \times 10^{-10}$ | 25 |
| VR119 | $1.6 \times 10^5$ | $5.9 \times 10^{-5}$ | $3.6 \times 10^{-10}$ | 24 |

Example 3. IgG Production and Purification of Phage-Derived Antibodies of the Invention

1) Mammalian Expression Vector Construction

The mammalian expression vectors were constructed using standard molecular biology techniques by cloning the entire light chain (variable and constant domains) and the variable domain of the heavy chain from the selected phage-derived Fab constructs into the pRhG4 vector as previously described (Jostock et al 2004. Rapid generation of functional human IgG antibodies derived from Fab-on-phage display libraries. J Immunol Methods, 289; 65-80).

2) Cell Culture

Serum-free suspension adapted 293-T cells were obtained from Genechoice Inc. Cells were cultured in FreeStyle™ Expression Medium (Invitrogen) supplemented with penicillin/streptomycin/fungizone reagent (Invitrogen). Prior to transfection the cells were maintained at 37° C. in humidified incubators with an atmosphere of 8% $CO_2$.

3) Transient Transfection

The transient transfection of the mammalian expression vectors using 293-T cells was performed using 293fectin transfection reagent (Invitrogen) according to the manufacturer's instructions. The light and heavy chain expression vectors were combined and co-transfected with the 293-T cells. Cells (1000 ml) were transfected at a final concentration of $1 \times 10^6$ viable cells/ml and incubated in a Cellbag 2 L (Wave Biotech/GE Healthcare) for 5 days at 37° C. with an atmosphere of 8% $CO_2$ on a 2/10 Wave Bioreactor system 2/10 or 20/50 (Wave Biotech/GE Healthcare). The culture conditions were 35 rocks per minute with an angle of 8°. Pluronic® F-68 (Invitrogen), to a final concentration of 0.1% v/v, was added 4 hours post-transfection. 24 hours post-transfection the cell cultures were supplemented with Tryptone N1 (Organotechnie, France) to a final concentration of 0.5% v/v. The cell culture supernatants were harvested by centrifugation at 2500 rpm and were then passed through a 0.45 µM filter (Nalgene) prior to purification.

4) Analysis of Protein Expression

After 5 days 20 µl of culture supernatant was electrophoresed on a 4-20% Tris-Glycine SDS polyacrylamide gel and the antibody was visualised by staining with Coomassie Blue reagent.

5) Antibody Purification

Monoclonal antibodies were purified using tandem protein A affinity chromatography and desalting column chromatography. Chromatography using Hitrap MabSelect sure (1 ml, GE Healthcare, UK) and Desalting (HiPrep 26/10, GE Healthcare, UK) resins were developed using an AKTA express (GE Healthcare, UK) as per manufacturers recommended method. Briefly, equilibration of the Protein A affinity column was performed in 1×MT-PBS buffer. The filtered conditioned cell culture media (500 ml) was applied to the column at 1 ml/min and washed sequentially with 1×MT-PBS (10 ml) and 10 mM Tris, 0.5M Arginine, 150 mM NaCl pH 7.2 (80 ml). The bound antibody was then eluted with 0.1M Na Acetate pH 3.0 (8 ml) and immediately applied to the desalting column. The antibody concentration was determined chromatographically by comparison to control antibody standards. Protein fractions were pooled and concentrated using an Amicon UltraCel 50K centrifugal device (Millipore) prior to sterile filtration using 0.22 um filters.

The purity of the antibody was analysed by SDS-PAGE, where 2 µg protein in reducing Sample Buffer (Invitrogen, CA) was loaded onto a Novex NuPAGE 4-12% Bis-Tris Gel (Invitrogen, CA) and a constant voltage of 200V was applied for 40 minutes in an XCell SureLock Mini-Cell (Invitrogen, CA) with NuPAGE MES SDS running buffer before being visualised using Coomassie Stain, as per the manufacturer's instructions.

Example 4. Antibody Affinity Determination—Biacore Analysis

1) Estimated Binding Affinities from Unpurified Antibody Supernatants

Anti-human (Goat anti-human IgG (gamma) mouse adsorbed, Invitrogen, Cat No. H10500) was chemically immobilised on a CM-5 sensor surface using amine coupling chemistry. Culture supernatants were diluted 1/60 with running buffer before capture. Antibodies were captured for 180 seconds representing an average capture of 800 response units (RU). FXIIa beta was then injected at zero and 100 nM for 180 seconds, and dissociated for 180 seconds. All assays were conducted on a Biacore A100 instrument at 37 degrees Celsius and the data fitted to a 1:1 kinetic model.

2) Detailed Binding Affinity Analysis

Anti-human (Goat anti-Human IgG (gamma) mouse adsorbed, Invitrogen, Cat No. H10500) or anti mouse Fc specific antibody (Jackson Immuno Research Labs inc. Cat No. 515-005-071) was chemically immobilised on a CM-5 sensor surface using amine coupling chemistry. The immobilised antibodies were then used to capture anti-FXII/FXIIa mAbs from solution.

Human FXII or FXIIa beta was then injected over captured antibody at various concentrations for detailed binding kinetics. Responses from a reference flow cell (in which mAb was not captured, but otherwise treated identically), were subtracted. The responses from a blank injection were then subtracted from the resultant sensorgrams.

The final corrected responses were fitted using non-linear regression to a model describing 1:1 kinetics, including a term for mass transport limitation. The Rmax value was fitted locally, to account for slight deviations in the level of mAb captured. Association rate (ka), dissociation rate (kd) and equilibrium dissociation constant (KD) were determined.

For detailed binding kinetics FXII was injected at 0, 15.1, 31.25, 62.5, 125, 250, and 500 nM, in duplicate and FXIIa beta was injected at 0, 1.25, 2.5, 5, 10, 20 and 40 nM, with 10 nM in duplicate.

For the 3F7 antibody, regeneration was performed after each cycle with a 90 second injection of 100 mM $H_3PO_4$. For mab OT-2, regeneration was performed after each cycle with a 60 second injection of 25 mM glycine, pH 1.7, followed by a 30 second injection of 25 mM glycine, pH 8.6. All assays were conducted at 25° C.

Example 5. Comparison of 3F7 with Other Antibody Inhibitors of FXIIa Amidolytic Activity A review of the relevant scientific literature revealed that although a number of antibodies have been described which can modulate FXII activity, the majority of these are either directed to the heavy chain and prevent the initial contact activation of FXII or are directed to the light chain and appear to only partially inhibit FXII amidolytic activity. The aim of this work was to compare 3F7 to antibody OT-2 which has been claimed to completely block the amidolytic activity of FXIIa (Dors et al., A novel sensitive assay for functional FXII based on the generation of kallikrein-C1-inhibitor complexes in FXII deficient plasma by glass-bound Factor XII. Thrombosis and Haemostasis, 1992, vol. 67, p. 644-648; Citarella et al., Structure/function analysis of human factor XII using recombinant deletion mutants. European Journal of Biochemistry, 1996, vol. 238, p. 240-249).

1) Inhibition of FXIIa Amidolytic Activity with 3F7 and OT-2 Antibodies

Figure 5:
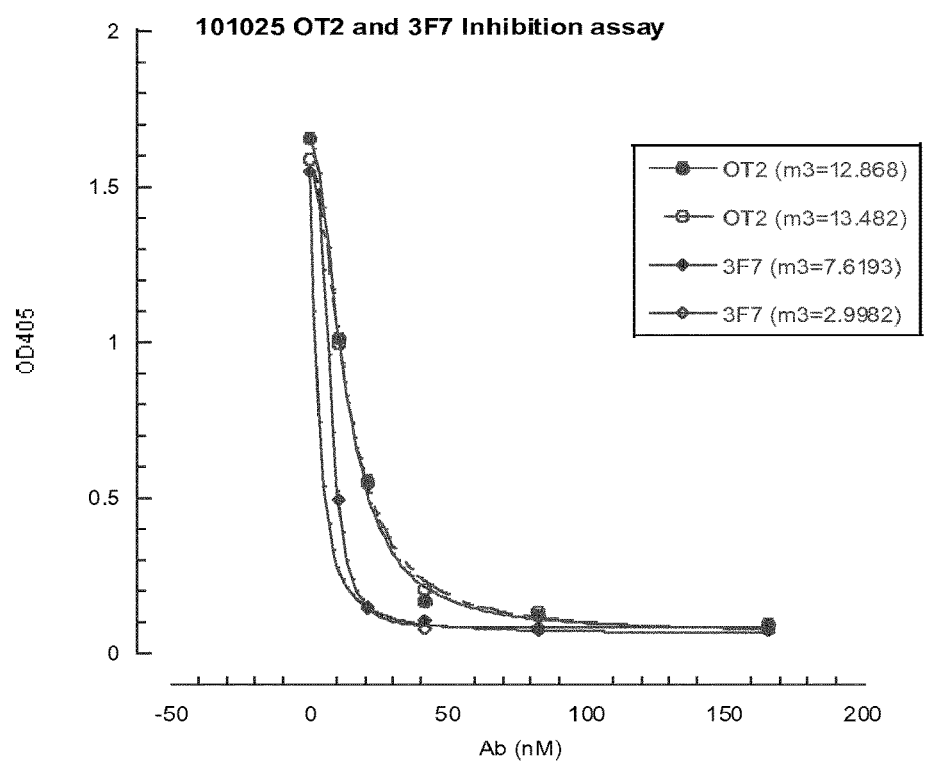
FIG. 5: Concentration-dependent inhibition of amidolytic activity of human FXIIa by monoclonal antibodies 3F7 and OT-2.

The activity of 3F7 and OT-2 antibodies was compared in an in vitro FXIIa amidolytic activity assay, essentially as described in Example 1(5). Both antibodies were able to completely block the amidolytic activity of FXIIa (FIG. 5).

2) Biacore Analysis of 3F7 and OT-2 mAbs Binding to FXII and Activated FXIIa Beta Whilst both 3F7 and OT-2 were shown to completely block the amidolytic activity of FXIIa, 3F7 showed a small but reproducible ~2-fold higher potency in this assay. To determine if 3F7 and OT-2 share a similar epitope on FXIIa we initially performed a competition ELISA with these antibodies and showed they were able to effectively compete with each other for binding to FXIIa (data not shown).

To further characterize the comparative binding of these antibodies to FXII we performed Biacore experiments with both antibodies against unactivated FXII and catalytically active FXIIa beta. The results of this experiment are shown in Table 7 and demonstrate that whilst OT-2 shows equivalent binding affinity to FXII or activated FXIIa beta, 3F7 shows a clear preference for binding to the activated form of FXII (FXIIa). These results show that whilst both antibodies appear to bind to similar regions on the light chain of FXII they do not appear to share an identical epitope. The ability of 3F7 to preferentially bind to activated FXII may confer a pharmokinetic and/or pharmacodynamic advantage.

TABLE 7

Detailed Biacore analysis of the binding affinity of the purified IgG monoclonal antibodies 3F7 and OT-2 to FXIIa beta.

| mAb | FXII KD (nM) | FXIIaβ KD (nM) |
|---|---|---|
| 3F7 | 121 ± 19 (N = 3) | 6.2 ± 0.2 (N = 3) |
| OT-2 | 0.69 ± 0.25 (N = 3) | 0.76 ± 0.077 (N = 3) |

Example 6: Identifying Key FXIIa Residues Involved in the Binding of 3F7

Figure 6:
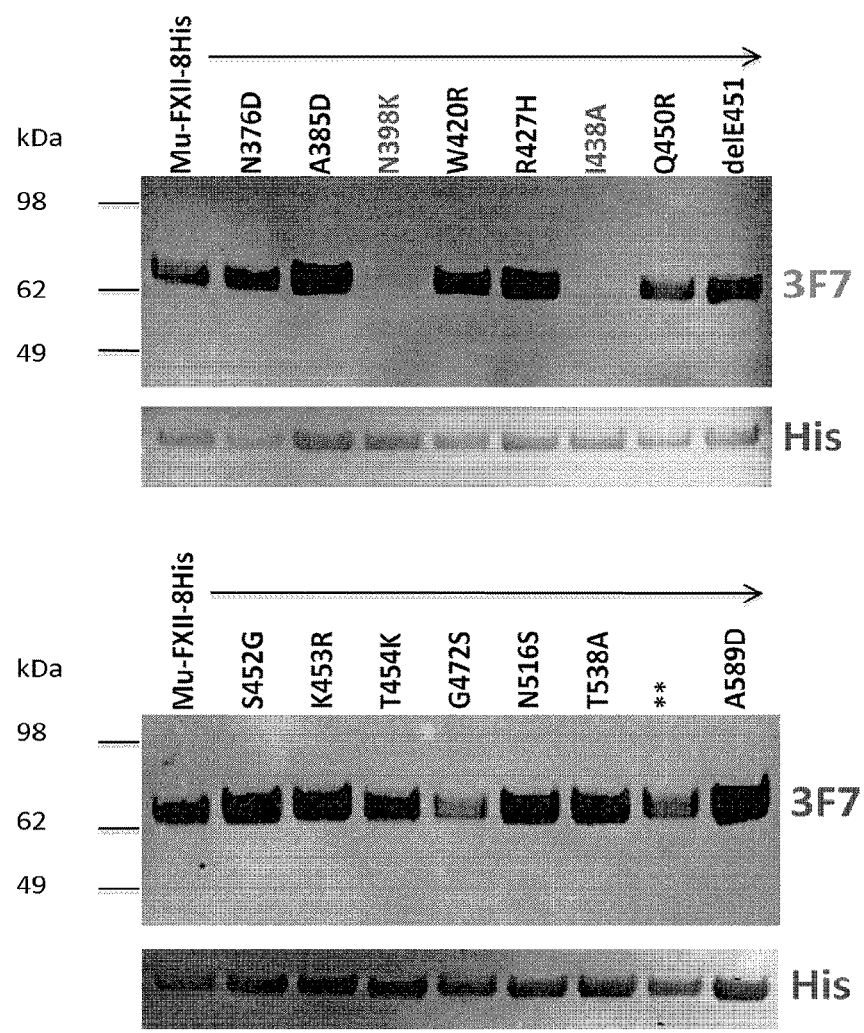
FIG. 6: A: Alignment of the catalytic domains of FXII of mouse (amino acids 355-597 of SEQ ID NO: 2), rat (amino acids 354-595 of SEQ ID NO: 3), and human (amino acids 373-615 of SEQ ID NO: 1), and identification of the residues that form the catalytic triad (*) and the mutations introduced (!) to identify the potential epitope of antibody 3F7. B: Western Blot showing the binding of 3F7 to the various mutants.

Having screened 3F7 for its ability to inhibit the activity of FXIIa from a number of species (data not shown), we determined 3F7 to be highly potent against mouse and human FXIIa, but not rat FXIIa. Using this information we investigated which key residues within the FXIIa light chain may be involved in the 3F7 epitope by generating a recombinant murine FXII (which is recognised by 3F7 using Western analysis) and mutating various residues that differed from the rat amino acid (see FIG. 6). As the result shows, mutating either position 398 or 438 abolishes the binding of 3F7.

1. Construction and Expression of Wild-Type and Mutant Murine Factor XII (Mu-FXII)

A cDNA encoding the entire Mu-FXII protein (GenBank Accession no. NM_021489) was obtained from GeneART AG (Regensberg, Germany). This cDNA was used as a template to make the following separate residue changes by standard PCR techniques: a) N376D, b) A385D, c) N398K, d) W420R, e) R427H, f) I438A, g) Q450R, h) delE451, i) S452G, j) K453R, T454K, k) G472S, l) N516S, m) T538A and n) A589D. With the exception of f) I438A, these residue changes corresponded to a switch from the mouse residue to its rat orthologue (GenBank Accession no. NM_001014006) (see FIG. 6A). In the case of h), this involved a deletion of Glu451. One further mutant (o) was generated, a multiple mutant involving the murine to rat amino acid changes E552D, T555V and A556T. All constructs were modified at the 3' end to encode a C-terminal 8×His-tag, cloned into the mammalian expression vector pcDNA3.1 (Invitrogen, Carlsbad, USA) and the sequence validated by DNA sequence analysis.

Freestyle™ 293 suspension cells (Invitrogen] were grown to $1.1 \times 10^6$ cells/ml in 5 ml Freestyle Expression media (Invitrogen). 7 µL 293Fectin (Invitrogen) transfection reagent was pre-incubated for 5 minutes with 167 µL Opti-MEM I medium (Invitrogen), then added to 5 µg plasmid DNA encoding wild-type or mutant Mu-FXII and the mixture incubated for a further 20 minutes. The DNA-293Fectin complex was added to the cells which were cultured for 6 days at 37° C., 8% $CO_2$ in a shaking incubator at 250 rpm. Culture supernatants were harvested by centrifugation at 2000 rpm for 5 minutes and stored at 4° C. for analysis.

2. Western Blotting

Supernatants containing recombinant wild-type or mutant mu-FXII were added to equal volumes of 2× non-reducing sample buffer, incubated at 80° C. for 10 minutes and then loaded onto pre-cast 4-12% Bis-Tris gels (Invitrogen) and electrophoresed for 1 hour at 200V. Proteins were then transferred electrophoretically onto nitrocellulose filters and blocked for 1 hour in 5% Milk powder in Tris-buffered saline with 0.05% Tween-20 (TTBS). Filters were then incubated for 1 hour with either 3F7 mAb or an anti-His mAb 3H3 (both at 1 mg/mL in TTBS with 5% Milk powder), washed thoroughly with TTBS, then incubated for a further hour with anti-human IgG-FITC or anti-mouse IgG-FITC, respectively (Millipore, USA; both at 0.25 mg/ml in TTBS with 5% Milk powder). Following further washing of membranes in TTBS, Ab-FITC bound proteins were visualized using a Typhoon variable mode analyzer (GE Healthcare, USA). The results are shown in FIG. 6B. The binding of 3F7 is abolished when residues 398 and 438 of the mouse sequence are mutated, indicating that these two residues may be part of the epitope of mAb 3F7.

Example 7: Prevention of $FeCl_3$-Induced Arterial Thrombosis in Mice with by Intravenous Treatment with Monoclonal Antibody 3F7

Previous studies (e.g. disclosed in WO2006066878) have shown that inhibition of FXIIa prevented $FeCl_3$-induced arterial thrombosis in mice. The goal of this study was to explore whether mice are also protected against arterial thrombosis by treatment with a specific monoclonal antibody directed against coagulation factor XIIa (MAb 3F7).

Methods

Treatment groups were as shown in Table 8:

TABLE 8

Treatment groups

| No. | Treatment | Dose/volume/schedule/route | N (f) |
|---|---|---|---|
| 1 | Isotonic saline | N.a.[1]/0.1 mL/20 g b.w./t = −15 min./i.v. | 25 |
| 2 | MAb 3F7 | 30 mg/kg/0.1 mL/20 g b.w./t = −15 min./i.v. | 10 |
| 3 | MAb 3F7 | 20 mg/kg/0.1 mL/20 g b.w./t = −15 min./i.v. | 5 |
| 4 | MAb 3F7 | 10 mg/kg/0.1 mL/20 g b.w./t = −15 min./i.v. | 10 |
| 5 | MAb 3F7 | 5 mg/kg/0.1 mL/20 g b.w./t = −15 min./i.v. | 10 |
| 6 | MAb 3F7 | 2.5 mg/kg/0.1 mL/20 g b.w./t = −15 min./i.v. | 10 |
| 7 | MAb 3F7 | 1 mg/kg/0.1 mL/20 g b.w./t = −15 min./i.v. | 10 |

TABLE 8-continued

| | | Treatment groups | |
|---|---|---|---|
| No. | Treatment | Dose/volume/schedule/route | N (f) |
| 8 | MAb 3F7 | 0.5 mg/kg/0.1 mL/20 g b.w./t = −15 min./i.v. | 10 |
| 9 | Control MAb | 30 mg/kg/0.2 mL/20 g b.w./t = −15 min./i.v. | 10 |

[1]N.a. = not applicable

Mice of strain NMRI, obtained from Charles River Laboratories, female, aged 6-8 weeks, weighing between 25 and 39 g, received a single i.v. injection of the treatment solution as listed in Table 8 at t=−15 min in deep anesthesia. Thereafter, the effects of the treatment on the thrombotic occlusion rate were quantified. Baseline blood flow was determined by placing an ultrasonic flow probe around the exposed arteria carotis. To initiate thrombosis, a 0.5 mm² (0.5×1.0 mm) patch of filter paper saturated with 10% ferric chloride solution was placed on the arteria carotis downstream from the flow probe at t=O min. After 3 minutes the filter paper was removed and blood flow was monitored for 60 minutes to determine the occurrence of thrombotic occlusions.

Following the 60 minutes observation period, blood samples were taken from study animals (anticoagulant: 10% citrate). Thereafter, plasma was prepared according to standard methods, and deep frozen (−80° C.±10° C.) until determination of aPTT (activated partial thromboplastin time), PT (prothrombin time) and FXIIa-activity.

Determination of the aPTT:

The aPTT was determined by adding 50 µL of study plasma samples (see above) to 50 µL Pathromtin SL (Siemens HealthCare Diagnostics Products GmbH, Marburg, Germany) followed by an incubation phase of 120 seconds at 37° C. Subsequently, 50 µL of a calcium chloride solution (25 mM, Siemens HealthCare Diagnostics Products GmbH, Marburg, Germany) was added to start the reaction.

Determination of the PT:

The PT was determined by adding 50 µL of study plasma samples (see above) to 100 µL of the activation reagent Thromborel S (Siemens HealthCare Diagnostics Products GmbH, Marburg, Germany) after 15 seconds incubation time at 37° C.

Determination of FXIIa-Activity:

The FXIIa-activity was determined by using an aPTT-based assay and compared to a reference curve obtained with dilutions of standard human plasma and FXII-deficient plasma (Siemens HealthCare Diagnostics Products GmbH, Marburg, Germany). 50 µL of the study plasma samples (see above), which were pre-diluted 1:5 with imidazol buffer solution (Siemens HealthCare Diagnostics Products GmbH, Marburg, Germany), were added to 50 µL of FXII-deficient plasma. After an incubation time of 30 seconds at 37° C., 50 µL Pathromtin SL (Siemens HealthCare Diagnostics Products GmbH, Marburg, Germany) was added and the solution thereafter incubated for 120 seconds at 37° C. Subsequently, 50 µL of a calcium chloride solution (25 mM, Siemens HealthCare Diagnostics Products GmbH, Marburg, Germany) was added to start the reaction.

All three analyses were performed in a BCT (Behring Coagulation Timer; Siemens HealthCare Diagnostics Products GmbH, Marburg, Germany) in line with the conditions suggested by the supplier of respective assay reagents (Siemens HealthCare Diagnostics Products GmbH, Marburg, Germany).

Figure 7:
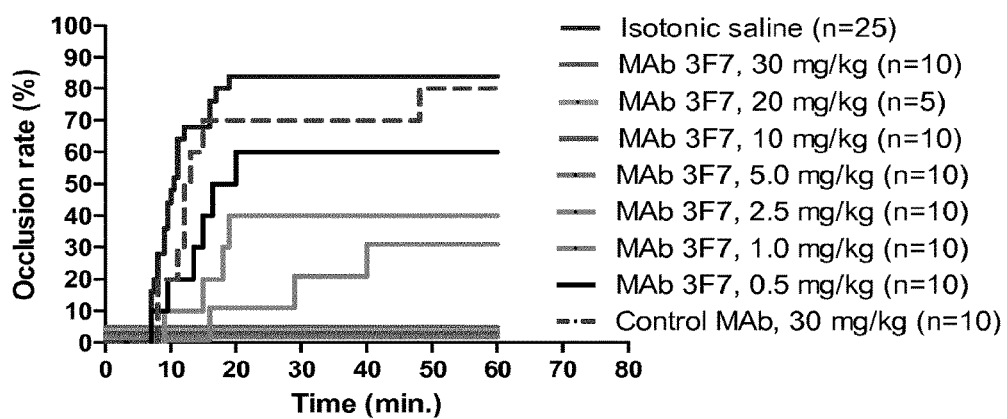
FIG. 7: Occlusion rate in $FeCl_3$-induced thrombosis following treatment with MAb 3F7 (n=5-25/group)
Figure 8:
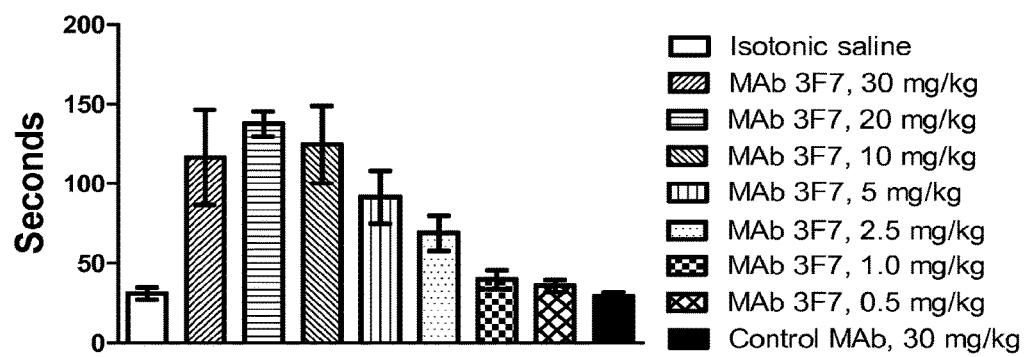
FIG. 8: Effect of MAb 3F7 on aPTT (n=5-25/group; mean±SD)
Figure 9:
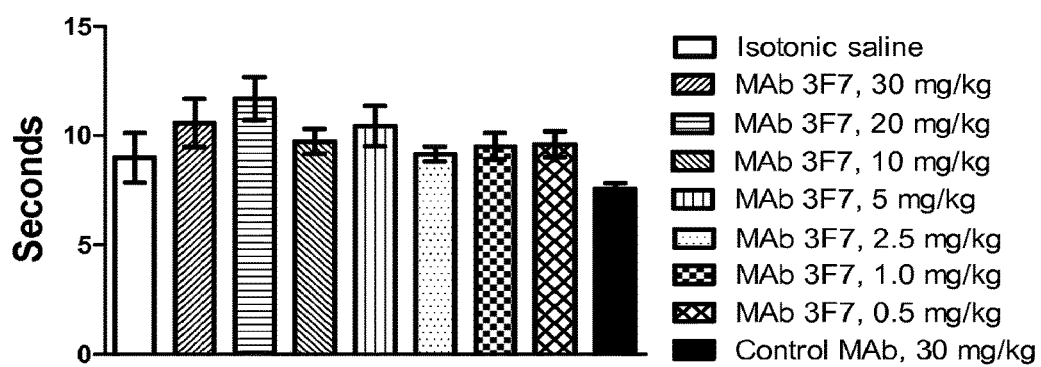
FIG. 9: Effect of MAb 3F7 on PT (n=5-25/group; mean±SD)
Figure 10:
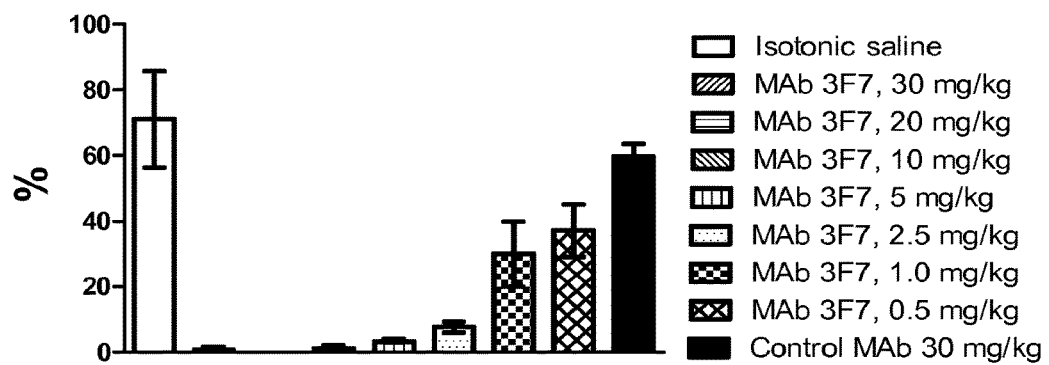
FIG. 10: Effect of MAb 3F7 on FXIIa-activity (n=5-25/group; mean±SD)
Figure 11:
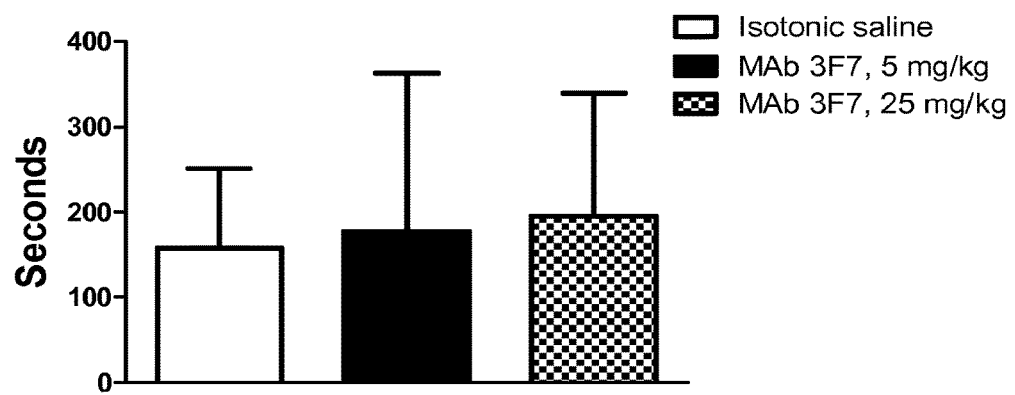
FIG. 11: Effect of MAb 3F7 on time to hemostasis. Data are presented as mean values (+SD). Statistics: $p>0.05$ (Kruskal-Wallis test). N=10/group.
Figure 12:
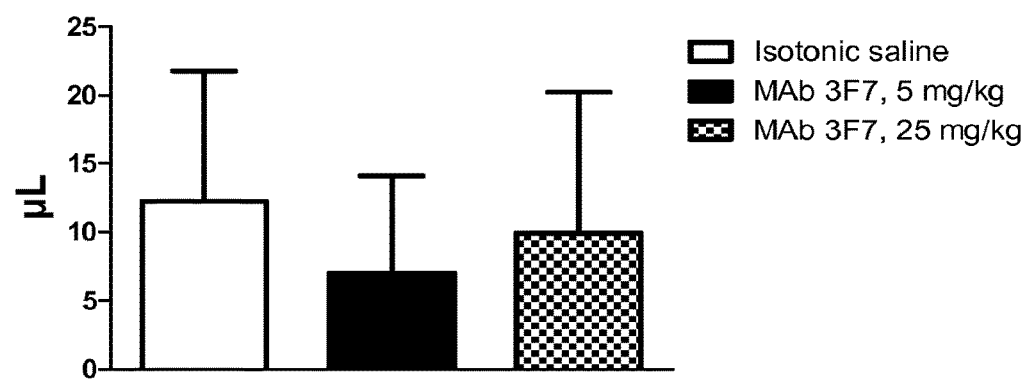
FIG. 12: Effect of MAb 3F7 on total blood loss. Data are presented as mean values (+SD). Statistics: $p>0.05$ (Kruskal-Wallis test). N=10/group.
Figure 13:
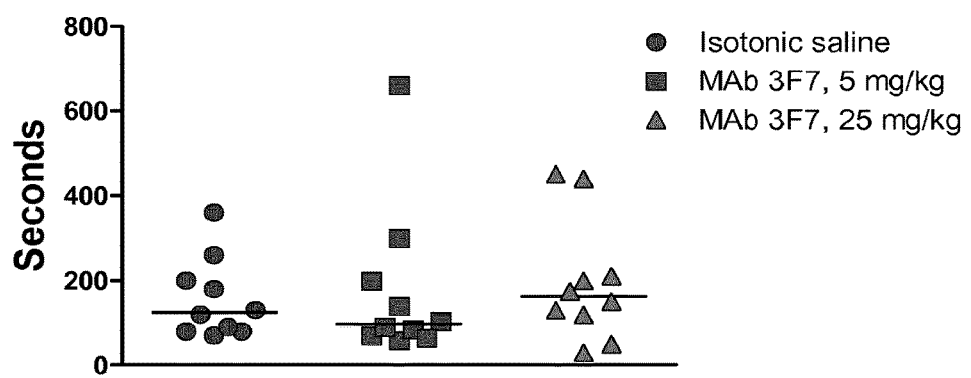
FIG. 13: Effect of MAb 3F7 on time to hemostasis. Horizontal lines represent median values. Statistics: $p>0.05$ (Kruskal-Wallis test). N=10/group.
Figure 14:
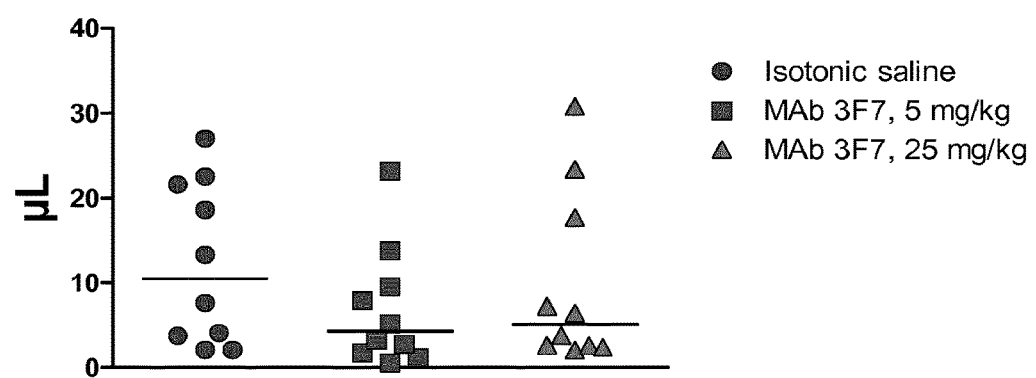
FIG. 14: Effect of MAb 3F7 on total blood loss. Horizontal lines represent median values. Statistics: $p>0.05$ (Kruskal-Wallis test). N=10/group.

Results:

Intravenous injection of 30 mg/kg, 20 mg/kg, 10 mg/kg and 5 mg/kg MAb 3F7 resulted in a complete protection from $FeCl_3$-induced occlusion of the arteria carotis of mice (Table 9, FIG. 7). At decreasing doses (i.e. 2.5-0.5 mg/kg), occlusion rates increased while times to occlusion decreased dose-dependently (Table 9, FIG. 7). Compared to controls, PT was unchanged (Table 10, FIG. 9) while aPTT was prolonged about fourfold at the high doses (Table 10, FIG. 8). FXIIa-activity was nearly completely inhibited at a dose of 10 mg/kg and above, and still halved at a dose of 0.5 mg/kg (Table 10, FIG. 10). Furthermore, aPTT decreased while FXIIa-activity increased dose-dependently at decreasing doses of the MAb 3F7 (Table 10, FIGS. 8 and 10). The control MAb showed no protection from $FeCl_3$-induced occlusion of the arteria carotis and aPTT, PT and FXIIa-activity values were unchanged (Tables 9, 10, FIGS. 7 to 10).

TABLE 9

| | Occlusion rates | |
|---|---|---|
| No. | Treatment | Occlusion rate |
| 1 | Isotonic saline | 21/25 (84%) |
| 2 | MAb 3F7 30 mg/kg | 0/10 (0%) |
| 3 | MAb 3F7 20 mg/kg | 0/5 (0%) |
| 4 | MAb 3F7 10 mg/kg | 0/10 (0%) |
| 5 | MAb 3F7 5 mg/kg | 0/10 (0%) |
| 6 | MAb 3F7 2.5 mg/kg | 3/10 (30%) |
| 7 | MAb 3F7 1 mg/kg | 4/10 (40%) |
| 8 | MAb 3F7 0.5 mg/kg | 6/10 (60%) |
| 9 | Control MAb 30 mg/kg | 8/10 (80%) |

TABLE 10

| | PT, aPTT and FXIIa-activity (mean ± SD) | | | |
|---|---|---|---|---|
| No. | Treatment | PT | aPTT | FXIIa-activity |
| 1 | Isotonic saline | 8.99 ± 1.13 | 31.19 ± 3.97 | 71.13 ± 14.64 |
| 2 | MAb 3F7 30 mg/kg | 10.58 ± 1.12 | 116.70 ± 29.96 | 0.63 ± 1.16 |
| 3 | MAb 3F7 20 mg/kg | 11.68 ± 0.98 | 137.90 ± 7.74 | 0.00 ± 0.00 |
| 4 | MAb 3F7 10 mg/kg | 9.74 ± 0.57 | 124.70 ± 24.41 | 0.94 ± 1.29 |
| 5 | MAb 3F7 5 mg/kg | 10.43 ± 0.92 | 91.72 ± 16.89 | 3.17 ± 0.92 |
| 6 | MAb 3F7 2.5 mg/kg | 9.14 ± 0.33 | 69.02 ± 11.05 | 7.68 ± 1.59 |
| 7 | MAb 3F7 1 mg/kg | 9.51 ± 0.61 | 39.84 ± 5.83 | 30.02 ± 10.00 |
| 8 | MAb 3F7 0.5 mg/kg | 9.61 ± 0.60 | 35.89 ± 3.73 | 37.22 ± 7.92 |
| 9 | Control MAb 30 mg/kg | 7.56 ± 0.28 | 29.33 ± 2.52 | 59.70 ± 12.54 |

Discussion:

This study demonstrated that mice were fully protected against arterial thrombosis after intravenous treatment with the MAb 3F7 at a dose of 5 mg/kg or higher. At decreasing doses, occlusion rates increased while times to occlusion decreased dose-dependently. Compared to controls, PT was unchanged while aPTT and FXIIa-activity were dose-dependently prolonged and decreased, respectively. In summary, MAb 3F7 demonstrated a remarkable efficacy profile and a desirable dose-response relationship.

Example 8: Effects of Anti-FXIIa Monoclonal Antibody 3F7 on Hemostasis in a Subaquatic Bleeding Model in Mice Example 7 had demonstrated that MAb 3F7 fully prevents FeCl$_3$-induced arterial thrombosis in mice at doses of 30-5 mg/kg. In addition to this effect, FXIIa-activity was nearly completely inhibited and aPTT prolonged up to fourfold at these protective doses. In order to clarify the question whether such effects may influence physiological hemostasis, the aim of this study is to investigate MAb 3F7 with regard to its effect on hemostasis in the murine tail tip bleeding model at the lowest fully protective dose (i.e. 5 mg/kg) as well as 5 fold beyond this dose (i.e. 25 mg/kg).

Methods

TABLE 11

Treatment groups

| No. | Treatment | Dose/volume/schedule/route | N (m/f) |
|---|---|---|---|
| 1 | Isotonic saline | N.a[1]./0.1 mL/20 g b.w./ t = −5 min./i.v. | 10 (0/10) |
| 2 | MAb 3F7 | 5 mg/kg/0.1 mL/20 g b.w./ t = −5 min./i.v. | 10 (0/10) |
| 3 | MAb 3F7 | 25 mg/kg/0.1 mL/20 g b.w./ t = −5 min./i.v. | 10 (0/10) |

[1]N.a = not applicable
Female NMRI mice were obtained from Charles River Laboratories (Kisslegg). They were 6 to 8 weeks old and weighed 25 to 32 g.

Hemostasis was determined in a subaquatic model. In brief, tail tip bleeding parameters were determined by quantifying time to hemostasis and blood loss. The volume of total blood loss was calculated by measuring the hemoglobin present in the saline used for submersion of the tail tip. The hemoglobin of the animals was taken into consideration accordingly. The tail tip cut was performed with a scalpel knife under deep anesthesia (Narcoren), removing about 3 mm of the tail tip. Immediately upon lesion, the tail tip was submerged in saline, which was kept at the physiological body temperature of the mice using a water bath. The observation period to monitor bleeding was 30 min. All test articles were administered i.v. at 5 min. prior to the start of the observation period (tail cut).

Results:
Independent of group, all animals showed hemostasis within the observation period (Table 12). Time to hemostasis and total blood loss did not differ between the groups (Tables 12 and 13, FIGS. 11 to 14; Kruskal-Wallis test: p>0.05).

TABLE 12

Frequency and Time to Hemostasis within 30 minutes following treatment with MAb 3F7 (n = 10/group)

| | | Time to hemostasis | | | |
|---|---|---|---|---|---|
| Treatment | Frequency of hemostasis | Mean ± SD (sec.) | Min. (sec.) | Med. (sec.) | Max. (sec.) |
| Isotonic saline | 10/10 (100%) | 157 ± 94 | 70 | 125 | 360 |
| MAb 3F7 5 mg/kg | 10/10 (100%) | 178 ± 185 | 60 | 98 | 660 |
| MAb 3F7 25 mg/kg | 10/10 (100%) | 196 ± 144 | 30 | 163 | 450 |

TABLE 13

Total blood loss following treatment with MAb 3F7 (n = 10/group)

| Treatment | | Mean ± SD (μL) | Min. (μL) | Median (μL) | Max. (μL) |
|---|---|---|---|---|---|
| Isotonic saline | | 12.3 ± 9.5 | 2.1 | 10.5 | 27.0 |
| MAb 3F7 | 5 mg/kg | 7.0 ± 7.1 | 0.6 | 4.2 | 23.3 |
| MAb 3F7 | 25 mg/kg | 9.9 ± 10.3 | 2.1 | 5.1 | 30.8 |

Discussion:
From the results of this study, it can be concluded that the two applied doses of MAb 3F7 (5 and 25 mg/kg), potently preventing FeCl$_3$-induced arterial thrombosis in mice, had no effects on physiological hemostasis using the murine tail tip bleeding model.

Example 9: Comparison of aPTT of 3F7 and Affinity-Matured Versions

The activated partial thromboplastin time (aPTT) was determined in standard human plasma (SHP, Dade Behring), where different amounts of the respective inhibitor were added into physiological saline to a total volume of 200 μL. 50 μL of this solution were added to 50 μL Pathromtin SL (Dade Behring) and incubated for 120 sec at 37° C. Subsequently, 50 μL of a calcium chloride solution (25 mM) were added to start the reaction.

The procedure was performed in a BCS XP (Behring Coagulation System) according to the conditions suggested by the manufacturer.

Figure 15:
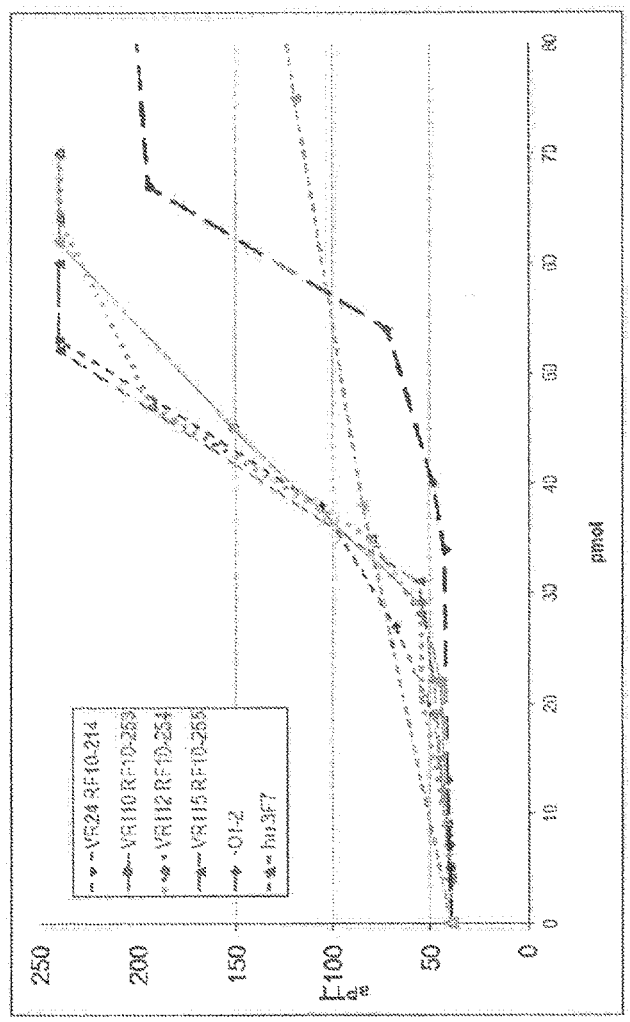
FIG. 15: Comparison of aPTT of OT-2, MAb 3F7 and affinity-matured versions of MAb 3F7

The aPTT of OT-2, MAb 3F7 and affinity-matured versions of MAb 3F7 was compared. The results are shown in FIG. 15. The affinity-matured versions of MAb 3F7 were significantly more active than OT-2 and the original MAb 3F7.

Figure 16:
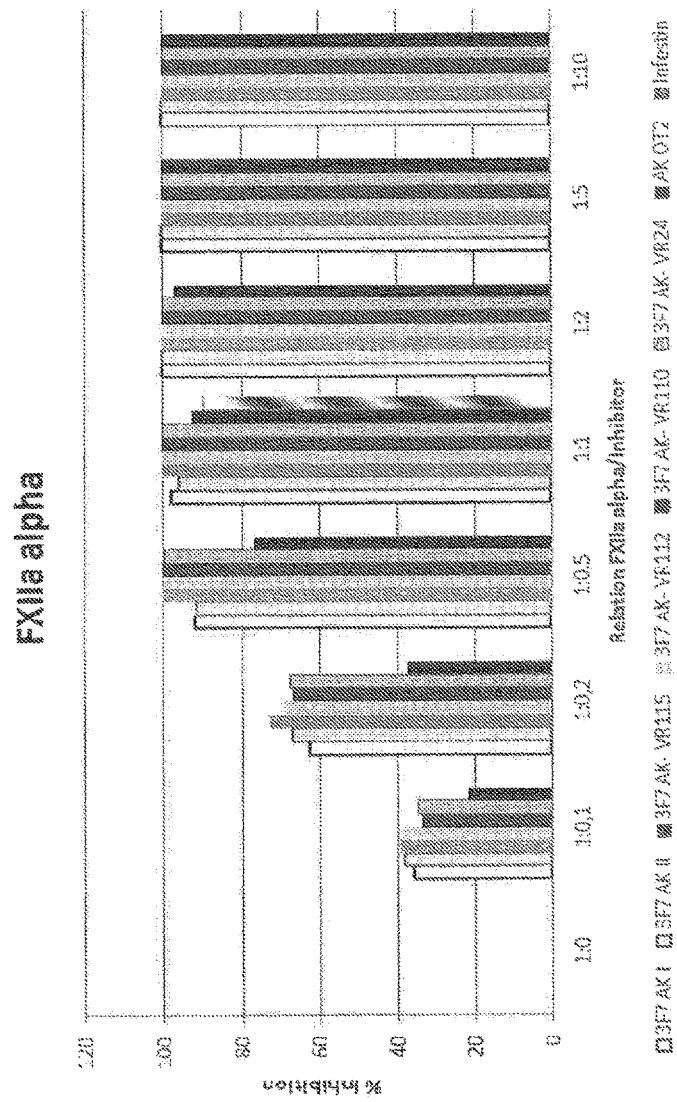
FIG. 16: Comparison of inhibition of human Factor XIIa-alpha by different antibodies

Example 10: Comparison of the Inhibition of Factor XIIa-Alpha by Different Antibodies An inhibition assay was performed, essentially as described in Example 1(5) above. In this case, 3F7, the affinity-matured 3F7 derivatives and OT-2 were compared in different molar ratios to human Factor XIIa-alpha, ranging from 1:0.1 to 1:10. The data are shown in Table 14 below and in FIG. 16. 3F7 and the affinity-matured derivatives showed better inhibition than OT-2, and a higher amount of OT-2 was required to achieve maximal inhibition than of 3F7 and derivatives thereof.

TABLE 14

| Antibody | Ratio FXIIa-alpha:Antibody | % Inhibition |
|---|---|---|
| 3F7 | 1:0.1 | 35.5 |
| | 1:0.2 | 62.5 |
| | 1:0.5 | 91.9 |
| | 1:1 | 97.9 |
| | 1:2 | 100 |
| | 1:5 | 100 |
| | 1:10 | 100 |
| 3F7 | 1:0.1 | 38.3 |
| | 1:0.2 | 66.8 |
| | 1:0.5 | 91.4 |
| | 1:1 | 96.1 |
| | 1:2 | 100 |
| | 1:5 | 100 |
| | 1:10 | 100 |

TABLE 14-continued

| Antibody | Ratio FXIIa-alpha:Antibody | % Inhibition |
|---|---|---|
| VR115 | 0.1:1 | 39.4 |
|  | 0.2:1 | 72.8 |
|  | 0.5:1 | 100 |
|  | 1:1 | 100 |
|  | 1:2 | 100 |
|  | 1:5 | 100 |
|  | 1:10 | 100 |
| VR112 | 0.1:1 | 39.9 |
|  | 0.2:1 | 68.7 |
|  | 0.5:1 | 99.7 |
|  | 1:1 | 100 |
|  | 2:1 | 100 |
|  | 5:1 | 100 |
|  | 10:1 | 100 |
| VR110 | 0.1:1 | 33.7 |
|  | 0.2:1 | 66.9 |
|  | 0.5:1 | 100 |
|  | 1:1 | 100 |
|  | 2:1 | 100 |
|  | 5:1 | 100 |
|  | 10:1 | 100 |
| VR24 | 0.1:1 | 34.5 |
|  | 0.2:1 | 67.3 |
|  | 0.5:1 | 99.7 |
|  | 1:1 | 100 |
|  | 2:1 | 100 |
|  | 5:1 | 100 |
|  | 10:1 | 100 |
| OT-2 | 0.1:1 | 21.6 |
|  | 0.2:1 | 37.7 |
|  | 0.5:1 | 76.6 |
|  | 1:1 | 92.7 |
|  | 2:1 | 96.9 |
|  | 5:1 | 100 |
|  | 10:1 | 100 |
| Infestin control | 1:1 | 90.0 |

The invention claimed is:

1. A method of treating venous, arterial, or capillary thrombus formation; thrombus formation in the heart; thromboembolism; thrombus formation during and/or after contacting blood with artificial surfaces; or intraluminal thrombi in a subject in need thereof, the method comprising administering to the subject an effective amount of an anti-Factor XII/XIIa monoclonal antibody or antigen-binding fragment thereof comprising an immunoglobulin heavy chain variable (vH) region and an immunoglobulin light chain variable (vL) region, wherein the vH region comprises:
a heavy chain CDR1 consisting of the sequence of SEQ ID NO: 6;
a heavy chain CDR2 consisting of the sequence of GIX$_1$X$_2$X$_3$X$_4$X$_5$X$_6$TVYADSVKG (SEQ ID NO: 8), wherein X$_1$ is R, N, or D; X$_2$ is P, V, I, or M; X$_3$ is 5, P, or A; X$_4$ is G, L, V, or T; X$_5$ can be any amino acid; and X$_6$ is T, G, or S; and
a heavy chain CDR3 consisting of the sequence of ALPRSGYLX$_1$X$_2$X$_3$X$_4$YYYYALDV (SEQ ID NO: 10), wherein X$_1$ is I, M, or V; X$_2$ is S or K; X$_3$ is P, K, T, or H; and X$_4$ is H, N, G, or Q; and wherein the vL region comprises:
a light chain CDR1 consisting of the sequence set forth in any one of SEQ ID NOs: 11 and 44-51;
a light chain CDR2 consisting of the sequence of SEQ ID NO: 12; and
a light chain CDR3 consisting of the sequence of AX$_1$WX$_2$X$_3$X$_4$X$_5$RX$_6$X$_7$ (SEQ ID NO: 14), wherein X$_1$ is A or S; X$_5$ is L or V; X$_6$ is G, L, or K; and X$_2$, X$_3$, X$_4$ and X$_7$ can be any amino acid.

2. The method of claim 1, wherein the subject suffers from venous or arterial thrombus formation selected from stroke, myocardial infarction, deep vein thrombosis, portal vein thrombosis, thromboembolism, renal vein thrombosis, jugular vein thrombosis, cerebral venous sinus thrombosis, Budd-Chiari syndrome, and Paget-Schroetter disease.

3. The method of claim 1, wherein the subject suffers from thrombus formation during and/or after contacting blood of the subject with one or more artificial surfaces during and/or after a medical procedure performed on said subject, wherein the anti-Factor XII/XIIa monoclonal antibody or antigen-binding fragment thereof is administered before and/or during and/or after said medical procedure, and wherein
(i) the artificial surface is exposed to at least 80% of the blood volume of the subject and the artificial surface is at least 0.2 m$^2$,
(ii) the artificial surface is a container for collection of blood outside the body of the subject, or
(iii) the artificial surface is a stent, valve, intraluminal catheter, or a system for internal assisted pumping of blood.

4. The method of claim 1, wherein the vH region comprises an amino acid sequence more than 85% identical to the sequence of SEQ ID NO: 4.

5. The method of claim 1, wherein the vL region comprises an amino acid sequence more than 85% identical to the sequence of SEQ ID NO: 5.

6. The method of claim 1, wherein the heavy chain CDR2 consists of the sequence set forth in any one of SEQ ID NOs: 7 and 29-38.

7. The method of claim 1, wherein the heavy chain CDR3 consists of the sequence set forth in any one of SEQ ID NOs: 9 and 39-43.

8. The method of claim 1, wherein
X$_5$ is G, Y, Q, K, R, N, or M in the heavy chain CDR2;
X$_2$ is D, Y, E, T, W, E, or S in the light chain CDR3;
X$_3$ is A, N, I, L, V, P, Q, or E in the light chain CDR3;
X$_4$ is S, D, P, E, Q, or R in the light chain CDR3; and/or
X$_7$ is V, A, D, T, M, or G in the light chain CDR3.

9. The method of claim 1, wherein the light chain CDR3 consists of the sequence set forth in any one of SEQ ID NOs: 13 and 52-63.

10. The method of claim 1, wherein the vH region comprises a heavy chain CDR1 consisting of the sequence of SEQ ID NO: 6, a heavy chain CDR2 consisting of the sequence of SEQ ID NO: 7, a heavy chain CDR3 consisting of the sequence of SEQ ID NO: 9, and wherein the vL region comprises a light chain CDR1 consisting of the sequence of SEQ ID NO: 11, a light chain CDR2 consisting of the sequence of SEQ ID NO: 12, and a light chain CDR3 consisting of the sequence of SEQ ID NO: 13.

11. The method of claim 1, wherein the vH region consists of the sequence of SEQ ID NO: 4, and wherein the vL region consists of the sequence of SEQ ID NO: 5.

12. The method of claim 1, wherein the vH region comprises a heavy chain CDR1 consisting of the sequence of SEQ ID NO: 6, a heavy chain CDR2 consisting of the sequence of SEQ ID NO: 29, a heavy chain CDR3 consisting of the sequence of SEQ ID NO: 9, and wherein the vL region comprises a light chain CDR1 consisting of the sequence of SEQ ID NO: 11, a light chain CDR2 consisting of the sequence of SEQ ID NO: 12, and a light chain CDR3 consisting of the sequence of SEQ ID NO: 13.

13. The method of claim 1, wherein the vH region comprises a heavy chain CDR1 consisting of the sequence of SEQ ID NO: 6, a heavy chain CDR2 consisting of the sequence of SEQ ID NO: 30, a heavy chain CDR3 consisting of the sequence of SEQ ID NO: 9, and wherein the vL region comprises a light chain CDR1 consisting of the sequence of SEQ ID NO: 11, a light chain CDR2 consisting of the sequence of SEQ ID NO: 12, and a light chain CDR3 consisting of the sequence of SEQ ID NO: 13.

14. The method of claim 1, wherein the vH region comprises a heavy chain CDR1 consisting of the sequence of SEQ ID NO: 6, a heavy chain CDR2 consisting of the sequence of SEQ ID NO: 31, a heavy chain CDR3 consisting of the sequence of SEQ ID NO: 9, and wherein the vL region comprises a light chain CDR1 consisting of the sequence of SEQ ID NO: 11, a light chain CDR2 consisting of the sequence of SEQ ID NO: 12, and a light chain CDR3 consisting of the sequence of SEQ ID NO: 13.

15. The method of claim 1, wherein the vH region comprises a heavy chain CDR1 consisting of the sequence of SEQ ID NO: 6, a heavy chain CDR2 consisting of the sequence of SEQ ID NO: 32, a heavy chain CDR3 consisting of the sequence of SEQ ID NO: 9, and wherein the vL region comprises a light chain CDR1 consisting of the sequence of SEQ ID NO: 11, a light chain CDR2 consisting of the sequence of SEQ ID NO: 12, and a light chain CDR3 consisting of the sequence of SEQ ID NO: 13.

16. The method of claim 1, wherein the vH region comprises a heavy chain CDR1 consisting of the sequence of SEQ ID NO: 6, a heavy chain CDR2 consisting of the sequence of SEQ ID NO: 7, a heavy chain CDR3 consisting of the sequence of SEQ ID NO: 9, and wherein the vL region comprises a light chain CDR1 consisting of the sequence of SEQ ID NO: 44, a light chain CDR2 consisting of the sequence of SEQ ID NO: 12, and a light chain CDR3 consisting of the sequence of SEQ ID NO: 13.

17. The method of claim 1, wherein the antibody or antigen-binding fragment thereof has a more than 2 fold higher binding affinity to human Factor XIIa-beta than to human Factor XII and is capable of inhibiting the amidolytic activity of human Factor XIIa at a concentration of 100 nM or lower in an in vitro amidolytic activity assay by 80% or more.

18. The method of claim 1, wherein the antibody or antigen-binding fragment thereof inhibits the amidolytic activity of Factor XIIa-alpha by more than 50% in an in vitro amidolytic activity assay when used at a molar ratio of FXIIa-alpha to antibody of 1:0.2.

19. The method of claim 1, wherein the antibody or antigen-binding fragment thereof binds murine FXII/FXIIa; and wherein the antibody or antigen-binding fragment thereof binds to a polypeptide comprising the sequence of SEQ ID NO: 2 in which (a) the asparagine residue at position 398 of SEQ ID NO: 2 is substituted for lysine; or (b) the isoleucine residue at position 438 of SEQ ID NO: 2 is substituted for alanine, and wherein the affinity of the antibody or antigen-binding fragment thereof for the polypeptide in (a) or (b) is lower than the affinity of the antibody or antigen-binding fragment thereof for a polypeptide comprising SEQ ID NO: 2 without the corresponding substitution.

20. The method of claim 1, wherein the antibody or antigen-binding fragment thereof binds human Factor XIIa-beta with a $K_D$ of better than $10^{-7}$M.

21. The method of claim 1, wherein the antibody or antigen-binding fragment thereof competes with Infestin for binding to human Factor XIIa-beta.

22. The method of claim 1, wherein the antibody or antigen-binding fragment thereof is a human IgG or variant thereof.

23. The method of claim 22, wherein the IgG is IgG4.

* * * * *

SEQUENCE LISTING

<160> NUMBER OF SEQ ID NOS: 77

<210> SEQ ID NO 1
<211> LENGTH: 615
<212> TYPE: PRT
<213> ORGANISM: Homo sapiens

<400> SEQUENCE: 1

Met Arg Ala Leu Leu Leu Gly Phe Leu Leu Val Ser Leu Glu Ser
1               5                   10                  15

Thr Leu Ser Ile Pro Pro Trp Glu Ala Pro Lys Glu His Lys Tyr Lys
            20                  25                  30

Ala Glu Glu His Thr Val Val Leu Thr Val Thr Gly Glu Pro Cys His
        35                  40                  45

Phe Pro Phe Gln Tyr His Arg Gln Leu Tyr His Lys Cys Thr His Lys
    50                  55                  60

Gly Arg Pro Gly Pro Gln Pro Trp Cys Ala Thr Thr Pro Asn Phe Asp
65                  70                  75                  80

Gln Asp Gln Arg Trp Gly Tyr Cys Leu Glu Pro Lys Lys Val Lys Asp
                85                  90                  95

His Cys Ser Lys His Ser Pro Cys Gln Lys Gly Gly Thr Cys Val Asn
            100                 105                 110

Met Pro Ser Gly Pro His Cys Leu Cys Pro Gln His Leu Thr Gly Asn
        115                 120                 125

His Cys Gln Lys Glu Lys Cys Phe Glu Pro Gln Leu Leu Arg Phe Phe
    130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Ala Phe
        195                 200                 205

Cys Asp Val Asp Thr Lys Ala Ser Cys Tyr Asp Gly Arg Gly Leu Ser
    210                 215                 220

Tyr Arg Gly Leu Ala Arg Thr Thr Leu Ser Gly Ala Pro Cys Gln Pro

```
                225                 230                 235                 240
        Trp Ala Ser Glu Ala Thr Tyr Arg Asn Val Thr Ala Glu Gln Ala Arg
                        245                 250                 255

Asn Trp Gly Leu Gly Gly His Ala Phe Cys Arg Asn Pro Asp Asn Asp
                        260                 265                 270

Ile Arg Pro Trp Cys Phe Val Leu Asn Arg Asp Arg Leu Ser Trp Glu
                        275                 280                 285

Tyr Cys Asp Leu Ala Gln Cys Gln Thr Pro Thr Gln Ala Ala Pro Pro
                        290                 295                 300

Thr Pro Val Ser Pro Arg Leu His Val Pro Leu Met Pro Ala Gln Pro
        305                 310                 315                 320

Ala Pro Pro Lys Pro Gln Pro Thr Thr Arg Thr Pro Gln Ser Gln
                        325                 330                 335

Thr Pro Gly Ala Leu Pro Ala Lys Arg Glu Gln Pro Pro Ser Leu Thr
                        340                 345                 350

Arg Asn Gly Pro Leu Ser Cys Gly Gln Arg Leu Arg Lys Ser Leu Ser
                        355                 360                 365

Ser Met Thr Arg Val Val Gly Gly Leu Val Ala Leu Arg Gly Ala His
                370                 375                 380

Pro Tyr Ile Ala Ala Leu Tyr Trp Gly His Ser Phe Cys Ala Gly Ser
        385                 390                 395                 400

Leu Ile Ala Pro Cys Trp Val Leu Thr Ala Ala His Cys Leu Gln Asp
                        405                 410                 415

Arg Pro Ala Pro Glu Asp Leu Thr Val Val Leu Gly Gln Glu Arg Arg
                        420                 425                 430

Asn His Ser Cys Glu Pro Cys Gln Thr Leu Ala Val Arg Ser Tyr Arg
                        435                 440                 445

Leu His Glu Ala Phe Ser Pro Val Ser Tyr Gln His Asp Leu Ala Leu
                        450                 455                 460

Leu Arg Leu Gln Glu Asp Ala Asp Gly Ser Cys Ala Leu Leu Ser Pro
        465                 470                 475                 480

Tyr Val Gln Pro Val Cys Leu Pro Ser Gly Ala Ala Arg Pro Ser Glu
                        485                 490                 495

Thr Thr Leu Cys Gln Val Ala Gly Trp Gly His Gln Phe Glu Gly Ala
                        500                 505                 510

Glu Glu Tyr Ala Ser Phe Leu Gln Glu Ala Gln Val Pro Phe Leu Ser
                        515                 520                 525

Leu Glu Arg Cys Ser Ala Pro Asp Val His Gly Ser Ser Ile Leu Pro
        530                 535                 540

Gly Met Leu Cys Ala Gly Phe Leu Glu Gly Gly Thr Asp Ala Cys Gln
        545                 550                 555                 560

Gly Asp Ser Gly Gly Pro Leu Val Cys Glu Asp Gln Ala Ala Glu Arg
                        565                 570                 575

Arg Leu Thr Leu Gln Gly Ile Ile Ser Trp Gly Ser Gly Cys Gly Asp
                        580                 585                 590

Arg Asn Lys Pro Gly Val Tyr Thr Asp Val Ala Tyr Tyr Leu Ala Trp
                        595                 600                 605

Ile Arg Glu His Thr Val Ser
                610                 615

<210> SEQ ID NO 2
<211> LENGTH: 597
<212> TYPE: PRT
<213> ORGANISM: Mus musculus
```

<400> SEQUENCE: 2

Met Thr Ala Leu Leu Phe Leu Gly Ser Leu Leu Met Ser Leu Asp Leu
1               5                   10                  15

Thr Leu Ser Ala Pro Pro Trp Lys Asp Ser Lys Lys Phe Lys Asp Ala
            20                  25                  30

Pro Asp Gly Pro Thr Val Val Leu Thr Val Asp Gly Arg Leu Cys His
        35                  40                  45

Phe Pro Phe Gln Tyr His Arg Gln Leu His His Lys Cys Ile His Lys
    50                  55                  60

Arg Arg Pro Gly Ser Arg Pro Trp Cys Ala Thr Thr Pro Asn Phe Asp
65              70                  75                  80

Glu Asp Gln Gln Trp Gly Tyr Cys Leu Glu Pro Lys Lys Val Lys Asp
                85                  90                  95

His Cys Ser Lys His Asn Pro Cys His Lys Gly Gly Thr Cys Ile Asn
            100                 105                 110

Thr Pro Asn Gly Pro His Cys Leu Cys Pro Glu His Leu Thr Gly Lys
        115                 120                 125

His Cys Gln Lys Glu Lys Cys Phe Glu Pro Gln Leu Leu Lys Phe Phe
130                 135                 140

His Glu Asn Glu Leu Trp Phe Arg Thr Gly Pro Gly Gly Val Ala Arg
145                 150                 155                 160

Cys Glu Cys Lys Gly Ser Glu Ala His Cys Lys Pro Val Ala Ser Gln
                165                 170                 175

Ala Cys Ser Ile Asn Pro Cys Leu Asn Gly Gly Ser Cys Leu Leu Val
            180                 185                 190

Glu Asp His Pro Leu Cys Arg Cys Pro Thr Gly Tyr Thr Gly Tyr Phe
        195                 200                 205

Cys Asp Leu Asp Leu Trp Ala Thr Cys Tyr Glu Gly Arg Gly Leu Ser
    210                 215                 220

Tyr Arg Gly Gln Ala Gly Thr Thr Gln Ser Gly Ala Pro Cys Gln Arg
225                 230                 235                 240

Trp Thr Val Glu Ala Thr Tyr Arg Asn Met Thr Glu Lys Gln Ala Leu
                245                 250                 255

Ser Trp Gly Leu Gly His His Ala Phe Cys Arg Asn Pro Asp Asn Asp
            260                 265                 270

Thr Arg Pro Trp Cys Phe Val Trp Ser Gly Asp Arg Leu Ser Trp Asp
        275                 280                 285

Tyr Cys Gly Leu Glu Gln Cys Gln Thr Pro Thr Phe Ala Pro Leu Val
    290                 295                 300

Val Pro Glu Ser Gln Glu Glu Ser Pro Ser Gln Ala Pro Ser Leu Ser
305                 310                 315                 320

His Ala Pro Asn Asp Ser Thr Asp His Gln Thr Ser Leu Ser Lys Thr
                325                 330                 335

Asn Thr Met Gly Cys Gly Gln Arg Phe Arg Lys Gly Leu Ser Ser Phe
            340                 345                 350

Met Arg Val Val Gly Gly Leu Val Ala Leu Pro Gly Ser His Pro Tyr
        355                 360                 365

Ile Ala Ala Leu Tyr Trp Gly Asn Asn Phe Cys Ala Gly Ser Leu Ile
    370                 375                 380

Ala Pro Cys Trp Val Leu Thr Ala Ala His Cys Leu Gln Asn Arg Pro
385                 390                 395                 400

Ala Pro Glu Glu Leu Thr Val Val Leu Gly Gln Asp Arg His Asn Gln

```
            405                 410                 415
Ser Cys Glu Trp Cys Gln Thr Leu Ala Val Arg Ser Tyr Arg Leu His
            420                 425                 430

Glu Gly Phe Ser Ser Ile Thr Tyr Gln His Asp Leu Ala Leu Leu Arg
            435                 440                 445

Leu Gln Glu Ser Lys Thr Asn Ser Cys Ala Ile Leu Ser Pro His Val
450                 455                 460

Gln Pro Val Cys Leu Pro Ser Gly Ala Pro Pro Ser Glu Thr Val
465                 470                 475                 480

Leu Cys Glu Val Ala Gly Trp Gly His Gln Phe Glu Gly Ala Glu Glu
                485                 490                 495

Tyr Ser Thr Phe Leu Gln Glu Ala Gln Val Pro Phe Ile Ala Leu Asp
            500                 505                 510

Arg Cys Ser Asn Ser Asn Val His Gly Asp Ala Ile Leu Pro Gly Met
            515                 520                 525

Leu Cys Ala Gly Phe Leu Glu Gly Gly Thr Asp Ala Cys Gln Gly Asp
            530                 535                 540

Ser Gly Gly Pro Leu Val Cys Glu Glu Gly Thr Ala Glu His Gln Leu
545                 550                 555                 560

Thr Leu Arg Gly Val Ile Ser Trp Gly Ser Gly Cys Gly Asp Arg Asn
                565                 570                 575

Lys Pro Gly Val Tyr Thr Asp Val Ala Asn Tyr Leu Ala Trp Ile Gln
            580                 585                 590

Lys His Ile Ala Ser
            595

<210> SEQ ID NO 3
<211> LENGTH: 595
<212> TYPE: PRT
<213> ORGANISM: Rattus norvegicus

<400> SEQUENCE: 3

Met Thr Ala Leu Leu Phe Leu Gly Ser Leu Leu Met Ser Leu Asp Leu
1               5                   10                  15

Thr Leu Ser Ala Pro Pro Trp Lys Ser Lys Glu Phe Lys Asp Gly Ala
            20                  25                  30

Gly Asp Pro Ser Val Val Leu Thr Val Asp Gly Lys Leu Cys His Phe
        35                  40                  45

Pro Phe Gln Tyr His Arg Arg Leu Tyr His Lys Cys Ile His Lys Gly
    50                  55                  60

Gln Pro Gly Ser Arg Pro Trp Cys Ala Thr Thr Pro Asn Phe Asp Glu
65                  70                  75                  80

Asp Gln Gln Trp Gly Tyr Cys Leu Glu Pro Lys Lys Val Lys Asp His
                85                  90                  95

Cys Ser Lys His Ser Pro Cys His Lys Gly Gly Thr Cys Val Asn Thr
            100                 105                 110

Pro Asn Gly Pro His Cys Leu Cys Pro Glu His Leu Thr Gly Lys His
        115                 120                 125

Cys Gln Arg Glu Lys Cys Phe Glu Ser Gln Leu Leu Lys Phe Phe His
    130                 135                 140

Glu Asn Glu Ile Trp Phe Arg Thr Gly Pro Gly Gly Val Ala Arg Cys
145                 150                 155                 160

Gln Cys Lys Gly Pro Gln Ala Val Cys Lys Leu Leu Thr Ser Gln Val
                165                 170                 175
```

```
Cys Arg Val Asn Pro Cys Leu Asn Gly Gly Thr Cys Leu Leu Val Glu
            180                 185                 190
Asp His Arg Leu Cys His Cys Pro Ala Gly Tyr Ala Gly Pro Phe Cys
            195                 200                 205
Asp Leu Asp Leu Lys Ala Thr Cys Tyr Glu Asp Arg Gly Leu Ser Tyr
            210                 215                 220
Arg Gly Gln Ala Lys Thr Thr Leu Ser Gly Ala Pro Cys Gln Arg Trp
225                 230                 235                 240
Ala Ser Glu Ala Thr Tyr Arg Asn Met Thr Glu Thr Gln Ala Leu Ser
            245                 250                 255
Trp Gly Leu Gly His His Ala Phe Cys Arg Asn Pro Asp Asn Asp Thr
            260                 265                 270
Arg Pro Trp Cys Tyr Val Trp Ser Gly Asp Arg Leu Ser Trp Asp Tyr
            275                 280                 285
Cys Asp Leu Glu Gln Cys Gln Met Pro Thr Leu Thr Ser Pro Val Ser
            290                 295                 300
Pro Glu Ser His Asp Met Leu Lys Pro Arg Pro Pro Ile Leu Gln Ser
305                 310                 315                 320
Ser Pro Arg Asp Ser Thr Arg Asn Gln Asn Val Val Ser Arg Thr Ser
            325                 330                 335
Thr Val Val Cys Gly Gln Arg Phe Arg Lys Arg Leu Ser Ser Leu Arg
            340                 345                 350
Arg Val Val Gly Gly Leu Val Ala Leu Pro Gly Ser His Pro Tyr Ile
            355                 360                 365
Ala Ala Leu Tyr Trp Gly Asp Ser Phe Cys Ala Gly Ser Leu Ile Asp
            370                 375                 380
Pro Cys Trp Val Leu Thr Ala Ala His Cys Leu Gln Lys Arg Pro Ala
385                 390                 395                 400
Pro Glu Glu Leu Thr Val Val Leu Gly Gln Asp Arg His Asn Gln Ser
            405                 410                 415
Cys Glu Arg Cys Gln Thr Leu Ala Val His Ser Tyr Arg Leu His Glu
            420                 425                 430
Gly Phe Ser Ser Lys Thr Tyr Gln His Asp Leu Ala Leu Leu Arg Leu
            435                 440                 445
Arg Gly Arg Lys Asn Ser Cys Ala Ile Leu Ser Pro His Val Gln Pro
450                 455                 460
Val Cys Leu Pro Ser Ser Ala Ala Pro Pro Ser Glu Thr Val Leu Cys
465                 470                 475                 480
Glu Val Ala Gly Trp Gly His Gln Phe Glu Gly Ala Glu Glu Tyr Ala
            485                 490                 495
Thr Phe Leu Gln Glu Ala Gln Val Pro Phe Ile Ser Leu Asp Arg Cys
            500                 505                 510
Ser Ser Ser Asn Val His Gly Asp Ala Ile Leu Pro Gly Met Leu Cys
            515                 520                 525
Ala Gly Phe Leu Glu Gly Gly Ala Asp Ala Cys Gln Gly Asp Ser Gly
            530                 535                 540
Gly Pro Leu Val Cys Asp Glu Gly Val Thr Glu Arg Gln Leu Thr Leu
545                 550                 555                 560
Arg Gly Val Ile Ser Trp Gly Ser Gly Cys Gly Asp Arg Asn Lys Pro
            565                 570                 575
Gly Val Tyr Thr Asp Val Ala Asn Tyr Leu Asp Trp Ile Gln Glu His
            580                 585                 590
Thr Ala Phe
```

-continued

```
                595

<210> SEQ ID NO 4
<211> LENGTH: 129
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Arg Pro Ser Gly Gly Thr Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser

<210> SEQ ID NO 5
<211> LENGTH: 110
<212> TYPE: PRT
<213> ORGANISM: Homo sapiens

<400> SEQUENCE: 5

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly
            100                 105                 110

<210> SEQ ID NO 6
<211> LENGTH: 5
<212> TYPE: PRT
<213> ORGANISM: Homo sapiens

<400> SEQUENCE: 6

Lys Tyr Ile Met Gln
1               5

<210> SEQ ID NO 7
<211> LENGTH: 17
```

```
<212> TYPE: PRT
<213> ORGANISM: Homo sapiens

<400> SEQUENCE: 7

Gly Ile Arg Pro Ser Gly Gly Thr Thr Val Tyr Ala Asp Ser Val Lys
1               5                   10                  15

Gly

<210> SEQ ID NO 8
<211> LENGTH: 17
<212> TYPE: PRT
<213> ORGANISM: Artificial
<220> FEATURE:
<223> OTHER INFORMATION: Heavy chain CDR2 showing variations
<220> FEATURE:
<221> NAME/KEY: V-segment
<222> LOCATION: (3)..(3)
<223> OTHER INFORMATION: Xaa is selected from Arg, Asn, and Asp
<220> FEATURE:
<221> NAME/KEY: V-segment
<222> LOCATION: (4)..(4)
<223> OTHER INFORMATION: Xaa is selcted from Pro, Val, Ile and Met
<220> FEATURE:
<221> NAME/KEY: V-segment
<222> LOCATION: (5)..(5)
<223> OTHER INFORMATION: Xaa is selected from Ser, Pro and Ala
<220> FEATURE:
<221> NAME/KEY: V-segment
<222> LOCATION: (6)..(6)
<223> OTHER INFORMATION: Xaa is selected from Gly, Leu, Val and Thr
<220> FEATURE:
<221> NAME/KEY: V-segment
<222> LOCATION: (7)..(7)
<223> OTHER INFORMATION: Xaa is selected from Gly, Tyr, Gln, Lys, Arg,
      Asn and Met
<220> FEATURE:
<221> NAME/KEY: V-segment
<222> LOCATION: (8)..(8)
<223> OTHER INFORMATION: Xaa is selected from Thr, Gly and Ser

<400> SEQUENCE: 8

Gly Ile Xaa Xaa Xaa Xaa Xaa Xaa Thr Val Tyr Ala Asp Ser Val Lys
1               5                   10                  15

Gly

<210> SEQ ID NO 9
<211> LENGTH: 20
<212> TYPE: PRT
<213> ORGANISM: Homo sapiens

<400> SEQUENCE: 9

Ala Leu Pro Arg Ser Gly Tyr Leu Ile Ser Pro His Tyr Tyr Tyr Tyr
1               5                   10                  15

Ala Leu Asp Val
            20

<210> SEQ ID NO 10
<211> LENGTH: 20
<212> TYPE: PRT
<213> ORGANISM: Artificial
<220> FEATURE:
<223> OTHER INFORMATION: Heavy chain CDR3 showing variations
<220> FEATURE:
<221> NAME/KEY: V-segment
<222> LOCATION: (9)..(9)
<223> OTHER INFORMATION: Xaa is selected from Ala, Met and Val
<220> FEATURE:
<221> NAME/KEY: V-segment
<222> LOCATION: (10)..(10)
<223> OTHER INFORMATION: Xaa is selcted from Ser and Lys
```

```
<220> FEATURE:
<221> NAME/KEY: V-segment
<222> LOCATION: (11)..(11)
<223> OTHER INFORMATION: Xaa is selected from Pro, Lys, Thr and His
<220> FEATURE:
<221> NAME/KEY: V-segment
<222> LOCATION: (12)..(12)
<223> OTHER INFORMATION: Xaa is selected from His, Asn, Gly and Gln

<400> SEQUENCE: 10

Ala Leu Pro Arg Ser Gly Tyr Leu Xaa Xaa Xaa Xaa Tyr Tyr Tyr Tyr
1               5                   10                  15

Ala Leu Asp Val
            20

<210> SEQ ID NO 11
<211> LENGTH: 13
<212> TYPE: PRT
<213> ORGANISM: Homo sapiens

<400> SEQUENCE: 11

Ser Gly Ser Ser Ser Asn Ile Gly Arg Asn Tyr Val Tyr
1               5                   10

<210> SEQ ID NO 12
<211> LENGTH: 7
<212> TYPE: PRT
<213> ORGANISM: Homo sapiens

<400> SEQUENCE: 12

Ser Asn Asn Gln Arg Pro Ser
1               5

<210> SEQ ID NO 13
<211> LENGTH: 10
<212> TYPE: PRT
<213> ORGANISM: Homo sapiens

<400> SEQUENCE: 13

Ala Ala Trp Asp Ala Ser Leu Arg Gly Val
1               5                   10

<210> SEQ ID NO 14
<211> LENGTH: 10
<212> TYPE: PRT
<213> ORGANISM: Artificial
<220> FEATURE:
<223> OTHER INFORMATION: Light chain CDR3 showing variations
<220> FEATURE:
<221> NAME/KEY: V-segment
<222> LOCATION: (2)..(2)
<223> OTHER INFORMATION: Xaa is selected from Ala and Ser
<220> FEATURE:
<221> NAME/KEY: V-segment
<222> LOCATION: (4)..(6)
<223> OTHER INFORMATION: Xaa can be any amino acid
<220> FEATURE:
<221> NAME/KEY: V-segment
<222> LOCATION: (7)..(7)
<223> OTHER INFORMATION: Xaa is selected from Leu and Val
<220> FEATURE:
<221> NAME/KEY: V-segment
<222> LOCATION: (9)..(10)
<223> OTHER INFORMATION: Xaa can be any amino acid

<400> SEQUENCE: 14

Ala Xaa Trp Xaa Xaa Xaa Xaa Arg Xaa Xaa
1               5                   10
```

```
<210> SEQ ID NO 15
<211> LENGTH: 133
<212> TYPE: PRT
<213> ORGANISM: Artificial
<220> FEATURE:
<223> OTHER INFORMATION: stop template to generate diverse antibodies
<220> FEATURE:
<221> NAME/KEY: misc_feature
<222> LOCATION: (30)..(35)
<223> OTHER INFORMATION: Xaa can be any naturally occurring amino acid

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Xaa Xaa Xaa Trp Val Arg Gln Ala Pro Gly Lys Gly Leu Glu Trp Val
        35                  40                  45

Ser Gly Ile Arg Pro Ser Gly Gly Thr Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser Ala Ser Thr Lys
    130

<210> SEQ ID NO 16
<211> LENGTH: 53
<212> TYPE: DNA
<213> ORGANISM: Artificial
<220> FEATURE:
<223> OTHER INFORMATION: Mutagenic trimer mix
<220> FEATURE:
<221> NAME/KEY: misc_feature
<222> LOCATION: (20)..(37)
<223> OTHER INFORMATION: n is a, c, g, or t

<400> SEQUENCE: 16
agcaagcggt tttacctttn nnnnnnnnn nnnnnnntgg gttcgccagg cac         53

<210> SEQ ID NO 17
<211> LENGTH: 133
<212> TYPE: PRT
<213> ORGANISM: Artificial
<220> FEATURE:
<223> OTHER INFORMATION: stop template to generate diverse antibodies
<220> FEATURE:
<221> NAME/KEY: misc_feature
<222> LOCATION: (52)..(57)
<223> OTHER INFORMATION: Xaa can be any naturally occurring amino acid
      (except Cys)

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
```

```
                35                  40                  45
Ser Gly Ile Xaa Xaa Xaa Xaa Xaa Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
            115                 120                 125

Ser Ala Ser Thr Lys
        130
```

```
<210> SEQ ID NO 18
<211> LENGTH: 56
<212> TYPE: DNA
<213> ORGANISM: Artificial
<220> FEATURE:
<223> OTHER INFORMATION: Mutagenic trimer mix
<220> FEATURE:
<221> NAME/KEY: misc_feature
<222> LOCATION: (20)..(37)
<223> OTHER INFORMATION: n is a, c, g, or t

<400> SEQUENCE: 18
ggaatgggtt agcggtattn nnnnnnnnn nnnnnnnacc gtttatgcag atagcg        56
```

```
<210> SEQ ID NO 19
<211> LENGTH: 133
<212> TYPE: PRT
<213> ORGANISM: Artificial
<220> FEATURE:
<223> OTHER INFORMATION: stop template to generate diverse antibodies
<220> FEATURE:
<221> NAME/KEY: misc_feature
<222> LOCATION: (100)..(105)
<223> OTHER INFORMATION: Xaa can be any naturally occurring amino acid
      (except Cys)

<400> SEQUENCE: 19

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Lys Tyr
             20                  25                  30

Ile Met Gln Trp Val Arg Gln Ala Pro Gly Lys Gly Leu Glu Trp Val
         35                  40                  45

Ser Gly Ile Arg Pro Ser Gly Gly Thr Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Xaa Xaa Xaa Xaa Xaa Xaa Leu Ile Ser Pro His Tyr Tyr
            100                 105                 110

Tyr Tyr Ala Leu Asp Val Trp Gly Gln Gly Thr Thr Val Thr Val Ser
            115                 120                 125

Ser Ala Ser Thr Lys
        130
```

```
<210> SEQ ID NO 20
<211> LENGTH: 57
<212> TYPE: DNA
<213> ORGANISM: Artificial
<220> FEATURE:
<223> OTHER INFORMATION: Mutagenic trimer mix
<220> FEATURE:
<221> NAME/KEY: misc_feature
<222> LOCATION: (20)..(37)
<223> OTHER INFORMATION: n is a, c, g, or t

<400> SEQUENCE: 20
ttattattgc gcacgtgcan nnnnnnnnnn nnnnnnnctg atttctccgc attatta        57

<210> SEQ ID NO 21
<211> LENGTH: 133
<212> TYPE: PRT
<213> ORGANISM: Artificial
<220> FEATURE:
<223> OTHER INFORMATION: stop template to generate diverse antibodies
<220> FEATURE:
<221> NAME/KEY: misc_feature
<222> LOCATION: (105)..(110)
<223> OTHER INFORMATION: Xaa can be any naturally occurring amino acid
      (except Cys)

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Arg Pro Ser Gly Gly Thr Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Xaa Xaa Xaa Xaa Xaa Xaa Tyr Tyr
            100                 105                 110

Tyr Tyr Ala Leu Asp Val Trp Gly Gln Gly Thr Thr Val Thr Val Ser
        115                 120                 125

Ser Ala Ser Thr Lys
        130

<210> SEQ ID NO 22
<211> LENGTH: 56
<212> TYPE: DNA
<213> ORGANISM: Artificial
<220> FEATURE:
<223> OTHER INFORMATION: Mutagenic trimer mix
<220> FEATURE:
<221> NAME/KEY: misc_feature
<222> LOCATION: (18)..(35)
<223> OTHER INFORMATION: n is a, c, g, or t

<400> SEQUENCE: 22
cactgcctcg tagcggtnnn nnnnnnnnnn nnnntatta ttattatgcc ctggat        56

<210> SEQ ID NO 23
<211> LENGTH: 120
<212> TYPE: PRT
<213> ORGANISM: Artificial
<220> FEATURE:
```

```
<223> OTHER INFORMATION: stop template to generate diverse antibodies
<220> FEATURE:
<221> NAME/KEY: misc_feature
<222> LOCATION: (27)..(32)
<223> OTHER INFORMATION: Xaa can be any naturally occurring amino acid
      (except Cys)

<400> SEQUENCE: 23
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Xaa Xaa Xaa Xaa Xaa Xaa
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly Gln Pro
            100                 105                 110

Lys Ala Ala Pro Ser Val Thr Leu
        115                 120

```
<210> SEQ ID NO 24
<211> LENGTH: 55
<212> TYPE: DNA
<213> ORGANISM: Artificial
<220> FEATURE:
<223> OTHER INFORMATION: Mutagenic trimer mix
<220> FEATURE:
<221> NAME/KEY: misc_feature
<222> LOCATION: (18)..(35)
<223> OTHER INFORMATION: n is a, c, g, or t

<400> SEQUENCE: 24
gctgtagcgg tagcagcnnn nnnnnnnnn nnnnntatgt gtattggtat cagca      55

<210> SEQ ID NO 25
<211> LENGTH: 120
<212> TYPE: PRT
<213> ORGANISM: Artificial
<220> FEATURE:
<223> OTHER INFORMATION: stop template to generate diverse antibodies
<220> FEATURE:
<221> NAME/KEY: misc_feature
<222> LOCATION: (90)..(95)
<223> OTHER INFORMATION: Xaa can be any naturally occurring amino acid
      (except Cys)

<400> SEQUENCE: 25
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

```
Ser Glu Asp Glu Ala Asp Tyr Tyr Cys Xaa Xaa Xaa Xaa Xaa Xaa Leu
            85                  90                  95

Arg Gly Val Phe Gly Gly Gly Thr Lys Leu Thr Val Leu Gly Gln Pro
            100                 105                 110

Lys Ala Ala Pro Ser Val Thr Leu
        115                 120

<210> SEQ ID NO 26
<211> LENGTH: 57
<212> TYPE: DNA
<213> ORGANISM: Artificial
<220> FEATURE:
<223> OTHER INFORMATION: Mutagenic trimer mix
<220> FEATURE:
<221> NAME/KEY: misc_feature
<222> LOCATION: (22)..(39)
<223> OTHER INFORMATION: n is a, c, g, or t

<400> SEQUENCE: 26
gatgaagccg attattattg tnnnnnnnnn nnnnnnnnnc tgcgtggtgt ttttggt      57

<210> SEQ ID NO 27
<211> LENGTH: 120
<212> TYPE: PRT
<213> ORGANISM: Artificial
<220> FEATURE:
<223> OTHER INFORMATION: stop template to generate diverse antibodies
<220> FEATURE:
<221> NAME/KEY: misc_feature
<222> LOCATION: (94)..(99)
<223> OTHER INFORMATION: Xaa can be any naturally occurring amino acid
      (except Cys)

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Xaa Xaa Xaa
            85                  90                  95

Xaa Xaa Xaa Phe Gly Gly Gly Thr Lys Leu Thr Val Leu Gly Gln Pro
            100                 105                 110

Lys Ala Ala Pro Ser Val Thr Leu
        115                 120

<210> SEQ ID NO 28
<211> LENGTH: 55
<212> TYPE: DNA
<213> ORGANISM: Artificial
<220> FEATURE:
<223> OTHER INFORMATION: Mutagenic trimer mix
<220> FEATURE:
<221> NAME/KEY: misc_feature
<222> LOCATION: (20)..(37)
<223> OTHER INFORMATION: n is a, c, g, or t

<400> SEQUENCE: 28
ttattgtgca gcatgggatn nnnnnnnnnn nnnnnntttt ggtggtggca ccaaa         55
```

```
<210> SEQ ID NO 29
<211> LENGTH: 17
<212> TYPE: PRT
<213> ORGANISM: Artificial
<220> FEATURE:
<223> OTHER INFORMATION: Affinity-matured HCDR2

<400> SEQUENCE: 29

Gly Ile Asn Val Pro Leu Tyr Gly Thr Val Tyr Ala Asp Ser Val Lys
1               5                   10                  15

Gly

<210> SEQ ID NO 30
<211> LENGTH: 17
<212> TYPE: PRT
<213> ORGANISM: Artificial
<220> FEATURE:
<223> OTHER INFORMATION: Affinity-matured HCDR2

<400> SEQUENCE: 30

Gly Ile Asn Val Pro Val Gln Gly Thr Val Tyr Ala Asp Ser Val Lys
1               5                   10                  15

Gly

<210> SEQ ID NO 31
<211> LENGTH: 17
<212> TYPE: PRT
<213> ORGANISM: Artificial
<220> FEATURE:
<223> OTHER INFORMATION: Affinity-matured HCDR2

<400> SEQUENCE: 31

Gly Ile Asp Ile Pro Thr Lys Gly Thr Val Tyr Ala Asp Ser Val Lys
1               5                   10                  15

Gly

<210> SEQ ID NO 32
<211> LENGTH: 17
<212> TYPE: PRT
<213> ORGANISM: Artificial
<220> FEATURE:
<223> OTHER INFORMATION: Affinity-matured HCDR2

<400> SEQUENCE: 32

Gly Ile Asp Met Pro Thr Lys Gly Thr Val Tyr Ala Asp Ser Val Lys
1               5                   10                  15

Gly

<210> SEQ ID NO 33
<211> LENGTH: 17
<212> TYPE: PRT
<213> ORGANISM: Artificial
<220> FEATURE:
<223> OTHER INFORMATION: Affinity-matured HCDR2

<400> SEQUENCE: 33

Gly Ile Asn Pro Ala Thr Arg Thr Thr Val Tyr Ala Asp Ser Val Lys
1               5                   10                  15

Gly

<210> SEQ ID NO 34
<211> LENGTH: 17
```

```
<210> SEQ ID NO 34
<211> LENGTH: 17
<212> TYPE: PRT
<213> ORGANISM: Artificial
<220> FEATURE:
<223> OTHER INFORMATION: Affinity-matured HCDR2

<400> SEQUENCE: 34

Gly Ile Asn Pro Ala Thr Lys Thr Thr Val Tyr Ala Asp Ser Val Lys
1               5                   10                  15
Gly

<210> SEQ ID NO 35
<211> LENGTH: 17
<212> TYPE: PRT
<213> ORGANISM: Artificial
<220> FEATURE:
<223> OTHER INFORMATION: Affinity-matured HCDR2

<400> SEQUENCE: 35

Gly Ile Asp Val Pro Val Arg Gly Thr Val Tyr Ala Asp Ser Val Lys
1               5                   10                  15
Gly

<210> SEQ ID NO 36
<211> LENGTH: 17
<212> TYPE: PRT
<213> ORGANISM: Artificial
<220> FEATURE:
<223> OTHER INFORMATION: Affinity-matured HCDR2

<400> SEQUENCE: 36

Gly Ile Asn Pro Ala Thr Arg Ser Thr Val Tyr Ala Asp Ser Val Lys
1               5                   10                  15
Gly

<210> SEQ ID NO 37
<211> LENGTH: 17
<212> TYPE: PRT
<213> ORGANISM: Artificial
<220> FEATURE:
<223> OTHER INFORMATION: Affinity-matured HCDR2

<400> SEQUENCE: 37

Gly Ile Asn Pro Ala Thr Asn Thr Thr Val Tyr Ala Asp Ser Val Lys
1               5                   10                  15
Gly

<210> SEQ ID NO 38
<211> LENGTH: 17
<212> TYPE: PRT
<213> ORGANISM: Artificial
<220> FEATURE:
<223> OTHER INFORMATION: Affinity-matured HCDR2

<400> SEQUENCE: 38

Gly Ile Asn Pro Ala Thr Met Thr Thr Val Tyr Ala Asp Ser Val Lys
1               5                   10                  15
Gly

<210> SEQ ID NO 39
<211> LENGTH: 20
<212> TYPE: PRT
<213> ORGANISM: Artificial
<220> FEATURE:
<223> OTHER INFORMATION: Affinity-matured HCDR3
```

```
<400> SEQUENCE: 39

Ala Leu Pro Arg Ser Gly Tyr Leu Met Lys Lys Asn Tyr Tyr Tyr
1               5                   10                  15

Ala Leu Asp Val
            20

<210> SEQ ID NO 40
<211> LENGTH: 20
<212> TYPE: PRT
<213> ORGANISM: Artificial
<220> FEATURE:
<223> OTHER INFORMATION: Affinity-matured HCDR3

<400> SEQUENCE: 40

Ala Leu Pro Arg Ser Gly Tyr Leu Met Lys Thr Gly Tyr Tyr Tyr
1               5                   10                  15

Ala Leu Asp Val
            20

<210> SEQ ID NO 41
<211> LENGTH: 20
<212> TYPE: PRT
<213> ORGANISM: Artificial
<220> FEATURE:
<223> OTHER INFORMATION: Affinity-matured HCDR3

<400> SEQUENCE: 41

Ala Leu Pro Arg Ser Gly Tyr Leu Val Lys Lys Gln Tyr Tyr Tyr
1               5                   10                  15

Ala Leu Asp Val
            20

<210> SEQ ID NO 42
<211> LENGTH: 20
<212> TYPE: PRT
<213> ORGANISM: Artificial
<220> FEATURE:
<223> OTHER INFORMATION: Affinity-matured HCDR3

<400> SEQUENCE: 42

Ala Leu Pro Arg Ser Gly Tyr Leu Val Lys His Gly Tyr Tyr Tyr
1               5                   10                  15

Ala Leu Asp Val
            20

<210> SEQ ID NO 43
<211> LENGTH: 20
<212> TYPE: PRT
<213> ORGANISM: Artificial
<220> FEATURE:
<223> OTHER INFORMATION: Affinity-matured HCDR3

<400> SEQUENCE: 43

Ala Leu Pro Arg Ser Gly Tyr Leu Met Lys Pro Gly Tyr Tyr Tyr
1               5                   10                  15

Ala Leu Asp Val
            20

<210> SEQ ID NO 44
<211> LENGTH: 13
<212> TYPE: PRT
<213> ORGANISM: Artificial
<220> FEATURE:
```

```
<223> OTHER INFORMATION: Affinity-matured LCDR1

<400> SEQUENCE: 44

Ser Gly Ser Ser Glu Met Thr Val His His Tyr Val Tyr
1               5                   10

<210> SEQ ID NO 45
<211> LENGTH: 13
<212> TYPE: PRT
<213> ORGANISM: Artificial
<220> FEATURE:
<223> OTHER INFORMATION: Affinity-matured LCDR1

<400> SEQUENCE: 45

Ser Gly Ser Ser Phe Ser His Pro His His Tyr Val Tyr
1               5                   10

<210> SEQ ID NO 46
<211> LENGTH: 13
<212> TYPE: PRT
<213> ORGANISM: Artificial
<220> FEATURE:
<223> OTHER INFORMATION: Affinity-matured LCDR1

<400> SEQUENCE: 46

Ser Gly Ser Ser Glu Phe Val Glu Tyr Asn Tyr Val Tyr
1               5                   10

<210> SEQ ID NO 47
<211> LENGTH: 13
<212> TYPE: PRT
<213> ORGANISM: Artificial
<220> FEATURE:
<223> OTHER INFORMATION: Affinity-matured LCDR1

<400> SEQUENCE: 47

Ser Gly Ser Ser Asp Thr Asn Ser His His Tyr Val Tyr
1               5                   10

<210> SEQ ID NO 48
<211> LENGTH: 13
<212> TYPE: PRT
<213> ORGANISM: Artificial
<220> FEATURE:
<223> OTHER INFORMATION: Affinity-matured LCDR1

<400> SEQUENCE: 48

Ser Gly Ser Ser Trp Thr Glu Gln His Asn Tyr Val Tyr
1               5                   10

<210> SEQ ID NO 49
<211> LENGTH: 13
<212> TYPE: PRT
<213> ORGANISM: Artificial
<220> FEATURE:
<223> OTHER INFORMATION: Affinity-matured LCDR1

<400> SEQUENCE: 49

Ser Gly Ser Ser Val Met Val Thr Asn His Tyr Val Tyr
1               5                   10

<210> SEQ ID NO 50
<211> LENGTH: 13
<212> TYPE: PRT
<213> ORGANISM: Artificial
<220> FEATURE:
<223> OTHER INFORMATION: Affinity-matured LCDR1
```

```
<400> SEQUENCE: 50

Ser Gly Ser Ser Gly Met Val Glu Gln Asn Tyr Val Tyr
1               5                   10

<210> SEQ ID NO 51
<211> LENGTH: 13
<212> TYPE: PRT
<213> ORGANISM: Artificial
<220> FEATURE:
<223> OTHER INFORMATION: Affinity-matured LCDR1

<400> SEQUENCE: 51

Ser Gly Ser Ser Phe Lys Val Glu Glu Thr Tyr Val Tyr
1               5                   10

<210> SEQ ID NO 52
<211> LENGTH: 10
<212> TYPE: PRT
<213> ORGANISM: Artificial
<220> FEATURE:
<223> OTHER INFORMATION: Affinity-matured LCDR3

<400> SEQUENCE: 52

Ala Ser Trp Tyr Asn Asp Leu Arg Gly Val
1               5                   10

<210> SEQ ID NO 53
<211> LENGTH: 10
<212> TYPE: PRT
<213> ORGANISM: Artificial
<220> FEATURE:
<223> OTHER INFORMATION: Affinity-matured LCDR3

<400> SEQUENCE: 53

Ala Ser Trp Glu Ile Pro Leu Arg Gly Val
1               5                   10

<210> SEQ ID NO 54
<211> LENGTH: 10
<212> TYPE: PRT
<213> ORGANISM: Artificial
<220> FEATURE:
<223> OTHER INFORMATION: Affinity-matured LCDR3

<400> SEQUENCE: 54

Ala Ser Trp Thr Asn Glu Leu Arg Gly Val
1               5                   10

<210> SEQ ID NO 55
<211> LENGTH: 10
<212> TYPE: PRT
<213> ORGANISM: Artificial
<220> FEATURE:
<223> OTHER INFORMATION: Affinity-matured LCDR3

<400> SEQUENCE: 55

Ala Ser Trp Trp Asn Asp Leu Arg Gly Val
1               5                   10

<210> SEQ ID NO 56
<211> LENGTH: 10
<212> TYPE: PRT
<213> ORGANISM: Artificial
<220> FEATURE:
<223> OTHER INFORMATION: Affinity-matured LCDR3
```

<400> SEQUENCE: 56

Ala Ser Trp Glu Leu Pro Leu Arg Gly Val
1               5                   10

<210> SEQ ID NO 57
<211> LENGTH: 10
<212> TYPE: PRT
<213> ORGANISM: Artificial
<220> FEATURE:
<223> OTHER INFORMATION: Affinity-matured LCDR3

<400> SEQUENCE: 57

Ala Ser Trp Ser Ile Pro Leu Arg Gly Val
1               5                   10

<210> SEQ ID NO 58
<211> LENGTH: 10
<212> TYPE: PRT
<213> ORGANISM: Artificial
<220> FEATURE:
<223> OTHER INFORMATION: Affinity-matured LCDR3

<400> SEQUENCE: 58

Ala Ser Trp Glu Val Pro Leu Arg Gly Val
1               5                   10

<210> SEQ ID NO 59
<211> LENGTH: 10
<212> TYPE: PRT
<213> ORGANISM: Artificial
<220> FEATURE:
<223> OTHER INFORMATION: Affinity-matured LCDR3

<400> SEQUENCE: 59

Ala Ala Trp Asp Pro Gln Val Arg Leu Ala
1               5                   10

<210> SEQ ID NO 60
<211> LENGTH: 10
<212> TYPE: PRT
<213> ORGANISM: Artificial
<220> FEATURE:
<223> OTHER INFORMATION: Affinity-matured LCDR3

<400> SEQUENCE: 60

Ala Ala Trp Asp Gln Gln Val Arg Leu Asp
1               5                   10

<210> SEQ ID NO 61
<211> LENGTH: 10
<212> TYPE: PRT
<213> ORGANISM: Artificial
<220> FEATURE:
<223> OTHER INFORMATION: Affinity-matured LCDR3

<400> SEQUENCE: 61

Ala Ala Trp Asp Gln Gln Val Arg Lys Thr
1               5                   10

<210> SEQ ID NO 62
<211> LENGTH: 10
<212> TYPE: PRT
<213> ORGANISM: Artificial
<220> FEATURE:
<223> OTHER INFORMATION: Affinity-matured LCDR3

<400> SEQUENCE: 62

```
Ala Ala Trp Asp Glu Arg Val Arg Leu Met
1               5                   10

<210> SEQ ID NO 63
<211> LENGTH: 10
<212> TYPE: PRT
<213> ORGANISM: Artificial
<220> FEATURE:
<223> OTHER INFORMATION: Affinity-matured LCDR3

<400> SEQUENCE: 63

Ala Ala Trp Asp Asn Gln Val Arg Leu Gly
1               5                   10

<210> SEQ ID NO 64
<211> LENGTH: 21
<212> TYPE: DNA
<213> ORGANISM: Artificial
<220> FEATURE:
<223> OTHER INFORMATION: Sequencing primer

<400> SEQUENCE: 64
gtccttgacc aggcagccca g                                         21

<210> SEQ ID NO 65
<211> LENGTH: 21
<212> TYPE: DNA
<213> ORGANISM: Artificial
<220> FEATURE:
<223> OTHER INFORMATION: Sequencing primer

<400> SEQUENCE: 65
gtgagttagc tcactcatta g                                         21

<210> SEQ ID NO 66
<211> LENGTH: 21
<212> TYPE: DNA
<213> ORGANISM: Artificial
<220> FEATURE:
<223> OTHER INFORMATION: Sequencing primer

<400> SEQUENCE: 66
ttttcatcgg cattttcggt c                                         21

<210> SEQ ID NO 67
<211> LENGTH: 24
<212> TYPE: DNA
<213> ORGANISM: Artificial
<220> FEATURE:
<223> OTHER INFORMATION: Sequencing primer

<400> SEQUENCE: 67
ccatctgatg agcagttgaa atct                                      24

<210> SEQ ID NO 68
<211> LENGTH: 24
<212> TYPE: DNA
<213> ORGANISM: Artificial
<220> FEATURE:
<223> OTHER INFORMATION: Sequencing primer

<400> SEQUENCE: 68
gttcccgccc tcctctgagg agct                                      24

<210> SEQ ID NO 69
```

```
<211> LENGTH: 23
<212> TYPE: DNA
<213> ORGANISM: Artificial
<220> FEATURE:
<223> OTHER INFORMATION: Sequencing primer

<400> SEQUENCE: 69
agcggataac aatttcacac agg                                              23

<210> SEQ ID NO 70
<211> LENGTH: 19
<212> TYPE: DNA
<213> ORGANISM: Artificial
<220> FEATURE:
<223> OTHER INFORMATION: Sequencing primer

<400> SEQUENCE: 70
ggttctggca aatattctg                                                   19

<210> SEQ ID NO 71
<211> LENGTH: 19
<212> TYPE: DNA
<213> ORGANISM: Artificial
<220> FEATURE:
<223> OTHER INFORMATION: Sequencing primer

<400> SEQUENCE: 71
gttgcaccga ccgaatgta                                                   19

<210> SEQ ID NO 72
<211> LENGTH: 25
<212> TYPE: DNA
<213> ORGANISM: Artificial
<220> FEATURE:
<223> OTHER INFORMATION: Sequencing primer

<400> SEQUENCE: 72
accgtgagct ggaacagcgg tgcgc                                            25

<210> SEQ ID NO 73
<211> LENGTH: 129
<212> TYPE: PRT
<213> ORGANISM: Artificial
<220> FEATURE:
<223> OTHER INFORMATION: Affinity-matured vH region

<400> SEQUENCE: 73
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Asp Ile Pro Thr Lys Gly Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser

```
<210> SEQ ID NO 74
<211> LENGTH: 129
<212> TYPE: PRT
<213> ORGANISM: Artificial
<220> FEATURE:
<223> OTHER INFORMATION: Affinity-matured vH region

<400> SEQUENCE: 74
```

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Ser | Lys | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ile | Met | Gln | Trp | Val | Arg | Gln | Ala | Pro | Gly | Lys | Gly | Leu | Glu | Trp | Val |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ser | Gly | Ile | Asn | Val | Pro | Val | Gln | Gly | Thr | Val | Tyr | Ala | Asp | Ser | Val |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Lys | Gly | Arg | Phe | Thr | Ile | Ser | Arg | Asp | Asn | Ser | Lys | Asn | Thr | Leu | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Val | Tyr | Tyr | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Ala | Leu | Pro | Arg | Ser | Gly | Tyr | Leu | Ile | Ser | Pro | His | Tyr | Tyr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Tyr | Tyr | Ala | Leu | Asp | Val | Trp | Gly | Gln | Gly | Thr | Thr | Val | Thr | Val | Ser |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

Ser

```
<210> SEQ ID NO 75
<211> LENGTH: 120
<212> TYPE: PRT
<213> ORGANISM: Artificial
<220> FEATURE:
<223> OTHER INFORMATION: Affinity-matured vL region

<400> SEQUENCE: 75
```

| Gln | Ser | Val | Leu | Thr | Gln | Pro | Pro | Ser | Ala | Ser | Gly | Thr | Pro | Gly | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Val | Thr | Ile | Ser | Cys | Ser | Gly | Ser | Ser | Glu | Met | Thr | Val | His | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Val | Tyr | Trp | Tyr | Gln | Gln | Leu | Pro | Gly | Thr | Ala | Pro | Lys | Leu | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ile | Tyr | Ser | Asn | Asn | Gln | Arg | Pro | Ser | Gly | Val | Pro | Asp | Arg | Phe | Ser |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Gly | Ser | Lys | Ser | Gly | Thr | Ser | Ala | Ser | Leu | Ala | Ile | Ser | Gly | Leu | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ser | Glu | Asp | Glu | Ala | Asp | Tyr | Tyr | Cys | Ala | Ala | Trp | Asp | Ala | Ser | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Arg | Gly | Val | Phe | Gly | Gly | Gly | Thr | Lys | Leu | Thr | Val | Leu | Gly | Gln | Pro |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Lys | Ala | Ala | Pro | Ser | Val | Thr | Leu |
|-----|-----|-----|-----|-----|-----|-----|-----|
|     |     |     | 115 |     |     |     | 120 |

```
<210> SEQ ID NO 76
<211> LENGTH: 130
<212> TYPE: PRT
<213> ORGANISM: Artificial
<220> FEATURE:
```

<223> OTHER INFORMATION: Affinity-matured vH region

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Asp Met Pro Thr Lys Gly Gly Thr Val Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ala Leu Pro Arg Ser Gly Tyr Leu Ile Ser Pro His Tyr
            100                 105                 110

Tyr Tyr Tyr Ala Leu Asp Val Trp Gly Gln Gly Thr Thr Val Thr Val
        115                 120                 125

Ser Ser
    130

<210> SEQ ID NO 77
<211> LENGTH: 131
<212> TYPE: PRT
<213> ORGANISM: Artificial
<220> FEATURE:
<223> OTHER INFORMATION: Affinity-matured vH region

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Asn Val Pro Leu Tyr Gly Gly Thr Val Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Ala Leu Pro Arg Ser Gly Tyr Leu Ile Ser Pro His
            100                 105                 110

Tyr Tyr Tyr Tyr Ala Leu Asp Val Trp Gly Gln Gly Thr Thr Val Thr
        115                 120                 125

Val Ser Ser
    130

UNITED STATES PATENT AND TRADEMARK OFFICE
CERTIFICATE OF CORRECTION

PATENT NO. : 9,856,326 B2  
APPLICATION NO. : 15/343447  
DATED : January 2, 2018  
INVENTOR(S) : Con Panousis et al.

Page 1 of 1

It is certified that error appears in the above-identified patent and that said Letters Patent is hereby corrected as shown below:

In the Claims

Claim 1, Column 83, Lines 18-19, "$X_3$ is 5, P, or A;" should read -- $X_3$ is S, P, or A; --

Signed and Sealed this  
Seventeenth Day of April, 2018

Andrei Iancu  
*Director of the United States Patent and Trademark Office*